US011638593B2

(12) United States Patent
Chong et al.

(10) Patent No.: US 11,638,593 B2
(45) Date of Patent: May 2, 2023

(54) INSERTION DEVICE SYSTEMS AND METHODS

(71) Applicant: Medtronic MiniMed, Inc., Northridge, CA (US)

(72) Inventors: Colin A. Chong, Glendale, CA (US); Eric M. Lorenzen, Altadena, CA (US); Rafael Bikovsky, Oak Park, CA (US); Arsen Ibranyan, Glendale, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 421 days.

(21) Appl. No.: 16/861,106

(22) Filed: Apr. 28, 2020

(65) Prior Publication Data

US 2020/0253632 A1    Aug. 13, 2020

Related U.S. Application Data

(60) Continuation of application No. 15/908,736, filed on Feb. 28, 2018, now Pat. No. 10,675,055, which is a
(Continued)

(51) Int. Cl.
*A61M 5/142* (2006.01)
*A61B 17/34* (2006.01)
(Continued)

(52) U.S. Cl.
CPC ..... *A61B 17/3415* (2013.01); *A61M 5/14248* (2013.01); *A61M 5/158* (2013.01);
(Continued)

(58) Field of Classification Search
CPC .. A61M 5/46; A61M 5/14248; A61M 5/1413; A61M 2005/14252;
(Continued)

(56) References Cited

U.S. PATENT DOCUMENTS 3,701,345 A    10/1972 Heilman et al.
3,884,230 A    5/1975 Wulff
(Continued)

FOREIGN PATENT DOCUMENTS

DE    31 44 825 A1    5/1983
EP    0 927 12 A2    11/1983
(Continued)

OTHER PUBLICATIONS

International Preliminary Report on Patentability dated Mar. 6, 2012, from related international patent application No. PCT/US2010/047590.
(Continued)

*Primary Examiner* — Laura A Bouchelle
(74) *Attorney, Agent, or Firm* — Fortem IP LLP

(57) ABSTRACT

An actuation device includes a lancing device held by and moveable relative to a distal end portion of a housing. A drive member is supported by the housing and arranged to engage the lancing device to move the lancing device in the first direction from a retracted position to an extended position upon movement of the drive member in a first direction. A piercing member of the lancing device is arranged to extend from the distal end portion of the housing by a first distance when the lancing device is moved to the extended position, the first distance being adjustable by adjusting the retracted position of the lancing device relative to the distal end portion of the housing.

19 Claims, 32 Drawing Sheets

Related U.S. Application Data division of application No. 14/594,014, filed on Jan. 9, 2015, now Pat. No. 9,943,332, which is a division of application No. 13/015,051, filed on Jan. 27, 2011, now Pat. No. 8,932,256, which is a continuation-in-part of application No. 12/553,038, filed on Sep. 2, 2009, now Pat. No. 8,900,190.

(51) Int. Cl.
  *A61M 5/158* (2006.01)
  *A61M 5/14* (2006.01)
  *A61M 5/145* (2006.01)
  *A61B 17/00* (2006.01)

(52) U.S. Cl.
  CPC .......... *A61B 2017/00526* (2013.01); *A61B 2017/347* (2013.01); *A61M 5/1413* (2013.01); *A61M 5/1456* (2013.01); *A61M 5/14244* (2013.01); *A61M 2005/14252* (2013.01); *A61M 2005/14268* (2013.01); *A61M 2005/1583* (2013.01); *A61M 2005/1585* (2013.01); *A61M 2209/045* (2013.01); *Y10T 29/49002* (2015.01); *Y10T 29/49826* (2015.01)

(58) Field of Classification Search
  CPC ..... A61M 2005/1585; A61B 5/150175; A61B 5/150183; A61B 5/150198
  See application file for complete search history.

(56) References Cited

U.S. PATENT DOCUMENTS

| | | |
|---|---|---|
| 3,994,295 A | 11/1976 | Wulff |
| 4,633,232 A | 12/1986 | Nelson et al. |
| 4,838,857 A | 6/1989 | Strowe et al. |
| 5,106,375 A | 4/1992 | Conero |
| 5,122,123 A | 6/1992 | Vaillancourt |
| 5,176,662 A | 1/1993 | Bartholomew et al. |
| 5,236,416 A | 8/1993 | Mcdaniel et al. |
| 5,334,188 A | 8/1994 | Inoue et al. |
| 5,533,981 A | 7/1996 | Mandro et al. |
| 5,628,309 A | 5/1997 | Brown |
| 5,628,764 A * | 5/1997 | Schraga ........... A61B 5/150618 606/181 |
| 5,662,612 A | 9/1997 | Niehoff |
| 5,697,916 A | 12/1997 | Schraga |
| 5,954,697 A | 9/1999 | Srisathapat et al. |
| 6,045,533 A | 4/2000 | Kriesel et al. |
| 6,283,943 B1 | 9/2001 | Dy et al. |
| 6,299,131 B1 | 10/2001 | Ryan |
| 6,416,402 B1 | 7/2002 | Moore |
| 6,423,035 B1 | 7/2002 | Das et al. |
| 6,461,329 B1 | 10/2002 | Van Antwerp et al. |
| 6,699,218 B2 | 3/2004 | Flaherty et al. |
| 6,727,689 B1 | 4/2004 | Furlong et al. |
| 6,740,059 B2 | 5/2004 | Flaherty |
| 6,749,587 B2 | 6/2004 | Flaherty |
| 6,830,558 B2 | 12/2004 | Flaherty et al. |
| 6,945,760 B2 | 9/2005 | Gray et al. |
| 6,960,192 B1 | 11/2005 | Flaherty et al. |
| 7,018,360 B2 | 3/2006 | Flaherty et al. |
| 7,396,353 B2 | 7/2008 | Lorenzen et al. |
| 7,811,279 B2 | 10/2010 | John |
| 7,935,104 B2 | 5/2011 | Yodfat et al. |
| 8,105,279 B2 | 1/2012 | Mernoe et al. |
| 8,152,771 B2 | 4/2012 | Mogensen et al. |
| 8,308,679 B2 | 11/2012 | Hanson et al. |
| 8,435,209 B2 | 5/2013 | Hanson et al. |
| 8,858,500 B2 | 10/2014 | Hanson et al. |
| 8,882,710 B2 | 11/2014 | Chong et al. |
| 8,900,190 B2 | 12/2014 | Chong et al. |
| 8,998,840 B2 | 4/2015 | Hanson et al. |
| 8,998,858 B2 | 4/2015 | Chong et al. |
| 9,039,653 B2 | 5/2015 | Chong et al. |
| 9,039,659 B2 | 5/2015 | Hanson et al. |
| 9,421,321 B2 | 8/2016 | Hanson et al. |
| 9,518,813 B2 | 12/2016 | Hanson et al. |
| 9,545,474 B2 | 1/2017 | Hanson et al. |
| 9,610,405 B2 | 4/2017 | Hanson et al. |
| 10,322,233 B2 | 6/2019 | Hanson et al. |
| 10,350,353 B2 | 7/2019 | Hanson et al. |
| 2001/0034506 A1 | 10/2001 | Hirschman et al. |
| 2001/0041869 A1 | 11/2001 | Causey et al. |
| 2002/0128595 A1 | 9/2002 | Weston et al. |
| 2003/0007891 A1 | 1/2003 | Wilson |
| 2004/0002682 A1 | 1/2004 | Kovelman et al. |
| 2004/0162521 A1 | 8/2004 | Bengtsson |
| 2004/0186432 A1 | 9/2004 | Barry et al. |
| 2004/0204673 A1 | 10/2004 | Flaherty |
| 2005/0020980 A1 | 1/2005 | Inoue et al. |
| 2005/0065472 A1 | 3/2005 | Cindrich et al. |
| 2005/0101932 A1 | 5/2005 | Cote et al. |
| 2005/0249616 A1 | 11/2005 | Huang et al. |
| 2006/0061353 A1 | 3/2006 | Etherington et al. |
| 2006/0079765 A1 | 4/2006 | Neer et al. |
| 2006/0200020 A1 | 9/2006 | Brister et al. |
| 2007/0049865 A1 | 3/2007 | Radmer et al. |
| 2007/0060871 A1 | 3/2007 | Istoc et al. |
| 2007/0073236 A1 | 3/2007 | Mernoe et al. |
| 2007/0083222 A1 * | 4/2007 | Schraga ........... A61B 5/150183 606/181 |
| 2007/0156094 A1 | 7/2007 | Safabash et al. |
| 2007/0185450 A1 | 8/2007 | De et al. |
| 2007/0191702 A1 | 8/2007 | Yodfat et al. |
| 2007/0191770 A1 | 8/2007 | Moberg et al. |
| 2007/0270744 A1 | 11/2007 | Dacquay et al. |
| 2008/0024812 A1 | 1/2008 | Miyazaki et al. |
| 2008/0051697 A1 | 2/2008 | Mounce et al. |
| 2008/0051711 A1 | 2/2008 | Mounce et al. |
| 2008/0051714 A1 | 2/2008 | Moberg et al. |
| 2008/0077081 A1 | 3/2008 | Mounce et al. |
| 2008/0097321 A1 | 4/2008 | Mounce et al. |
| 2008/0097328 A1 | 4/2008 | Moberg et al. |
| 2008/0097381 A1 | 4/2008 | Moberg et al. |
| 2008/0133702 A1 | 6/2008 | Sharma et al. |
| 2008/0264261 A1 | 10/2008 | Kavazov et al. |
| 2008/0269687 A1 | 10/2008 | Chong et al. |
| 2008/0269713 A1 | 10/2008 | Kavazov |
| 2008/0281270 A1 | 11/2008 | Cross et al. |
| 2008/0319394 A1 | 12/2008 | Yodfat et al. |
| 2008/0319414 A1 | 12/2008 | Yodfat et al. |
| 2008/0319416 A1 | 12/2008 | Yodfat et al. |
| 2009/0054810 A1 | 2/2009 | Zanzucchi et al. |
| 2009/0069750 A1 | 3/2009 | Schraga |
| 2009/0099523 A1 | 4/2009 | Grant et al. |
| 2009/0143735 A1 | 6/2009 | De et al. |
| 2009/0156990 A1 | 6/2009 | Wenger et al. |
| 2009/0182301 A1 | 7/2009 | Bassarab et al. |
| 2009/0216194 A1 | 8/2009 | Pedersen et al. |
| 2009/0259183 A1 | 10/2009 | Chong et al. |
| 2009/0259198 A1 | 10/2009 | Chong et al. |
| 2009/0264825 A1 | 10/2009 | Cote et al. |
| 2009/0326458 A1 | 12/2009 | Chong et al. |
| 2010/0057014 A1 | 3/2010 | Cane |
| 2010/0137790 A1 | 6/2010 | Yodfat |
| 2010/0152658 A1 | 6/2010 | Hanson et al. |
| 2010/0274180 A1 | 10/2010 | Donovan et al. |
| 2010/0292651 A1 | 11/2010 | Gescheit et al. |
| 2011/0166512 A1 | 7/2011 | Both et al. |
| 2011/0178461 A1 | 7/2011 | Chong et al. |
| 2011/0213306 A1 | 9/2011 | Hanson et al. |
| 2012/0130312 A1 | 5/2012 | Mernoe et al. |
| 2012/0179101 A1 | 7/2012 | Briones et al. |
| 2012/0215163 A1 | 8/2012 | Hanson et al. |
| 2013/0253422 A1 | 9/2013 | Hanson et al. |
| 2017/0157321 A1 | 6/2017 | Hanson et al. |

(56) References Cited

U.S. PATENT DOCUMENTS

| | | |
|---|---|---|
| 2017/0157322 A1 | 6/2017 | Hanson et al. |
| 2019/0282756 A1 | 9/2019 | Hanson et al. |

FOREIGN PATENT DOCUMENTS

| | | | |
|---|---|---|---|
| EP | 0 317 808 A2 | 5/1989 | |
| EP | 0 937 475 A2 | 8/1999 | |
| EP | 1 177 802 A1 | 2/2002 | |
| EP | 1 752 172 A1 | 2/2007 | |
| EP | 2 077 128 B1 | 12/2010 | |
| GB | 2 327 151 A | 1/1999 | |
| JP | 11-339439 A | 12/1999 | |
| WO | WO-86/02562 A1 | 5/1986 | |
| WO | WO-99/33504 A1 | 7/1999 | |
| WO | WO-00/47254 A1 | 8/2000 | |
| WO | WO-01/68163 A2 | 9/2001 | |
| WO | WO-2006/031500 | 3/2006 | |
| WO | WO-2006/076656 | 7/2006 | |
| WO | WO-2006/121921 A2 | 11/2006 | |
| WO | WO-2006/122406 | 11/2006 | |
| WO | WO-2006/124756 | 11/2006 | |
| WO | WO-2008/024810 A2 | 2/2008 | |
| WO | WO-2008/024812 A2 | 2/2008 | |
| WO | WO-2008/024814 A2 | 2/2008 | |
| WO | WO-2008/078318 | 7/2008 | |
| WO | WO-2008/092782 A1 | 8/2008 | |
| WO | WO-2008/133702 A1 | 11/2008 | |
| WO | WO-2009/001346 | 12/2008 | |
| WO | WO-2009/016638 | 2/2009 | |
| WO | WO-2009/033032 A1 | 3/2009 | |
| WO | WO-2009/066288 A1 | 5/2009 | |
| WO | WO-2009/093759 A1 | 7/2009 | |
| WO | WO-2009/098291 A1 | 8/2009 | |
| WO | WO-2009/106517 | 9/2009 | |
| WO | WO-2009/125398 A2 | 10/2009 | |
| WO | WO-2009/135667 A1 | 11/2009 | |
| WO | WO-2009/144726 A1 | 12/2009 | |
| WO | WO-2010/042814 A2 | 4/2010 | |
| WO | WO-2011/082256 | 7/2011 | |
| WO | WO-2011/090629 A2 | 7/2011 | |
| WO | WO-2011/119768 | 9/2011 | |

OTHER PUBLICATIONS

International Preliminary Report on Patentability dated May 20, 2014, from related international application No. PCT/US2012/064454.
International Search Report and Written Opinion dated Aug. 28, 2012, from related international application No. PCT/US2012/022881.
International Search Report and Written Opinion dated Aug. 7, 2012, from related international application No. PCT/US2012/022883.
International Search Report and Written Opinion dated Dec. 11, 2012, from related informational application No. PCT/US2012/055661.
International Search Report and Written Opinion dated Dec. 12, 2012, from related international application No. PCT/US2011/066501.
International Search Report and Written Opinion dated Dec. 6, 2011, from related international application No. PCT/US2010/062414.
International Search Report and Written Opinion dated Jun. 12, 2013, from related international application No. PCT/US2012/064454.
International Search Report and Written Opinion dated Mar. 1, 2011, from related international application No. PCT/US2010/060892.
International Search Report and Written Opinion dated Sep. 6, 2011, from related international application No. PCT/US2010/047590.
International Search Report dated Aug. 16, 2012, from related international application No. PCT/US2010/060895.
International Search Report dated Oct. 24, 2012, from related international patent application No. PCT/US2011/066504.
Japanese Office Action dated Mar. 25, 2014, from related Japanese Patent Application No. 2012-528022.
Japanese Office Action from related Japanese Patent Application No. 2012-528022, dated Jun. 25, 2013.
Non-Final Office Action dated Oct. 24, 2019, from U.S. Appl. No. 15/908,736.
Non-Final Office Action dated Oct. 5, 2018, from U.S. Appl. No. 15/438,662.
Non-Final Office Action dated Oct. 5, 2018, from U.S. Appl. No. 15/438,676.
Notice of Allowance dated Feb. 12, 2020, from U.S. Appl. No. 15/908,736.
Notice of Allowance dated Feb. 25, 2019, from U.S. Appl. No. 15/438,662.
Notice of Allowance dated Mar. 4, 2019, from U.S. Appl. No. 15/438,676.
Partial International Search Report dated Apr. 16, 2012, from related international application No. PCT/US2011/066504.
Partial International Search Report dated Jun. 7, 2011, from related international application No. PCT/US2010/062414.
Partial International Search Report dated Mar. 21, 2011, from related international patent application No. PCT/US2010/060895.
Partial International Search Report dated Mar. 23, 2011, from related international patent application No. PCT/US2010/047590.
Partial Search Report dated Feb. 4, 2013, from related international application No. PCT/US2012/064454.
Partial Search Report dated Jul. 9, 2012, from related international patent application No. PCT/US2011/066501.
Partial Search Report dated May 4, 2012, from related international application No. PCT/US2012/022881.
U.S. Notice of Allowance dated Dec. 20, 2012, from related U.S. Appl. No. 13/235,228.
U.S. Notice of Allowance dated Sep. 22, 2014, from related U.S. Appl. No. 13/015,051.
U.S. Office Action dated Jan. 16, 2015, from related U.S. Appl. No. 13/462,752.
U.S. Notice of Allowance Aug. 1, 2014, from related U.S. Appl. No. 12/553,038.
U.S. Notice of Allowance dated Aug. 19, 2016, from related U.S. Appl. No. 13/900,463.
U.S. Notice of Allowance dated Aug. 25, 2016, from related U.S. Appl. No. 14/720,663.
U.S. Notice of Allowance dated Dec. 1, 2016, from related U.S. Appl. No. 13/791,773.
U.S. Notice of Allowance dated Dec. 19, 2014, from related U.S. Appl. No. 12/650,378.
U.S. Notice of Allowance dated Dec. 26, 2017, from U.S. Appl. No. 14/594,014.
U.S. Notice of Allowance dated Feb. 2, 2015, from related U.S. Appl. No. 12/974,117.
U.S. Notice of Allowance dated Jan. 21, 2015, from related U.S. Appl. No. 13/421,564.
U.S. Notice of Allowance dated Jul. 24, 2014, from related U.S. Appl. No. 13/015,028.
U.S. Notice of Allowance dated Jul. 7, 2014, from related U.S. Appl. No. 12/650,287.
U.S. Notice of Allowance dated May 20, 2016, from related U.S. Appl. No. 12/649,172.
U.S. Notice of Allowance dated May 20, 2016, from related U.S. Appl. No. 13/103,014.
U.S. Notice of Allowance dated Nov. 6, 2015, from related U.S. Appl. No. 12/649,172.
U.S. Notice of Allowance dated Oct. 20, 2014, from related U.S. Appl. No. 12/974,106.
U.S. Notice of Allowance dated Sep. 19, 2012, from related U.S. Appl. No. 12/649,619.
U.S. Notice of Allowance dated Sep. 25, 2015, from related U.S. Appl. No. 13/103,014.
U.S. Office Action dated Apr. 25, 2016, from related U.S. Appl. No. 13/900,463.

(56) References Cited

OTHER PUBLICATIONS

U.S. Office Action dated Aug. 1, 2012, from related U.S. Appl. No. 13/015,028.
U.S. Office Action dated Aug. 16, 2012, from related U.S. Appl. No. 12/649,619.
U.S. Office Action dated Aug. 2, 2012, from related U.S. Appl. No. 12/974,106.
U.S. Office Action dated Aug.t 2, 2012, from related U.S. Appl. No. 12/974,117.
U.S. Office Action dated Aug. 2, 2012, from related U.S. Appl. No. 13/015,051.
U.S. Office Action dated Dec. 19, 2013, from related U.S. Appl. No. 13/421,564.
U.S. Office Action dated Dec. 22, 2011, from related U.S. Appl. No. 12/649,619.
U.S. Office Action dated Dec. 28, 2012, from related U.S. Appl. No. 12/553,038.
U.S. Office Action dated Feb. 10, 2016, from related U.S. Appl. No. 13/462,752.
U.S. Office Action dated Feb. 2, 2012, from related U.S. Appl. No. 12/553,038.
U.S. Office Action dated Jan. 16, 2015, from related U.S. Appl. No. 13/791,773.
U.S. Office Action dated Jan. 29, 2016, from related U.S. Appl. No. 13/791,773.
U.S. Office Action dated Jan. 9, 2015, from related U.S. Appl. No. 12/649,172.
U.S. Office Action dated Jul. 1, 2014, from related U.S. Appl. No. 12/974,106.
U.S. Office Action dated Jul. 16, 2 015, from related U.S. Appl. No. 13/103,014.
U.S. Office Action dated Jul. 20, 2012, from related U.S. Appl. No. 12/553,038.
U.S. Office Action dated Jul. 20, 2012, from related U.S. Appl. No. 12/650,378.
U.S. Office Action dated Jul. 25, 2017, from U.S. Appl. No. 14/594,014.
U.S. Office Action dated Jun. 1, 2016, from related U.S. Appl. No. 13/791,773.
U.S. Office Action dated Jun. 18, 2 012, from related U.S. Appl. No. 12/650,287.
U.S. Office Action dated Jun. 19, 2012, from related U.S. Appl. No. 12/649,172.
U.S. Office Action dated Jun. 20, 2013, from related U.S. Appl. No. 12/553,038.
U.S. Office Action dated Jun. 24, 2014, from related U.S. Appl. No. 12/649,172.
U.S. Office Action dated Mar. 20, 2017, from U.S. Appl. No. 13/462,752.
U.S. Office Action dated Mar. 3, 2011, from related U.S. Appl. No. 12/649,172.
U.S. Office Action dated May 22, 2013, from related U.S. Appl. No. 13/103,014.
U.S. Office Action dated May 28, 2015, from related U.S. Appl. No. 13/462,752.
U.S. Office Action dated Nov. 6, 2013, from related U.S. Appl. No. 13/462,752.
U.S. Office Action dated Oct. 27, 2016, from related U.S. Appl. No. 13/462,752.
U.S. Office Action dated Oct. 30, 2017, from U.S. Appl. No. 13/462,752.
U.S. Office Action dated Oct. 7, 2010, from related U.S. Appl. No. 12/649,172.
U.S. Office Action dated Oct. 9, 2014, from related U.S. Appl. No. 12/974,117.
U.S. Office Action dated Sep. 11, 2014, from related U.S. Appl. No. 13/462,752.
U.S. Office Action dated Sep. 30, 2015, from related U.S. Appl. No. 13/462,752.
U.S. Office Action dated Sep. 5, 2014, from related U.S. Appl. No. 12/650,378.
U.S. Office Action dated Sep. 8, 2014, from related U.S. Appl. No. 13/421,564.

* cited by examiner

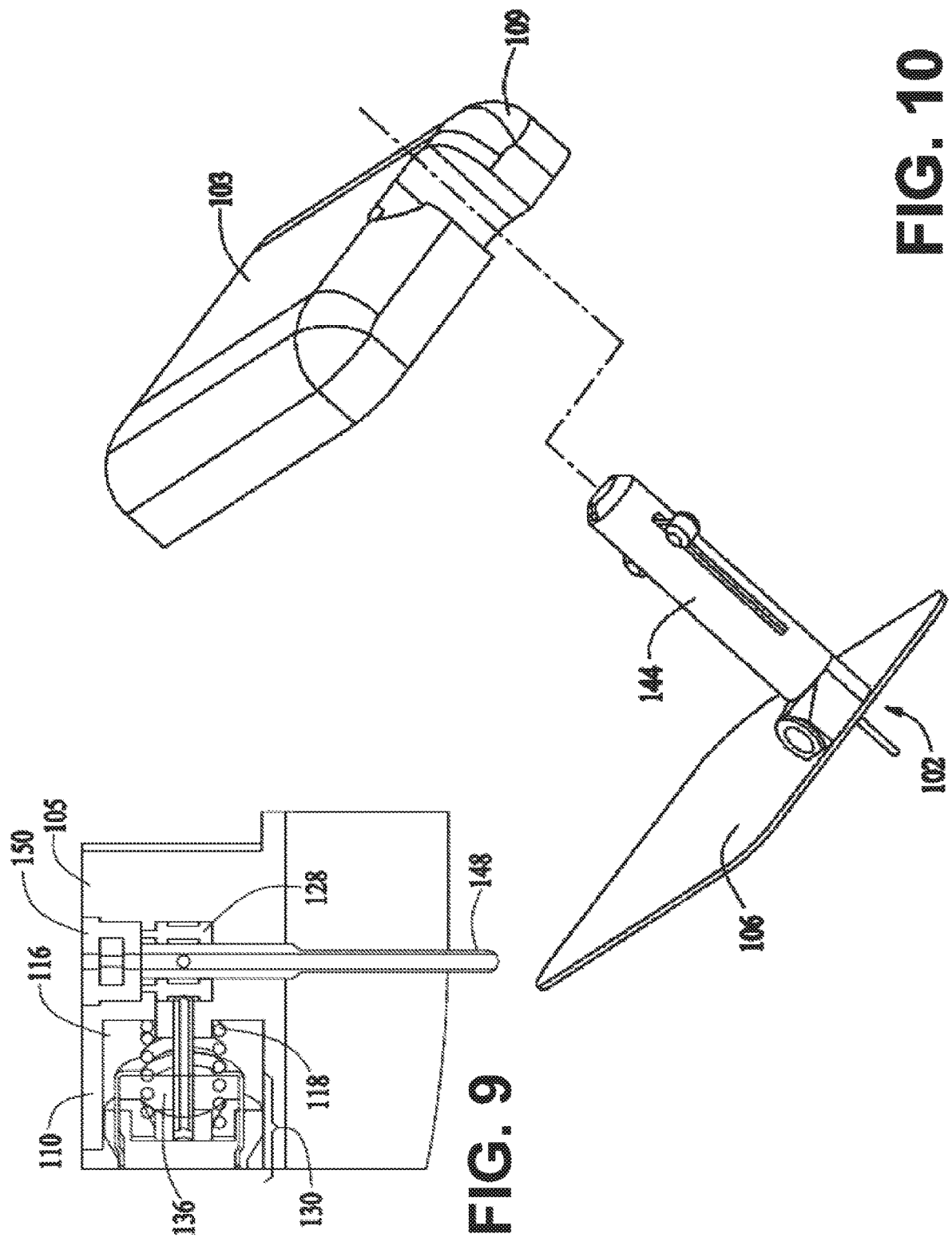

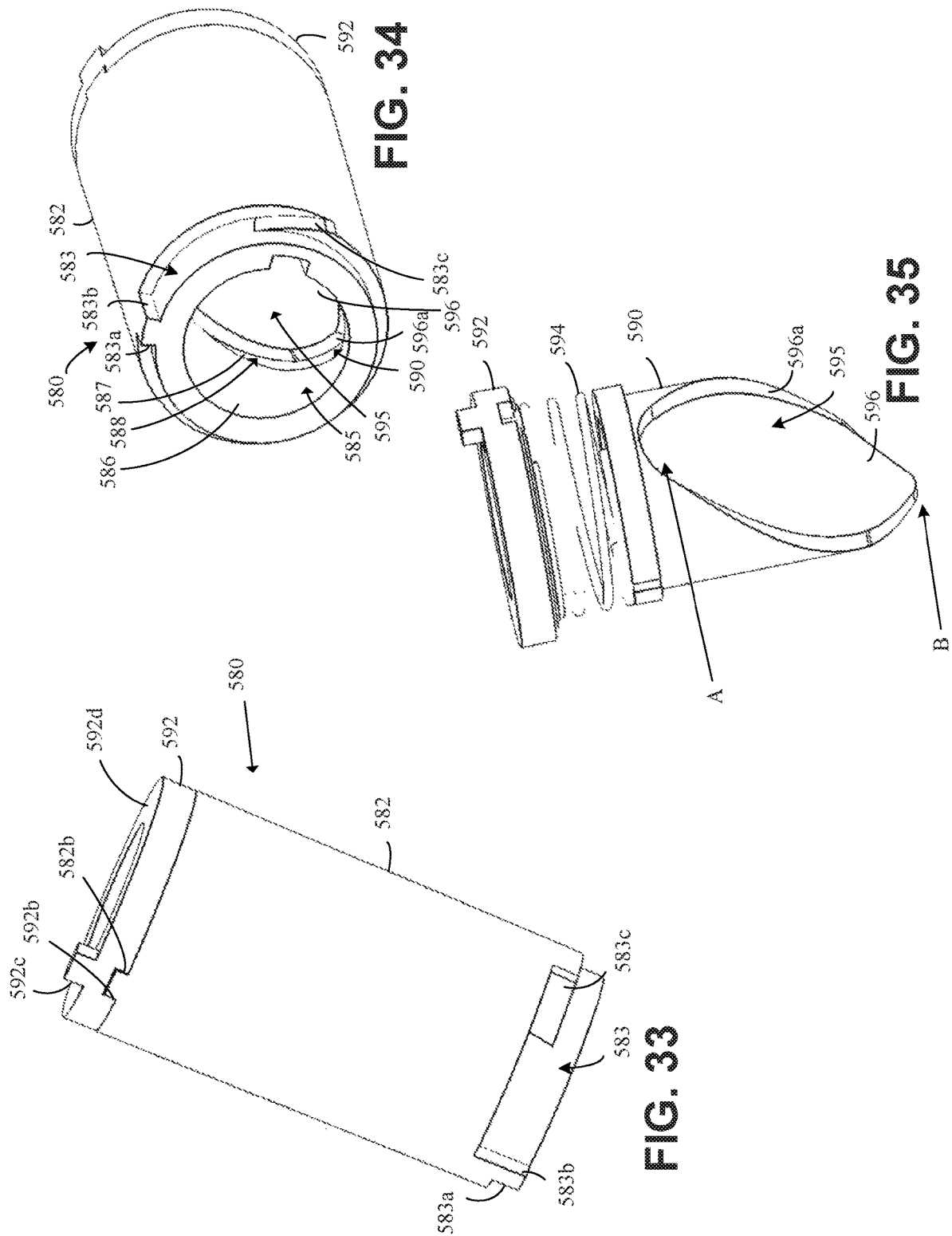

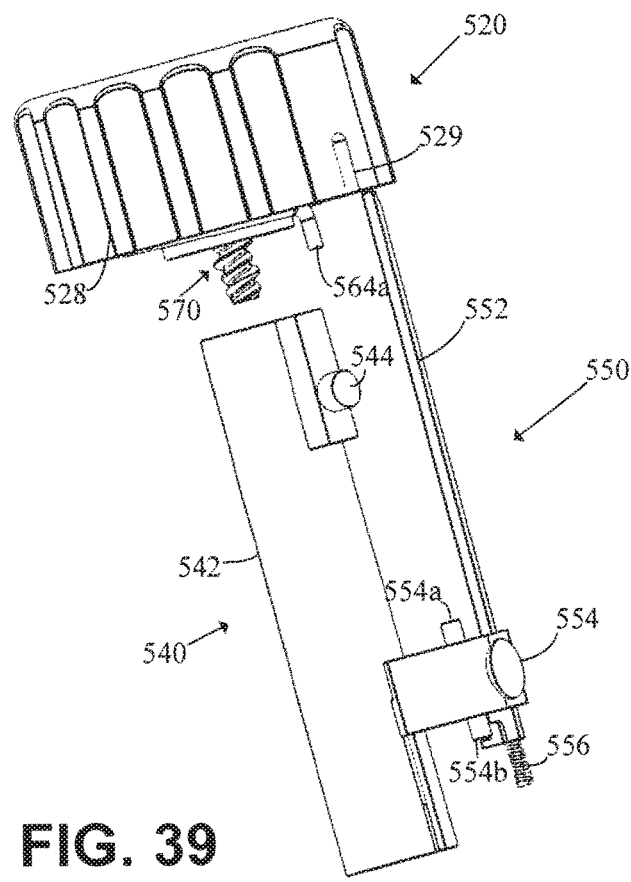
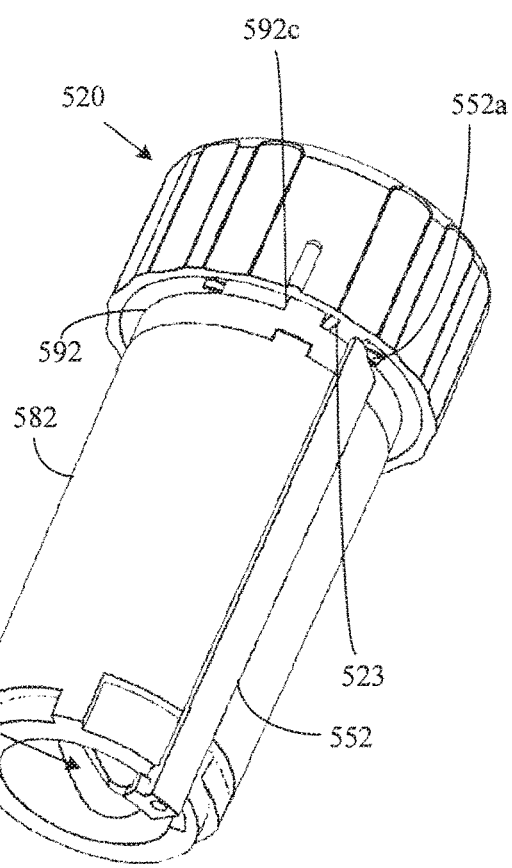
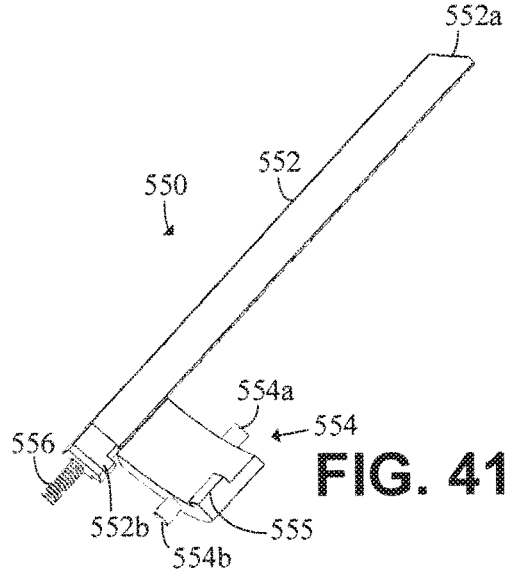
FIG. 39
FIG. 40
FIG. 41

INSERTION DEVICE SYSTEMS AND METHODS

CROSS-REFERENCE TO RELATED PATENT APPLICATIONS

This application is a Continuation of U.S. patent application Ser. No. 15/908,736, filed Feb. 28, 2018, which is a Divisional of U.S. patent application Ser. No. 14/594,014, filed Jan. 9, 2015, U.S. Pat. No. 9,943,332, granted Apr. 17, 2018, which is a Divisional of U.S. patent application Ser. No. 13/015,051, filed Jan. 27, 2011, U.S. Pat. No. 8,932,256, granted Jan. 13, 2015, which is a Continuation-In-Part of U.S. patent application Ser. No. 12/553,038, filed Sep. 2, 2009, U.S. Pat. No. 8,900,190, granted Dec. 2, 2014, each of which are incorporated herein by reference in its entirety.

BACKGROUND

1. Field of the Invention

Embodiments of the present invention generally relate to insertion device systems and methods, and, in specific embodiments, to insertion device systems and methods for insertion into a patient.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, or the like, and further include devices configured for ambulatory or portable use, such as devices designed to be carried by a patient, or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety. Further examples of various insertion tools are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

An insertion system in accordance with an embodiment of the present invention may include, but is not limited to, a base, a first device housing, and a second device housing. The base may be adapted to be carried by a patient. The first device housing may be configured to be operatively engaged with and disengaged from the base. The first device housing may include, but is not limited to a first carrier body. The first carrier body may be arranged for movement within at least a portion of the first device housing at least between a retracted position and an advanced position. The first carrier body may be for supporting a piercing member in a position orientated for insertion through skin of the patient upon movement of the first carrier body from the retracted position to the advanced position.

The second device housing may be configured to be operatively engaged with and disengaged from the first device housing. The second device housing may include, but is not limited to, a second carrier body and a drive mechanism. The second carrier body may be arranged for movement within at least a portion of the second device housing at least between a retracted position and an advanced position. The second carrier body may be operatively engageable with the first carrier body. The drive mechanism may be arranged within the second device housing for providing a rotational force to cause the first carrier body to move from the retracted position toward the advanced position to insert at least a portion of the piercing member through skin of the patient.

In various embodiments, the drive mechanism may comprise a torsion spring member. In various embodiments, the insertion system may include a cam assembly. The cam assembly may be operatively connected with the drive mechanism. The cam assembly may be rotatable at least between a first orientation and a second orientation. The cam assembly may be configured to move the second carrier body toward the advanced position as the cam assembly rotates from the second orientation to the first orientation. The cam assembly may be configured to move the second carrier body toward the retracted position as the cam assembly rotates from the first orientation to the second orientation.

In some embodiments, the cam assembly may have a groove. The second carrier body may have a protrusion arranged for movement along the groove of the cam assembly. The cam assembly may be configured to guide the protrusion along the groove of the cam assembly as the cam assembly rotates between the second orientation and the first orientation to move the second carrier body between the retracted position and the advanced position.

In further embodiments, the cam assembly may be configured to guide the protrusion along the groove of the cam assembly as the cam assembly rotates between the first orientation and the second orientation to move the second carrier body between the advanced position and the retracted position.

In further embodiments, the cam assembly may be configured to guide the protrusion along the groove of the cam assembly as the cam assembly rotates between the second orientation and the first orientation to move the second carrier body between the retracted position and the advanced position. In some embodiments, the drive mechanism may have a first setting and a second setting, the drive mechanism biased toward the first setting in a case where the drive mechanism is in the second setting.

In further embodiments, the drive mechanism may be configured to rotate the cam assembly to the first orientation to move the second carrier body to the advanced position as the drive mechanism is returned to the first setting. In further embodiments, the drive mechanism may be configured to rotate the cam assembly to the second orientation to move the second carrier body to the retracted position as the drive mechanism is set to the second setting.

In further embodiments, the insertion system may further include an adjustment member. The adjustment member may be for setting the drive mechanism to the second setting. In yet further embodiments, the adjustment member may be configured to rotate the cam assembly to the second orientation. The cam assembly may be operatively connected to the drive mechanism such that rotation of the cam assembly to the second orientation sets the drive mechanism to the second setting.

In some embodiments, the insertion system may further include a locking mechanism. The locking mechanism may be adapted to operatively engage and disengage from the cam assembly. The locking mechanism may be configured to substantially prevent rotation of the cam assembly in a case where the locking mechanism is engaged with the cam assembly.

In further embodiments, the locking mechanism may comprise a trigger member. At least one of the trigger member and the cam assembly may have a tab for engaging and disengaging from an aperture in the other of the at least one of the trigger and the cam assembly. The locking mechanism may be configured to substantially prevent rotation of the cam assembly in a case where the tab is engaged with the aperture.

In various embodiments, the drive mechanism may be arranged within the second device housing to move the second carrier body from the retracted position toward the advanced position to move the first carrier body from the retracted position toward the advanced positioned to insert at least a portion of the piercing member through skin of the patient. In various embodiments, the first carrier body may be configured to operatively engage the base when the first carrier body is moved to the advanced position. In various embodiments, the first carrier body may comprise a plunger configured to support the piercing member, and to insert the piercing member in the skin of the user-patient upon movement of the first carrier body from the retracted position to the advanced position.

In various embodiments, a distance traveled by the first carrier body relative to the first device housing from the retracted position to the advanced position may be equal to at least a distance traveled by the second carrier body relative to the second device housing from the retracted position to the advanced position. In various embodiments, a distance traveled by the first carrier body relative to the first device housing from the retracted position to the advanced position may be equal to at least a distance required to insert the piercing member into the skin of the patient.

In various embodiments, the first carrier body may comprise a plunger and a collar body operatively connected to the plunger. The piercing member may be supported by at least one of the plunger and the collar body in a position orientated for insertion through the skin of the patient upon movement of the first carrier body from the retracted position to the advanced position.

In some embodiments, the piercing member may comprise a cannula supported by the collar body and a needle supported by the plunger. The needle may be disposed at least partially through the cannula. The cannula and the needle may be supported in a position orientated for insertion through the skin of the patient upon movement of the first carrier body from the retracted position to the advanced position.

In further embodiments, the plunger and the needle may be removable from the collar body. The cannula and the collar body may be adapted for reuse with another collar body and cannula. In further embodiments, the collar body may have a fluid channel in fluid communication with a hollow interior of the cannula. The fluid channel may be for operatively connecting to a reservoir for containing fluidic media when the first carrier body is in the advanced position to allow fluidic medic to flow from the reservoir to the hollow interior of the cannula.

In various embodiments, the piercing member may comprise a needle. In various embodiments, the second carrier body may be configured to operatively connect with at least two different types of piercing members. The second carrier body may be configured to insert at least a portion of a selected one of the at least two different types of piercing members in a case where the selected one of the at least two different types of piercing members is operatively connected to the second carrier body and the second carrier body is moved to the advanced position.

In some embodiments, the second carrier body may be configured to be removable from the selected one of the at least two different types of piercing members and adapted for reuse with another one of the at least two different types of piercing members. In some embodiments, the insertion system may be removable from the selected one of the at least two different types of piercing members. In further embodiments, the insertion system may be completely removable from the selected one of the at least two different types of piercing members.

In some embodiments, the piercing member may be supported by the first carrier body is one of the at least two different types of piercing members. In some embodiments, the selected one of the at least two different types of piercing members may be an insertion needle of an insertion set.

In some embodiments, the selected one of the at least two different types of piercing members may be a lancet for obtaining a fluid sample from the patient. In further embodiments, the insertion system may further include a guard. The guard may be configured to be removably attachable to the second device housing. The guard may have an aperture for allowing the lancet to extend through in a case where the lancet is operatively connected to the second carrier body and the second carrier body is moved to the advanced position.

In some embodiments, a distance traveled by the first carrier body relative to the first device housing from the retracted position to the advanced position may be equal to at least a distance required to insert the selected one of the at least two different types of piercing members in the skin of the patient that is at least equal to an implantable length of the selected one of the at least two different types of piercing members.

In various embodiments, at least one of the first device housing and the second device housing may have a magnet, and the other of the at least one of the first device housing and the second device housing may have an attractive element for interacting with the magnet to connect the first device housing and the second device housing.

In some embodiments, at least one of the first carrier body and the second carrier body may have a magnet, and the other of the at least one of the first carrier body and the second carrier body may have an attractive element for interacting with the magnet to connect the first carrier body and the second carrier body. In some embodiments, the attractive element may comprise one of a ferrous material and a magnet.

In various embodiments, the first device housing may have a section for supporting a portion of the first carrier body and for preventing the first carrier body from moving to the advanced position, the section may be moveable relative to the first carrier body. The second device housing may be configured to cause movement of the section of the first device housing to provide sufficient clearance to allow the first carrier body to move to the advanced position in a case where the first carrier body is moved by the second carrier body.

In some embodiments, the second device housing may have a portion for operatively engaging the section of the first device housing to cause movement of the section of the first device housing in a case where the second device housing is operatively connected with the first device housing and the second device housing is rotated relative to the first device housing.

A method of manufacturing an insertion system may include, but is not limited to, any one of or combination of: (i) adapting a base to be carried by a patient; configuring a first device housing to be operatively engaged with and disengaged from the base, configuring the first device housing comprising: arranging a first carrier body for movement within at least a portion of the first device housing at least between a retracted position and an advanced position, the first carrier body for supporting a piercing member in a position orientated for insertion through skin of the patient upon movement of the first carrier body from the retracted position to the advanced position; and (iii) configuring a second device housing to be operatively engaged with and disengaged from the first device housing, configuring the second device housing comprising: (a) arranging a second carrier body for movement within at least a portion of the second device housing at least between a retracted position and an advanced position, the second carrier body operatively engageable with the first carrier body; and (b) arranging a drive mechanism within the second device housing for providing a rotational force to cause the first carrier body to move from the retracted position toward the advanced position to insert at least a portion of the piercing member through skin of the patient.

An insertion system, the insertion system may include a device housing. The device housing may be configured to be operatively engaged with and disengaged from a base adapted to be carried by a patient. The device housing may be engageable with an actuation device. The device housing may include, but is not limited to, a carrier body. The carrier body may be arranged for movement within at least a portion of the device housing at least between a retracted position and an advanced position. The carrier body may be for supporting a piercing member in a position orientated for insertion through skin of the patient upon movement of the carrier body from the retracted position to the advanced position. The carrier body may be operatively engageable with a moveable carrier body of the actuation device so that the carrier body of the device housing moved by the carrier body of the actuation device at least between the retracted position and the advanced position.

The device housing may have a section for supporting a portion of the carrier body of the device housing and for preventing the carrier body of the device housing from moving to the advanced position. The section may be moveable relative to the carrier body of the device housing to provide sufficient clearance to allow the carrier body of the device housing to move to the advanced position in a case where the carrier body of the device housing is moved by the carrier body of the actuation device.

In various embodiments, the system may further include the actuation device. The actuation device may be configured to be operatively engaged with and disengaged from the device housing. The carrier body of the actuation device may be arranged for movement within at least a portion of the actuation device at least between a retracted position and an advanced position. The carrier body of the actuation device may be operatively engageable with the carrier body of the device housing.

In some embodiments, the system may further include a drive mechanism. The drive mechanism may be arranged within the actuation device to move the carrier body of the device housing from the retracted position toward the advanced position to insert at least a portion of the piercing member through skin of the patient. In further embodiments, the drive mechanism may be configured to provide a rotational force to cause the carrier body of the device housing to move from the retracted position toward the advanced position to insert at least a portion of the piercing member through skin of the patient.

In some embodiments, the actuation device may be configured to cause movement of the section of the device housing to provide sufficient clearance to allow the carrier body of the device housing to move to the advanced position in a case where the carrier body of the device housing is moved by the carrier body of the actuation device.

In various embodiments, at least one of the device housing and the actuation device may have a magnet, and the other of the at least one of the device housing and the actuation device may have an attractive element for interacting with the magnet to connect the device housing and the actuation device.

In some embodiments, at least one of the carrier body of the device housing and the carrier body of the actuation device may have a magnet, and the other of the at least one of the carrier body of the device housing and the carrier body of the actuation device may have an attractive element for interacting with the magnet to connect the carrier body of the device housing and the carrier body of the actuation device. In some embodiments, the attractive element may comprise one of a ferrous material and a magnet.

In various embodiments, the device housing may further include an engagement member. The engagement member may be engageable with and disengageable from the base to operatively engage and disengage the device housing and the base. At least one of the base and the engagement member may be configured such that the engagement member is prevented from engaging the base in a case where the engagement member has been disengaged from the base unless a second force having a magnitude equal to or greater than the first force is applied to the engagement member.

In various embodiments, the piercing member may comprise a needle. In various embodiments, the carrier body of the device housing may comprise a plunger configured to support the piercing member, and to insert the piercing member in the skin of the user-patient upon movement of the carrier body of the device housing from the retracted position to the advanced position. In various embodiments, a distance traveled by the carrier body of the device housing relative to the device housing from the retracted position to the advanced position may be equal to at least a distance required to insert the piercing member into the skin of the patient.

In various embodiments, the carrier body of the device housing may comprise a plunger and a collar body operatively connected to the plunger. The piercing member may be supported by at least one of the plunger and the collar body in a position orientated for insertion through the skin of the patient upon movement of the carrier body of the device housing from the retracted position to the advanced position.

In some embodiments, the piercing member may comprise a cannula supported by the collar body and a needle supported by the plunger. The needle may be disposed at least partially through the cannula. The cannula and the needle may be supported in a position orientated for insertion through the skin of the patient upon movement of the carrier body of the device housing from the retracted position to the advanced position.

In further embodiments, the plunger and the needle may be removable from the collar body. The cannula and the collar body may be adapted for reuse with another collar body and cannula. In further embodiments, the collar body may have a fluid channel in fluid communication with a hollow interior of the cannula; the fluid channel may be for operatively connecting to a reservoir for containing fluidic media when the carrier body of the device housing is in the advanced position to allow fluidic medic to flow from the reservoir to the hollow interior of the cannula.

A method of manufacturing an insertion system may include, but is not limited to, any one of or combination of: (i) configuring a device housing configured to be operatively engaged with and disengaged from a base adapted to be carried by a patient, the device housing engageable with an actuation device, configuring the device housing comprising: arranging a carrier body for movement within at least a portion of the device housing at least between a retracted position and an advanced position, the carrier body for supporting a piercing member in a position orientated for insertion through skin of the patient upon movement of the carrier body from the retracted position to the advanced position, the carrier body operatively engageable with a moveable carrier body of the actuation device so that the carrier body of the device housing moved by the carrier body of the actuation device at least between the retracted position and the advanced position; and (ii) arranging a section of the device housing to support a portion of the carrier body of the device housing and for preventing the carrier body of the device housing from moving to the advanced position, the section moveable relative to the carrier body of the device housing to provide sufficient clearance to allow the carrier body of the device housing to move to the advanced position in a case where the carrier body of the device housing is moved by the carrier body of the actuation device.

An insertion system may include, but is not limited to, a base, a device housing, and an engagement member. The base may be adapted to be carried by a patient. The device housing may be configured to be operatively engaged with and disengaged from the base. The device housing may be engageable with an actuation device. The device housing may include, but is not limited to, a carrier body and an engagement member. The carrier body may be arranged for movement within at least a portion of the device housing at least between a retracted position and an advanced position, the carrier body for supporting a piercing member in a position orientated for insertion through skin of the patient upon movement of the carrier body from the retracted position to the advanced position. The carrier body may be operatively engageable with a moveable carrier body of the actuation device so that the carrier body of the device housing moved by the carrier body of the actuation device at least between the retracted position and the advanced position.

The engagement member may be engageable with and disengageable from the base to operatively engage and disengage the device housing and the base. The engagement member may be configured to engage the base in a case where a first force of at least a particular magnitude is applied to the engagement member. At least one of the base and the engagement member may be configured such that the engagement member is prevented from engaging the base in a case where the engagement member has been disengaged from the base unless a second force having a magnitude equal to or greater than the first force is applied to the engagement member.

In various embodiments, at least one of the base and the engagement member may have a reengagement prevention member for preventing the engagement member from engaging the base in a case where the engagement member has been disengaged from the based unless the second force is applied to the engagement member. In some embodiments, the reengagement prevention member may comprise an abutment of the engagement member. The abutment may be for preventing the engagement member from engaging the base in a case where the engagement member has been disengaged from the based unless the second force is applied to the engagement member.

In some embodiments, the engagement member may be engageable with and disengageable from an aperture of the base to operatively engage and disengage the device housing and the base. The at least one of the base and the engagement member may have a reengagement prevention member comprises an abutment of the engagement member. The abutment may be for preventing the engagement member from engaging the base in a case where the engagement member has been disengaged from the based.

In various embodiments, the engagement member may be engageable with and disengageable from an aperture of the base to operatively engage and disengage the device housing and the base. In various embodiments, the engagement member may be a lever. In various embodiments, the piercing member may comprise a needle.

In various embodiments, the carrier body of the device housing may comprise a plunger configured to support the piercing member, and to insert the piercing member in the skin of the user-patient upon movement of the carrier body of the device housing from the retracted position to the advanced position. In various embodiments, a distance traveled by the carrier body of the device housing relative to the device housing from the retracted position to the advanced position may be equal to at least a distance required to insert the piercing member into the skin of the patient.

In various embodiments, the carrier body of the device housing may comprise a plunger and a collar body operatively connected to the plunger. The piercing member may be supported by at least one of the plunger and the collar body in a position orientated for insertion through the skin of the patient upon movement of the carrier body of the device housing from the retracted position to the advanced position.

In some embodiments, the piercing member may comprise a cannula supported by the collar body and a needle supported by the plunger. The needle may be disposed at least partially through the cannula. The cannula and the needle may be supported in a position orientated for insertion through the skin of the patient upon movement of the carrier body of the device housing from the retracted position to the advanced position.

In further embodiments, the plunger and the needle may be removable from the collar body. The cannula and the collar body may be adapted for reuse with another collar body and cannula. In further embodiments, the collar body may have a fluid channel in fluid communication with a hollow interior of the cannula. The fluid channel may be for operatively connecting to a reservoir for containing fluidic media when the carrier body of the device housing is in the advanced position to allow fluidic medic to flow from the reservoir to the hollow interior of the cannula.

A method of manufacturing an insertion system may include, but is not limited to, any one of or combination of: (i) adapting a base to be carried by a patient; (ii) configuring a device housing to be operatively engaged with and disengaged from the base, the device housing engageable with an actuation device, configuring the device housing comprising: arranging a carrier body for movement within at least a portion of the device housing at least between a retracted position and an advanced position, the carrier body for supporting a piercing member in a position orientated for insertion through skin of the patient upon movement of the carrier body from the retracted position to the advanced position, the carrier body operatively engageable with a moveable carrier body of the actuation device so that the carrier body of the device housing moved by the carrier body of the actuation device at least between the retracted position and the advanced position; (iii) providing an engagement member engageable with and disengageable from the base to operatively engage and disengage the device housing and the base, the engagement member configured to engage the base in a case where a first force of at least a particular magnitude is applied to the engagement member; and (iv) configuring at least one of the base and the engagement member such that the engagement member is prevented from engaging the base in a case where the engagement member has been disengaged from the base unless a second force having a magnitude equal to or greater than the first force is applied to the engagement member.

An insertion detection system may include, but is not limited to, a base, a housing, a pair of interactive elements, and circuitry. The base may be adapted to be carried by a patient. The housing may be attached to the base. The housing may have a fluid connector arranged for movement relative to the base. The pair of interactive elements may include a first interactive element supported on the base and a second interactive element supported on the housing at a location to be interactable with the first interactive element when the fluid connector is moved to a predetermined position. The circuitry may be configured to detect an interaction between the first interactive element and the second interactive element when the fluid connector is in the predetermined position. The circuitry may be configured to provide a signal or a change in state in response to detecting the interaction between the first interactive element and the second interactive element.

In some embodiments, the housing may include a carrier body arranged for movement within at least a portion of the housing at least between a retracted position and an advanced position. The carrier body may be for supporting the fluid connector in a position orientated for insertion through skin of the patient upon movement of the carrier body from the retracted position to the advanced position. The second interactive element may be supported on the carrier body.

In further embodiments, the housing may be configured to be operatively engaged to an actuation device for selectively moving the carrier body from the retracted position toward the advanced position to insert at least a portion of the fluid connector through skin of the patient.

In further embodiments, the fluid connector may be in the predetermined position when the carrier body is in the advanced position so that the fluid connector is inserted through the skin of the patient.

In yet further embodiments, the fluid connector may be in the predetermined position when the carrier body is in the advanced position so that the fluid connector is inserted in the skin of the patient a defined depth.

In further embodiments, the fluid connector may be in the predetermined position when the carrier body is in the advanced position so that the first interactive element and the second interactive element are sufficiently proximate to each other.

In some embodiments, the fluid connector may be in the predetermined position when the first interactive element and the second interactive element are sufficiently proximate to each other.

In further embodiments, the first interactive element and the second interactive element may be sufficiently proximate to each other in a case where the first interactive element and the second interactive element contact each other.

In some embodiments, the fluid connector may be in the predetermined position when the fluid connector is in fluid communication with a fluid path of the base.

In some embodiments, the fluid connector may comprise at least one of a cannula and a needle.

In some embodiments, the system may further include a user-perceptible indicator operatively connected to the circuitry. The user-perceptible indicator may be for providing a user-perceptible indication in response to the signal or the change in state by the circuitry.

In further embodiments, the user-perceptible indication may comprise at least one of an audible indication, a visual indication, and a tactile indication.

In some embodiments, the first interactive element and the second interactive element may be configured to be electronically interactable with each other.

In some embodiments, one of the base and the housing may support a reservoir having an interior volume for containing fluidic media and a plunger head moveable within the interior volume of the reservoir along an axial direction of the reservoir. The system may further include a drive device and control electronics. The drive device may be supported by the other of the base and the housing relative to the one of the base and the housing supporting the reservoir. The control electronics may be operatively connected to the circuitry for controlling the drive device to drive fluid from the reservoir based upon the signal or the state provided by the circuitry.

In further embodiments, the control electronics may be configured to inhibit operation of the drive device unless a signal or a state provided by the circuitry corresponds to the signal or the state provided by the circuitry when detecting the interaction between the first interactive element and the second interactive element.

In further embodiments, the control electronics may be configured to change from a first power state to a second power state in response to detecting the interaction between the first interactive element and the second interactive element.

In further embodiments, the fluid connector may comprise the reservoir.

In some embodiments, the first interactive element may comprise a detectable feature. The second interactive element may comprise a sensor configured to sense the detectable feature when the fluid connector is moved to the predetermined position. The circuitry may be configured to provide the signal or the change in state in a case where the detectable feature is detected by the sensor.

In further embodiments, the sensor may comprise at least one magnetic sensor. The detectable feature may comprise a magnetic material.

In some embodiments, one of the first interactive element and the second interactive element may have a capacitance that is measurable. The other of the one of the first interactive element and the second interactive element may be configured to affect the capacitance when the fluid connector is in the predetermined position. The circuitry may be configured to provide the signal or the change in state when the capacitance is affected by the other of the one of the first interactive element and the second interactive element.

In some embodiments, one of the first interactive element and the second interactive element may have an inductance that is measurable. The other of the one of the first interactive element and the second interactive element may be configured to affect the inductance when the fluid connector is in the predetermined position. The circuitry may be configured to provide the signal or the change in state when the inductance is affected by the other of the one of the first interactive element and the second interactive element.

In some embodiments, the housing may be configured to be operatively engaged with and disengaged from the base.

In some embodiments, the housing may be integral with the base.

In some embodiments, one of the first interactive element and the second interactive element may include data or information. The other of the one of the first interactive element and the second interactive element is configured to access the data or information of the one of the first interactive element and the second interactive element when the first element and the second element interact.

In further embodiments, the circuitry may be configured to provide a signal or a change in state based on the data or information accessed by the other of the one of the first interactive element and the second interactive element.

In some embodiments, the fluid connector may include data or information. One of the first interactive element and the second interactive element may be configured to access the data or information when the first element and the second element interact.

A method of manufacturing an insertion detection system may include, but is not limited to, any one or combination of: (i) adapting a base to be carried by a patient; (ii) arranging a housing on the base, the housing having a fluid connector arranged for movement relative to the base; (iii) providing a pair of interactive elements including a first interactive element supported on the base and a second interactive element supported on the housing at a location to be interactable with the first interactive element when the fluid connector is moved to a predetermined position; and (iv) configuring circuitry to detect an interaction between the first interactive element and the second interactive element when the fluid connector is in the predetermined position, the circuitry configured to provide a signal or a change in state in response to detecting the interaction between the first interactive element and the second interactive element.

An insertion detection system may include, but is not limited to, a base, a housing, a carrier body, a pair of interactive elements, and circuitry. The base may be adapted to be carried by a patient. The housing may be attached to the base. The carrier body may be arranged for movement within at least a portion of the housing at least between a retracted position and an advanced position. The carrier body may be for supporting a piercing member in a position orientated for insertion through skin of the patient upon movement of the carrier body from the retracted position to the advanced position. The pair of interactive elements may include a first interactive element supported on the base and a second interactive element supported on the housing at a location to be interactable with the first interactive element when the fluid connector is positioned in a predetermined position. The circuitry may be configured to detect an interaction between the first interactive element and the second interactive element when the piercing member is positioned in the predetermined position. The circuitry may be configured to provide a signal or a change in state in response to detecting an interaction between the first interactive element and the second interactive element.

BRIEF DESCRIPTION OF THE DRAWINGS

FIG. 9 illustrates a medical device in accordance with an embodiment of the present invention;

FIG. 10 illustrates a medical device in accordance with an embodiment of the present invention;

FIG. 33 illustrates a portion of a medial device in accordance with an embodiment of the present invention;

FIG. 34 illustrates a portion of a medial device in accordance with an embodiment of the present invention;

FIG. 35 illustrates a portion of a medial device in accordance with an embodiment of the present invention;

FIG. 39 illustrates a portion of a medial device in accordance with an embodiment of the present invention;

FIG. 40 illustrates a portion of a medial device in accordance with an embodiment of the present invention;

FIG. 41 illustrates a portion of a medial device in accordance with an embodiment of the present invention;

DETAILED DESCRIPTION OF THE PREFERRED EMBODIMENTS

Figure 1:
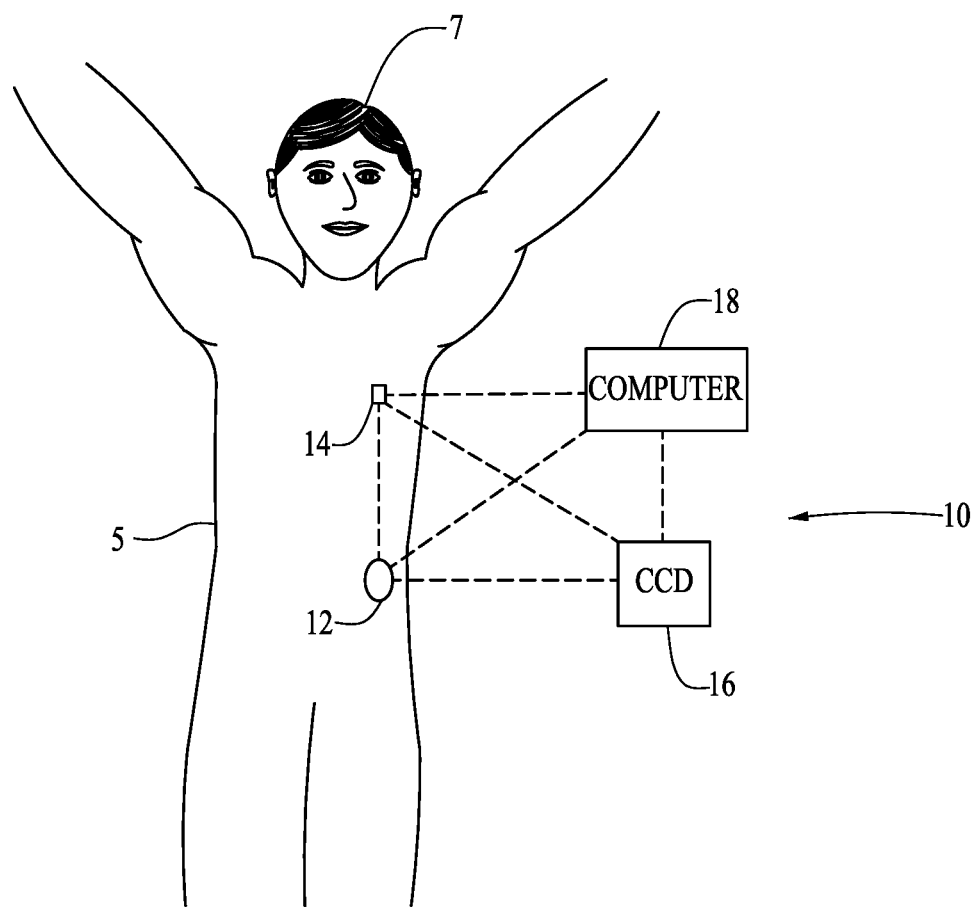
FIG. 1 illustrates a generalized representation of a system in accordance with an embodiment of the present invention.

FIG. 1 illustrates a generalized representation of a system 10 in accordance with an embodiment of the present invention. The system 10 may include a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, the delivery device 12, the sensing device 14, the CCD 16, and computer 18 may be similar to those described in the following U.S. patent applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, Or The Like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional Application Ser. No. 61/044, 269, filed Apr. 11, 2008, "Reservoir Plunger Head Systems And Methods"; (xxxvii) U.S. Patent Application Ser. No. 61/044,292, filed Apr. 11, 2008, "Reservoir Barrier Layer Systems And Methods"; (xxxviii) U.S. Patent Provisional Application Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; (liii) U.S. patent application Ser. No. 12/360,813, filed Jan. 27, 2009, "Multi-Position Infusion Set Device And Process"; (liv) U.S. Patent Pub. No. US 2007/0142776 (application Ser. No. 10/314,653), filed Dec. 9, 2002, "Insertion Device For An Insertion Set and Methods Of Using The Same." In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, or the like. In some embodiments, fluidic media may include a nutritional supplement, a dye, a tracing medium, a saline medium, a hydration medium, or the like.

The sensing device 14 may include a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
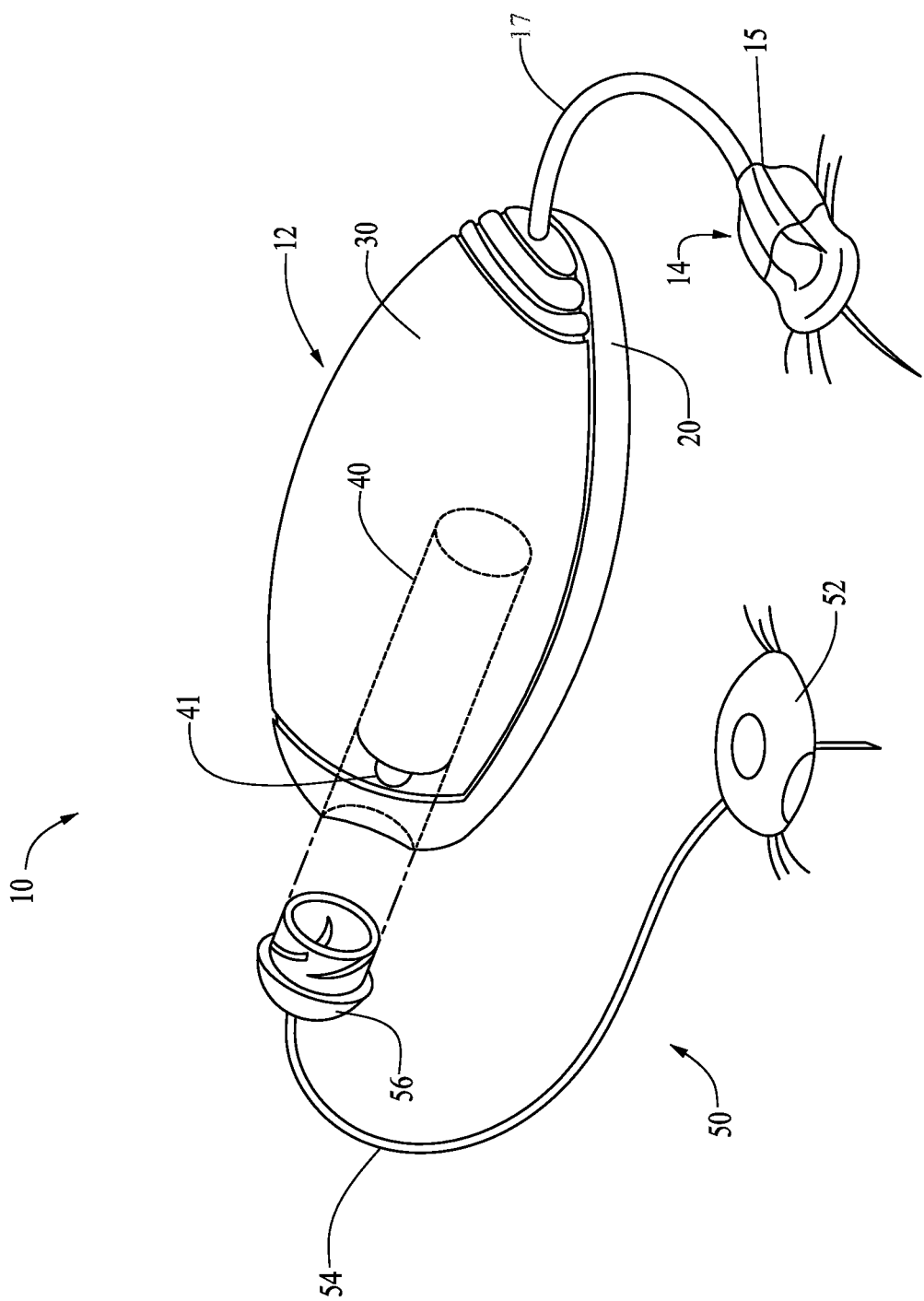
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention may include a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 may support the reservoir system 40 and has a bottom surface (facing downward and into the page in FIG. 2) configured to secure to the body of the user-patient. An adhesive may be employed at an interface between the bottom surface of the disposable housing 20 and the skin of the user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12, and delivery devices in general, may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 may be configured for containing or holding fluidic media, such as, but not limited to insulin. In various embodiments, the reservoir system 40 may include a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 may include at least one port 41 for allowing fluidic media to flow into and/or flow out of the interior volume of the reservoir system 40. In some embodiments, the infusion path 50 may include a connector 56, a tube 54, and a needle apparatus 52. The connector 56 of the infusion path 50 may be connectable to the port 41 of the reservoir system 40. In various embodiments, the disposable housing 20 may be configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 may be covered with or supports a septum (not shown in FIG. 2), such as a self-sealing septum, or the like. The septum may be configured to prevent fluidic media from flowing out of the reservoir system 40 through the port 41 when the septum is not pierced. In addition, in various embodiments, the connector 56 of the infusion path 50 may include a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, or the like may be used. In various embodiments, the needle apparatus 52 of the infusion path 50 may include a needle that is able to puncture the skin of the user-patient. In addition, in various embodiments, the tube 54 connects the connector 56 with the needle apparatus 52 and may be hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features that allow the two parts to connect together easily, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same," which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set," which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 may include a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (un-used) disposable housing 20 for further delivery operation with a user-patient.

Figure 3:
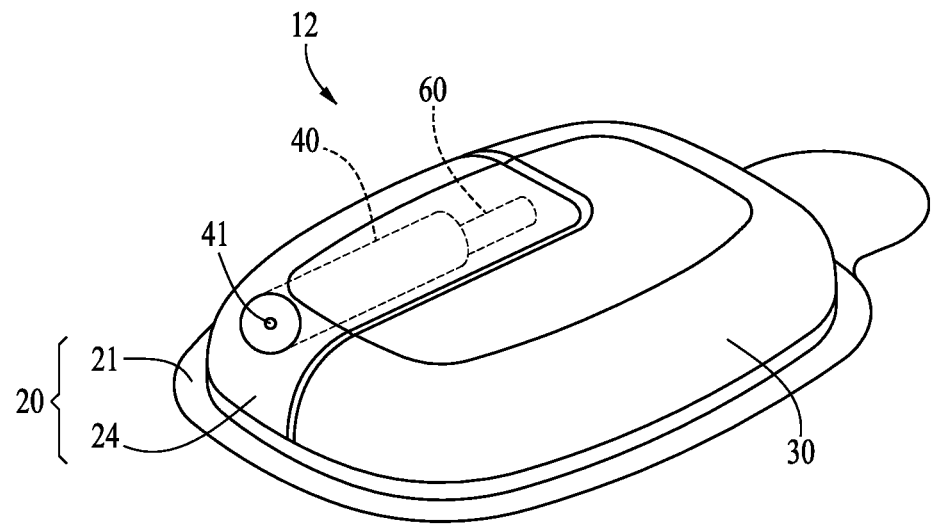
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 may be configured to be securable to a body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
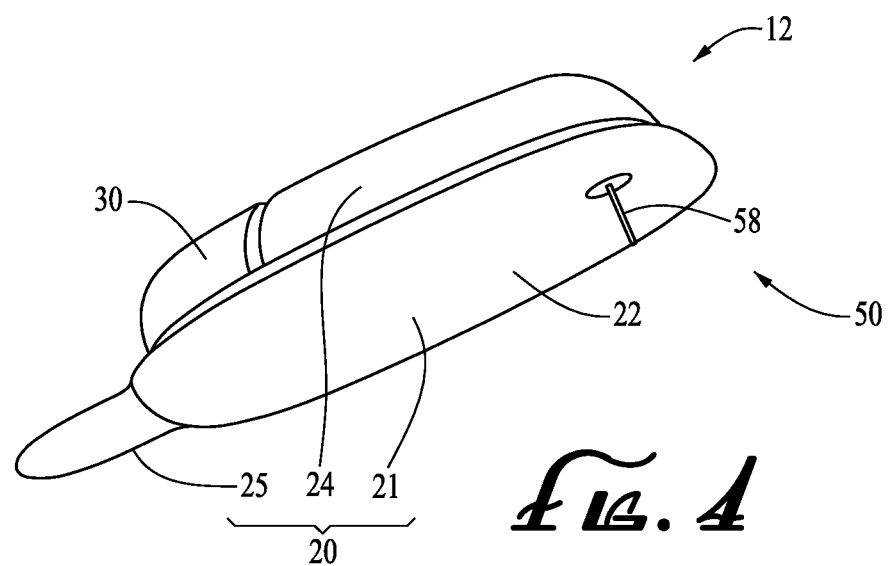
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
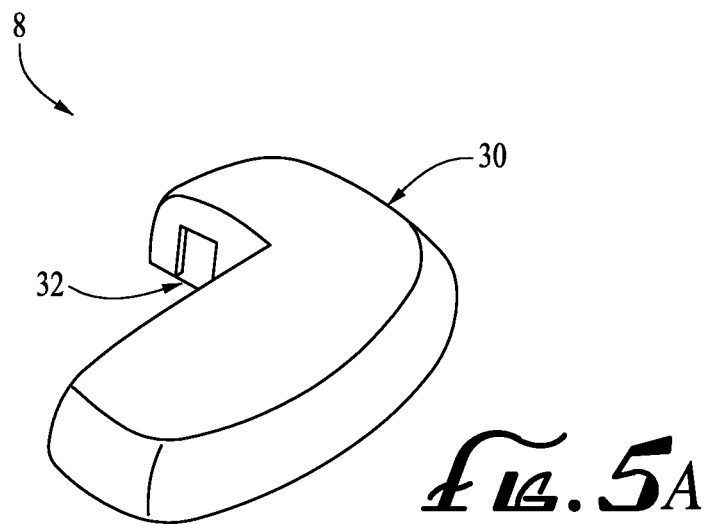
FIG. 5A illustrates a durable portion of a delivery device in accordance with an embodiment of the present invention.
Figure 5B:
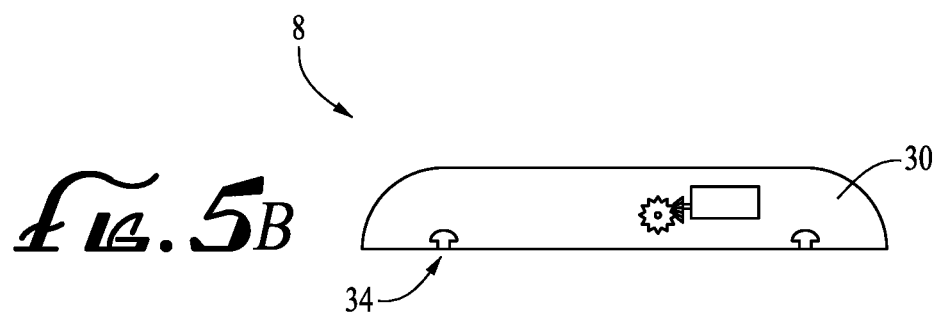
FIG. 5B illustrates a section view of a durable portion of a delivery device in accordance with an embodiment of the present invention.
Figure 5C:
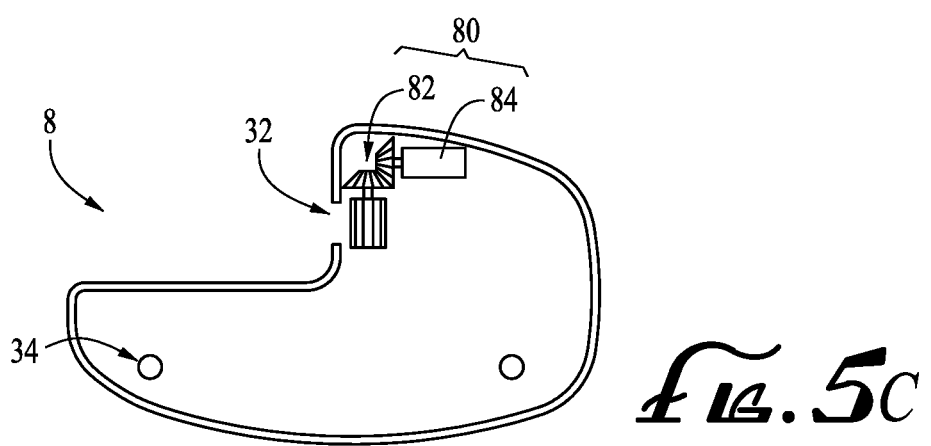
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 may include the durable housing 30, and a drive device 80. The drive device 80 may include a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 may be configured with an opening 32 for receiving a plunger arm 60 (refer to FIG. 3). In addition, in various embodiments, the durable housing 30 may include one or more connection members 34, such as tabs, insertion holes, or the like, for connecting with the base 21 of the disposable housing 20 (refer to FIG. 3).

Figure 6A:
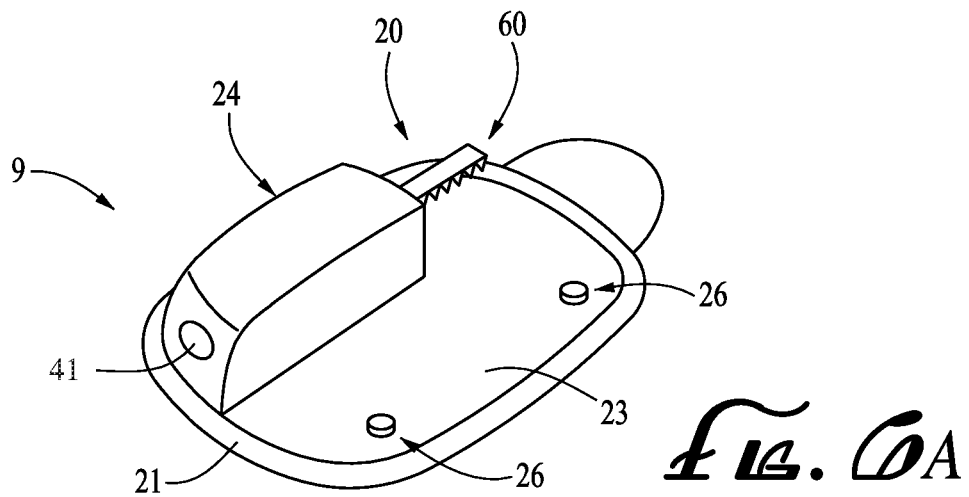
FIG. 6A illustrates a disposable portion of a delivery device in accordance with an embodiment of the present invention.
Figure 6B:
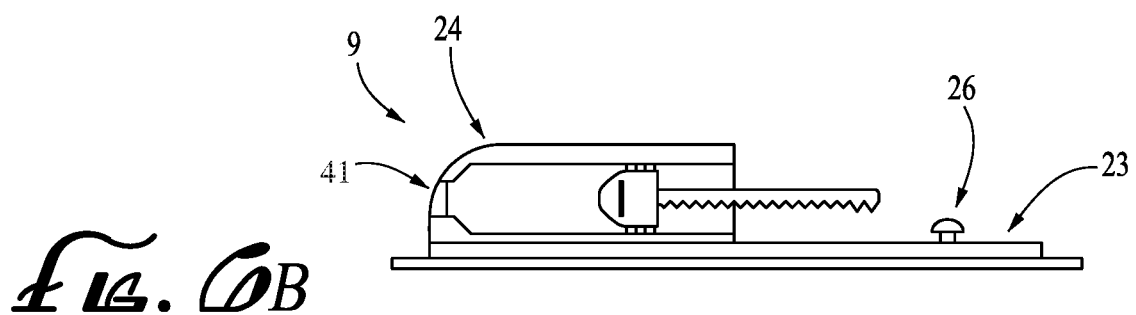
FIG. 6B illustrates a section view of a disposable portion of a delivery device in accordance with an embodiment of the present invention.
Figure 6C:
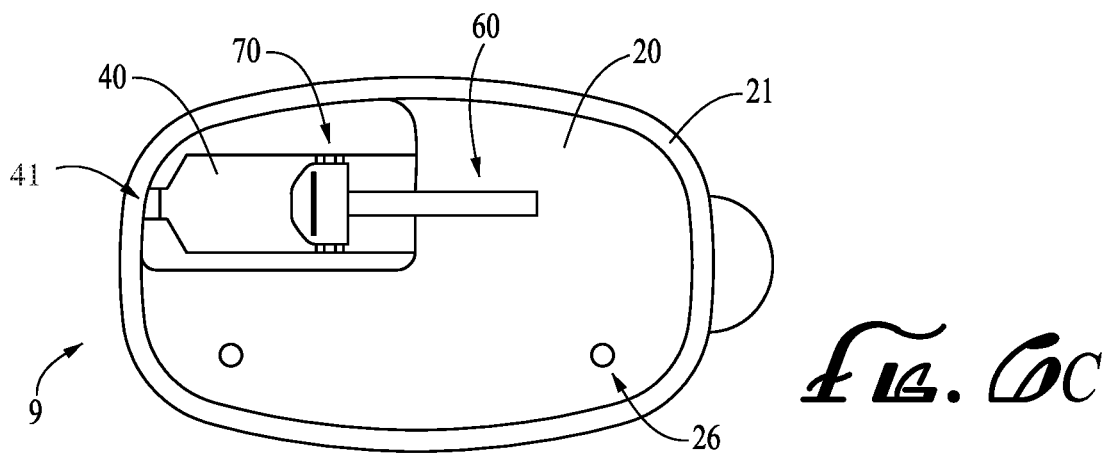
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 may include the base 21 and the reservoir-retaining portion 24. In various embodiments, the base 21 may include a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 may be housed within the reservoir retaining portion 24 of the disposable housing 20, and the reservoir system 40 may be configured to hold fluidic media. In addition, in various embodiments, the plunger head 70 may be disposed at least partially within the reservoir system 40 and may be moveable within the reservoir system 40 to allow fluidic media to fill into the reservoir system 40 and to force fluidic media out of the reservoir system 40. In some embodiments, the plunger arm 60 may be connected to or is connectable to the plunger head 70.

Also, in some embodiments, a portion of the plunger arm 60 may extend to outside of the reservoir-retaining portion 24 of the disposable housing 20. In various embodiments, the plunger arm 60 may have a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, the user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 may include reservoir status circuitry (not shown), and the reservoir system 40 may include reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 may include the reservoir status circuitry (not shown), and the reservoir status circuitry may be configured to read data from the reservoir circuitry (not shown) when the reservoir system 40 is inserted into the disposable portion 9.

In various embodiments, the reservoir status circuitry (not shown) may be further configured to store data to the reservoir circuitry after at least some of the contents of the reservoir system 40 have been transferred out of the reservoir system 40 to update information in the reservoir circuitry (not shown) related to an amount of contents still remaining in the reservoir system 40. In some embodiments, the reservoir status circuitry (not shown) may be configured to store data to the reservoir circuitry (not shown) to update information in the reservoir circuitry (not shown) related to an amount of contents remaining in the reservoir system 40 when the reservoir system 40 is inserted into the disposable portion 9. In some embodiments, the delivery device 12 may include the reservoir status circuitry (not shown) and the reservoir system 40 may include the reservoir circuitry (not shown), and the reservoir status circuitry (not shown) may selectively inhibit use of the delivery device 12 or may selectively provide a warning signal based on information read by the reservoir status circuitry (not shown) from the reservoir circuitry (not shown).

Aspects of the present invention relate, generally, to needle inserter or inserting devices and methods and medical devices, such as, but not limited to sensors, monitors and infusion medium delivery systems, devices and methods that include such needle-inserting devices and methods. The needle-inserting device and method may operate to insert a needle or cannula through skin of a user-patient, for example, to provide a fluid flow path for conveying an infusion medium through a hollow channel in the needle or cannula and into the user-patient and/or to convey a fluid from the user-patient to one or more sensor elements. Embodiments of the present invention may be configured, as described herein, to provide a reliable, cost effective, and easy-to-use mechanism for inserting a needle or cannula to a specific depth into a user-patient with minimal traumatic effect.

In addition, embodiments may be configured to establish a contiguous fluid flow passage for fluid transfer between a reservoir and the user-patient when the hollow needle or cannula is inserted into the user-patient. Needle-inserting devices according to embodiments of the present invention may be used with, connectable to and disconnectable from, or incorporated in a portion of an infusion medium delivery system. For example, a needle-inserting device may be connectable to a base structure of a pump-type delivery device for insertion of a needle, after which the needle-inserting device may be removed from the base structure, whereupon a further housing portion of the delivery device (containing components such as, but not limited to, a reservoir and pump or drive device) may be coupled to the base structure for operation.

Alternatively, the needle-inserting device may be incorporated into the further housing portion that contains other components as described above. In yet other embodiments, the needle-inserting device may be connectable to (and releasable from) or incorporated within an injection site module or other housing that connects, for example, by flexible tubing, to other components of a medical device (such as, but not limited to an infusion medium delivery device). In yet other embodiments, needle inserter devices may be configured for use with systems other than infusion medium delivery systems, such as, but not limited to sensor and monitor systems, or the like.

The structures and methods described with respect to FIGS. 7-25 may be employed in any suitable device or system in which two members that, at some period of time, are not connected in fluid flow communication, are to be connected together in a manner that allows fluid to flow from one member to the other. In one example embodiment, the structure and method is described with respect to a first member including a fluid reservoir for containing an infusion medium that may be connectable to a second member including an injection site structure in which a hollow needle or cannula is or may be inserted into a user-patient, for conveying fluid media to the user-patient. However, a connection structure according to embodiments of the present invention may be employed to connect any two (or more) members together for fluid flow communication with each other.

In FIGS. 7-12, an example of a structure 100 and method for connecting two members in fluid flow communication is described with reference to a first member 102 and a second member 103. The first member 102 may include a housing 104 on a base 106. The housing 104 may be formed integral with the base 106 or may be formed as a separate structure connected to the base 106 in a fixed relation to the base 106. The housing 104 and the base 106 each may be made of any suitably rigid material, including, but not limited to plastic, metal, ceramic, composite material, or the like.

The housing 104 may include an injection site section 105 containing an injection site structure in which a hollow needle or cannula may be inserted into a user-patient for conveying fluidic media to or from the user-patient. The housing 104 may be made of a material of suitable strength and durability such as, but not limited to, plastic, metal, glass, or the like. In other embodiments, instead of or in addition to an injection site, the housing 104 may contain, be part of, or be operatively connected to any other suitable structure for conveying, containing, and/or processing fluidic media.

The second member 103 may also include a housing 108, which in the illustrated embodiment may include a reservoir 107 for containing fluidic media. The reservoir 107 may be configured and/or made of materials as previously described with respect to reservoir system 40 (e.g., FIGS. 1-6C). The second member 103 may be held within or otherwise be covered by an outer housing 109 configured to attach to the base 106. The outer housing 109 may be configured to connect to the base 106 of the first member 102 by any suitable connection structure.

In particular embodiments, at least one of the outer housing 109 and the base 106 may include one or more flexible pawls, protrusions, indentations, or the like for engaging and/or receiving one or more corresponding pawls, protrusions, indentations, or the like on the other of the base 106 and the outer housing 109 to provide a suitable connection structure. Alternatively or in addition, the connection structure may include adhesive material or other suitable connectors.

In other embodiments, the housing 108 may be or be connected to a sensor housing (not shown) containing sensor components. In yet other embodiments, the housing 108 may contain, be part of, or be operatively connected to any other suitable structure for conveying, containing, and/or processing fluidic media. The housing 108 may be made of any suitably rigid material, including, but not limited to, plastic, metal, ceramic, composite material, or the like.

The housing 104 may have or be connected to a receptacle structure 110. The receptacle structure 110 may have an opening 112 leading into a chamber 114 within the receptacle structure 110. In some embodiments, the receptacle structure 110 may be part of the housing 104 adjacent a section of the housing 104 containing the injection site section 105. In other embodiments, the receptacle structure 110 may include a further housing connected to the housing 104.

The receptacle structure 110 may include a first septum 116 located within the chamber 114 and may be moveable within the chamber 114 toward and away from the opening 112. The receptacle structure 110 may also include a bias mechanism 118, which may apply a bias force on the first septum 116 in a direction toward the opening 112. The bias mechanism 118 may be arranged for forcing the first septum 116 against the opening 112. One or more annular protrusions or one or more appropriately shaped or positioned protrusions 120 adjacent the opening 112 may be provided to inhibit the first septum 116 from being forced out of the chamber 114 through the opening 112 by the force of the bias mechanism 118.

The first septum 116 may have a front surface 116a that is at least partially exposed through the opening 112 when the first septum 116 is urged against the opening 112 by the bias mechanism 118. The first septum 116 may have a back surface 116b facing toward an interior of the chamber 114. The first septum 116 may be made of any suitable material that may be pierceable by a needle, such as, but not limited to, a natural or synthetic rubber material, silicon, or the like. In some embodiments, the first septum 116 may be made of a self-sealing material capable of sealing itself after a needle has pierced the first septum 116 and was subsequently withdrawn from the first septum 116.

In some embodiments, the bias mechanism 118 may be a coil spring located within the chamber 114 on an opposite side of the first septum 116 with respect to the front surface 116a. In other embodiments, the bias mechanism 118 may be provided in any suitable manner for biasing the first septum 116 toward the opening 112. These may include, but are not limited to, other types of springs, pressurized fluid within the chamber 114, a collapsible skirt structure extending from the first septum 116 with a natural or built-in spring force, chemical, substance that expands upon contact with another chemical or substance, or upon application of energy from an energy source such as a heat, laser, or other radiation source, or the like. For example, in some embodiments, the first septum 116 may have a flexible accordion-like configuration to allow expansion and contraction of the skirt structure.

A needle 124 may be supported within the chamber 114. The needle 124 may be hollow and may have a sharp end 124a directed toward the back surface 116b of the first septum 116. In some embodiments, the needle 124 may be supported within the bias mechanism 118 such that a longitudinal axial dimension of the needle 124 extends generally parallel to a longitudinal axial dimension of the bias mechanism 118.

The needle 124 may be supported by a supporting structure located within the receptacle structure 110. In some embodiments, the supporting structure may be a wall integral with the receptacle structure 110. The supporting structure may be located, for example, on an opposite end of the chamber 114 relative to the end of the chamber 114 at which the opening 112 is located. In other embodiments, the supporting structure may be any suitable structure that is generally fixed relative to the receptacle structure 110 and is able to support the needle 124 in a generally fixed relation to the receptacle structure 110.

The needle 124 may be made of any suitably rigid material, including, but not limited to metal, plastic, ceramic, or the like, and may have a hollow channel extending in a lengthwise dimension of the needle 124. The hollow channel in the needle 124 may be open on the sharp end 124a of the needle 124 and may be open at another location 124b along the lengthwise dimension of the needle 124, such as, but not limited to, the needle end opposite the sharp end 124a. The hollow channel in the needle 124 may provide a fluid flow path between the sharp end 124a of the needle 124 and the opening 124b of the needle 124. In some embodiments, the opening 124b of the needle 124 may be connected in fluid flow communication with a manifold 128 in the injection site section 105.

The housing 108 of the second member 103 may include a connection portion 130 having a hollow interior chamber 132 and an opening 134 into the interior chamber 132. A second septum 136 may be supported by the housing 108 to seal the opening 134. The second septum 136 may be supported in a fixed relation to the housing 108, for example, within the housing 108 at one end of the interior chamber 132.

Figure 7:
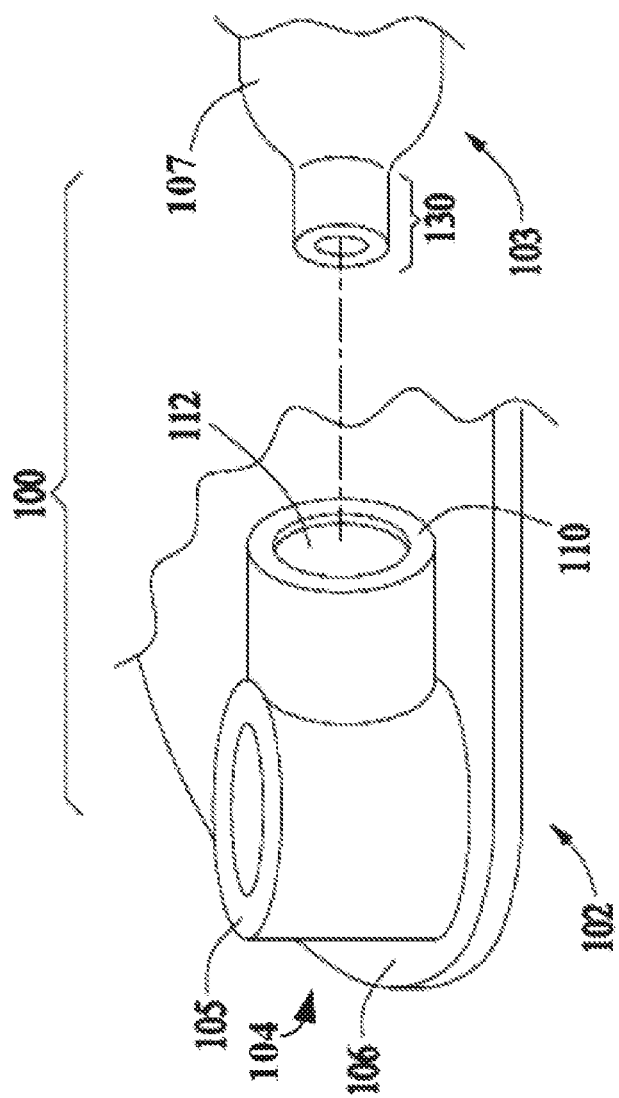
FIG. 7 illustrates portions of a medical device in accordance with an embodiment of the present invention.
Figure 8:
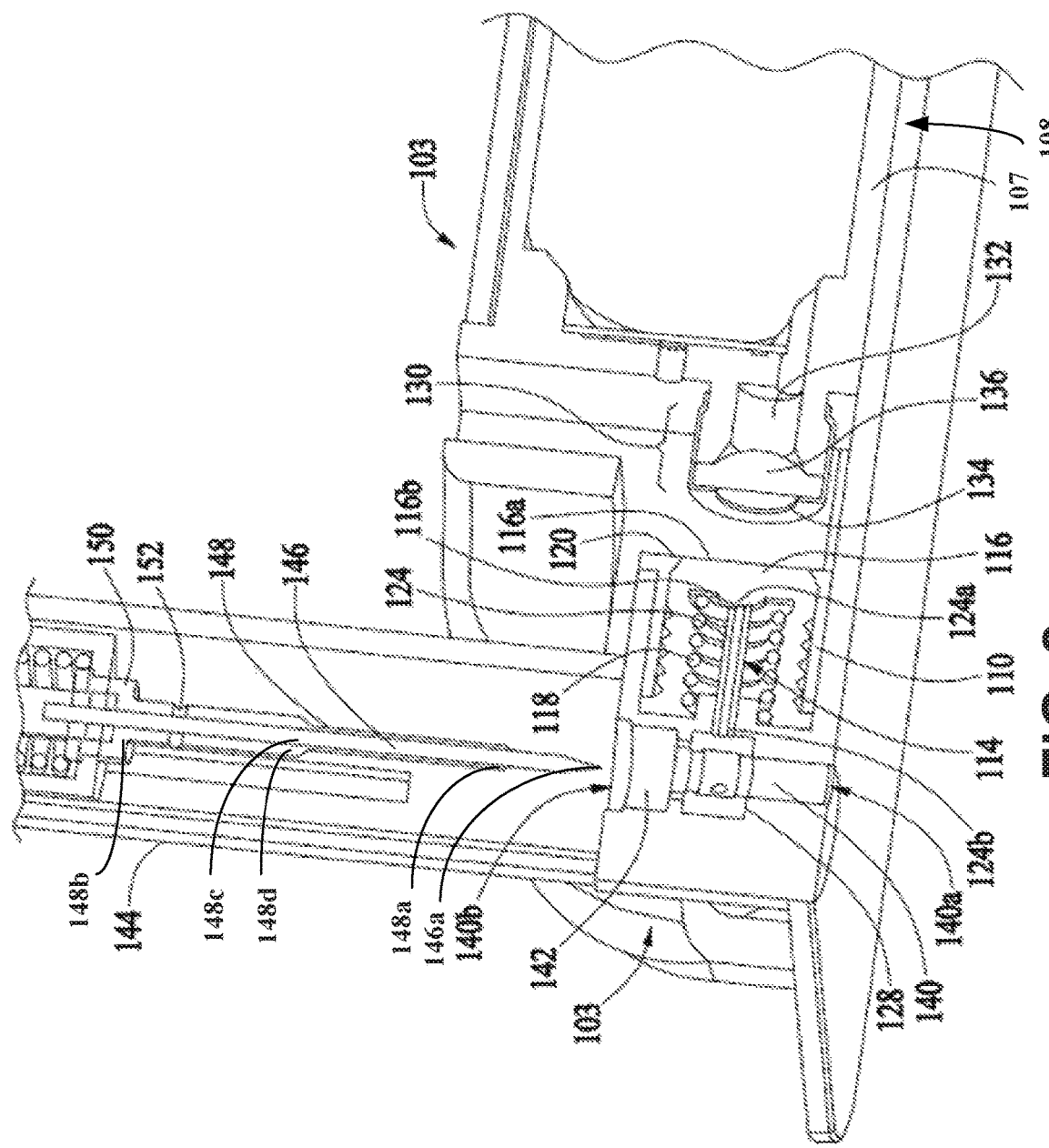
FIG. 8 illustrates a medical device in accordance with an embodiment of the present invention.
Figure 11:
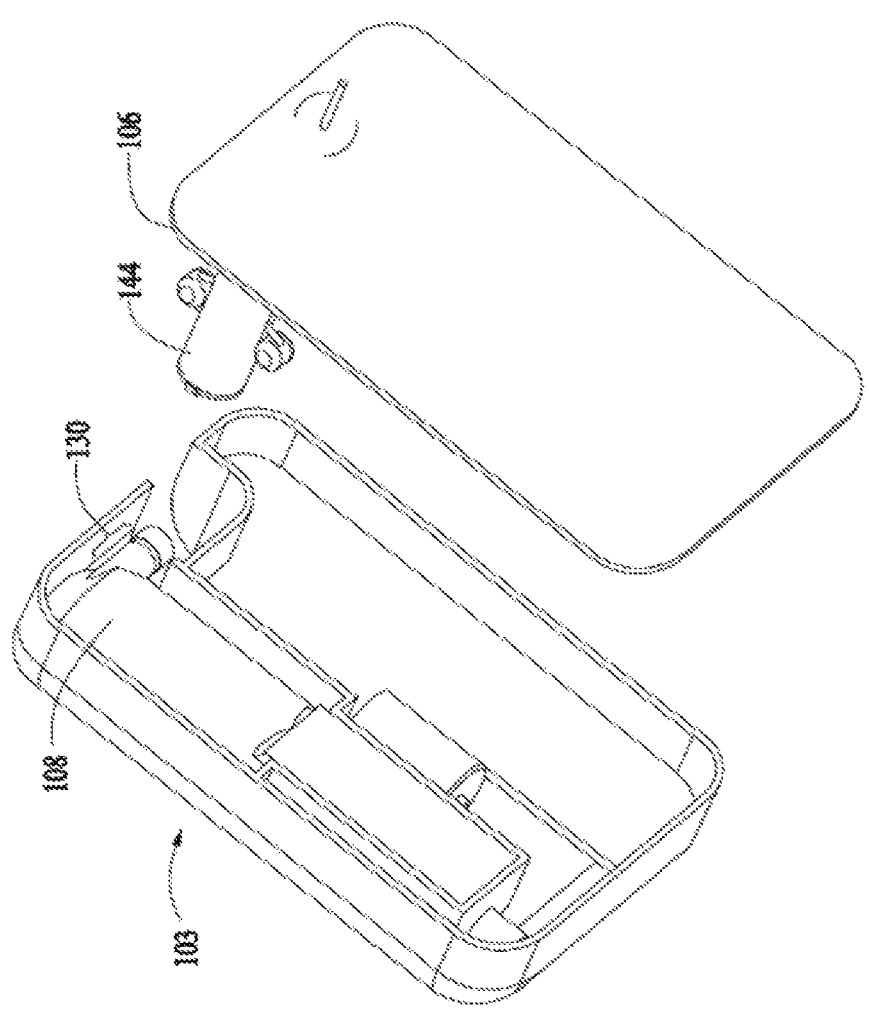
FIG. 11 illustrates a medical device in accordance with an embodiment of the present invention.
Figure 12:
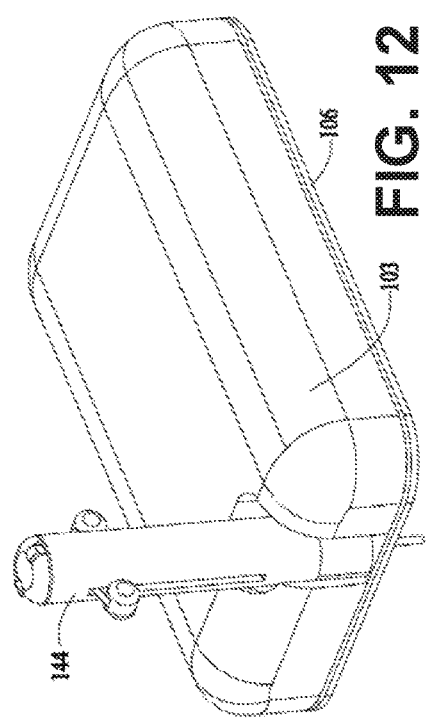
FIG. 12 illustrates a medical device in accordance with an embodiment of the present invention.

The connection portion 130 of the housing 108 may have a suitable shape and size to fit at least partially within the opening 112 of the receptacle structure 110 in the first member 102 when the first member 102 and the second member 103 are connected together. In the drawings of FIGS. 7 and 8, the first member 102 and the second member 103 are shown in a separated, disconnected relation, wherein the connection portion 130 of the housing 108 is outside of the opening 112 of the receptacle structure 110. By moving the first member 102 and the second member 103 together to insert the connection portion 130 into the opening 112 of the housing 108 an end surface of the connection portion 130 may be urged against the first septum 116. This may cause the moveable first septum 116 to move relative to the housing 108 against the force of the bias mechanism 118 toward the interior of the chamber 114. As the first septum 116 is moved toward the interior of the housing 108, the sharp end 124a of the needle 124 may pierce the first septum 116. Continued relative movement of the first member 102 and the second member 103 together may cause the sharp end 124a of the needle 124 to pass through the first septum 116 in the first member 102, then pierce, and pass through the second septum 136 in the second member 103.

When the first member 102 and the second member 103 are brought together (e.g., FIG. 9), at least a portion of the connection portion 130 may extend inside of the receptacle structure 110. With reference to FIGS. 8 and 9, the needle 124 may pierce the first septum 116 and the second septum 136 to form a fluid flow path between the interior chamber 132 of the connection portion 130 and the manifold 128 or other structure at the opening 124b of the needle 124. The receptacle structure 110 and the connection portion 130 may be provided with mating connectors that provide, for example, a snap or friction connection upon the first member 102 and the second member 103 being brought together as shown in FIG. 9. In some embodiments, the mating connectors may include a protrusion (not shown) on one or the other of the receptacle structure 110 and the connection portion 130. The other of the receptacle structure 110 and the connection portion 130 may include a groove or indentation (not shown) arranged to engage each other in a snap-fitting manner upon the connection portion 130 being extended into the receptacle structure 110 a suitable distance.

As mentioned above, in some embodiments, the opening 124b of the needle 124 may be connected in fluid flow communication with the manifold 128 in the injection site section 105. The injection site section 105 may include a channel 140 extending through the housing 104 and the base 106. The channel 140 may have an open end 140a on a bottom surface (relative to the orientation shown in FIG. 8) of the base 106. The channel 140 may have another open end 140b at an upper surface (relative to the orientation shown in FIG. 8) of the injection site section 105 of the housing 104.

The manifold 128 may be located along a length of the channel 140 and may be in fluid flow communication with the channel 140. Accordingly, the needle 124 may be arranged in fluid flow communication with the interior of the channel 140 through the manifold 128. The channel 140 may include a channel section 142 having a larger radial dimension relative to a remaining portion of the channel 140 and may have a suitable shape and size to receive a needle and/or cannula, as will be described later. The manifold 128 may be made of a material of suitable strength and durability such as, but not limited to, plastic, metal, glass, or the like.

A needle-inserting device 144 may be located adjacent the open end 140b of the channel 140 and arranged to selectively extend a needle and/or cannula into the open end 140b of the channel 140 and at least partially through the channel 140 as will be described. In various embodiments, the needle-inserting device 144 may be configured to be integral with or otherwise fixed to the section 105 of the housing 104 of the first member 102. In other embodiments, the needle-inserting device 144 may be a separate device from the housing 104 and may be selectively engaged or connected to, for example in alignment with the channel 140 (e.g., FIG. 8), and disengaged or disconnected from the injection site section 105 of the housing 104.

In embodiments in which the needle-inserting device 144 is a separate structure that connects to and disconnects from the injection site section 105, a suitable connection structure may be provided on the needle-inserting device 144 and/or the injection site section 105 to provide a manually releasable connection between those components. For example, the connection structure may include, but is not limited to, a threaded extension on one or the other of the needle-inserting device 144 and the injection site section 105 and a corresponding threaded receptacle on the other of the injection site section 105 and the needle-inserting device 144 for receiving and mating with the threaded extension in threaded engagement. In other embodiments, other suitable connection structures may be employed, including, but not limited to, flexible pawls or extensions on one or the other of the needle-inserting device 144 and the injection site section 105 and a corresponding aperture, stop surface, or the like on the other of the other of the injection site section 105 and the needle-inserting device 144 or friction fitting engageable portions on each of the section 105 and needle-inserting device 144.

In the drawing of FIG. 8, the needle-inserting device 144 is shown as connected to the injection site section 105 with a needle 146 and a cannula 148 in a retracted state. With reference to FIGS. 7-16, the needle-inserting device 144 may be operated to selectively move the needle 146 and the cannula 148 from the retracted state (e.g., FIG. 8) to an extended state (e.g., FIG. 13) in which the needle 146 and the cannula 148 extend through the opening 140b of the channel 140 and at least partially through the channel 140 such that a sharp end 146a of the needle 146 and at least a portion of the length of the cannula 148 extend out the opening 140a of the channel 140.

Various examples of suitable structures for needle-inserting devices are described in U.S. patent application Ser. No. 11/645,435, filed Dec. 26, 2006, entitled "Infusion Medium Delivery System, Device And Method With Needle Inserter And Needle Inserter Device And Method," which is assigned to the assignee of the present invention and is incorporated herein by reference in its entirety. Further examples of various needle-inserting devices are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method,", all of which are herein incorporated by reference in its entirety. Other examples of suitable structures for needle-inserting devices are described herein.

The cannula 148 may have a hollow central channel 148c extending along a longitudinal length of the cannula 148 and open at one end 148a that may be adjacent the sharp end 146a of the needle 146. An end 148b of the cannula 148 opposite the open end 148a may have a head 150 having a larger radial dimension than a shaft portion 148d of the cannula 148. The cannula head 150 may have a suitable shape and size to fit into the channel section 142 of the channel 140 when the needle 146 and the cannula 148 are moved to the extended state by the needle-inserting device 144.

In particular embodiments, the cannula head 150 may include one or more protrusions and/or indentations for engaging one or more corresponding indentations and/or protrusions in the channel section 142 of the injection site section 105 to provide a friction fit, snap fit, or the like. Accordingly, the cannula 148 may be locked or retained within the injection site section 105 upon the needle 146 and cannula 148 being moved to the extended state by the needle-inserting device 144. In further embodiments, instead of or in addition to engaging protrusions and indentations, one or more other mechanical structures may be employed to provide a suitable retaining function for retaining the cannula 148 in place within the injection site section 105, including, but not limited to, a friction fit structure, snap fit, or the like.

The cannula 148 may have a connection channel 152 provided in fluid flow communication with the hollow central channel 148c of the cannula 148. The connection channel 152 may be provided along the longitudinal length of the cannula 148 at a location at which the connection channel 152 aligns with the manifold 128 (i.e., in fluid flow communication with an interior of the manifold 128) when the needle 146 and the cannula 148 have been moved to the extended state by the needle-inserting device 144. In this manner, upon the cannula 148 being moved to the extended state, the hollow central channel 148c of the cannula 148 may be arranged in fluid flow communication with the reservoir 108 through the manifold 128 and the connection channel 152.

Thus, according to some embodiments, in operation, a first member 102, which may include, for example, a housing 104 having a receptacle 110 and an injection site section 105, may be coupled together with a second member 103, which may include, for example, a housing 108 having a reservoir 107. The first member 102 may be coupled or otherwise operatively connected, by inserting a connection portion 130 of the second member 103 into a receptacle 110 of the first member 102. Upon coupling the first member 102 and the second member 103, fluid flow communication may be provided between the second member 103 and the injection site section 105 in the first member 102.

In various embodiments, the needle-inserting device 144 may be coupled to the injection site section 105 of the housing 104 of the first member 102 or may be provided as part of a single, unitary structure (i.e., integral) with the injection site section 105 of the housing 104. In some embodiments, the base 106 of the first member 102 may be secured to skin of a user-patient at a suitable injection location with, for example, but not limited to, adhesive material as described in U.S. patent application Ser. No. 11/645,435, filed Dec. 26, 2006, entitled "Infusion Medium Delivery system, Device And Method With Needle Inserter And Needle Inserter Device And Method," and/or as described herein. Alternatively or in addition, the base 106 may be secured to the user-patient by one or more other suitable structures, including, but not limited to, straps, or the like.

Once the base 106 is suitably secured to the skin of the user-patient at a suitable injection location, the inserting device 144 may be actuated to move the needle 146 and the cannula 148 from a retracted state (e.g., FIG. 8) to an extended state. In the extended state, the needle 146 and/or the cannula 148 may pierce the skin of the user-patient adjacent the base 106. The cannula 148 may be locked into its extended state by engagement of the cannula head 150 and the channel section 142, as previously described.

With the cannula 148 locked in the extended state, the needle 146 may be retracted, for example, by automatic operation of the needle-inserting device 144 and/or by manual removal of the needle-inserting device 144 from the injection site section 105. Once the needle 146 is removed, the cannula 148 may be held in place by the injection site section 105 with a portion of the cannula 148 extending into the user-patient. As such, the cannula 148 may be connected in fluid-flow communication with the needle 124. Accordingly, by connecting the first member 102 and the second member 103, as described above, then a fluid-flow connection may be provided from the reservoir 107 to the cannula 148 through the needle 124 and the manifold 128.

A connection sequence (e.g., the sequence of connecting the needle-inserting device 144 to the injection site section 105 of the housing 104, connecting the receptacle 110 of the housing 104 to the connection portion 130 of the housing 108 having the reservoir 107, and connecting the base 106 of the first member 102 to the skin of the user-patient) for connecting various components may be different for different embodiments. In some embodiments, the user-patient may be provided with a first member 102 having a base 106, a housing 104, and an injection site section 105 in a pre-connected state with the needle-inserting device 144. In this manner, a user-patient need not have to connect the needle-inserting device 144 to the housing 104 as those parts are supplied to the user in a pre-connected state, for example, from a manufacturing or assembly facility. In such embodiments, the base 106 of the first member 102 may be secured to skin of the user-patient at a suitable injection location. After securing the base 106 to the skin of the user-patient, the needle-inserting device 144 may be activated to cause the needle 146 and the cannula 148 to be moved to the extended state and pierce the skin of the user-patient.

After activation of the needle-inserting device 144, the needle-inserting device 144 may be removed from the injection site section 105, thus leaving the cannula 148 in place within the injection site section 105 and partially extended into the user-patient. With the base 106 of the first member 102 secured to the skin of the user-patient and the cannula 148 inserted at least partially into the user-patient and arranged in fluid-flow communication with the needle 124, the second member 103 may be connected to the first member 102. In particular, the connection portion 130 of the housing 108 of the second member 103 may be inserted into the receptacle 110 of the housing 104 of the first member 102 to provide a fluid-flow connection between the interior of the housing 108 and the needle 124 and, thus, the cannula 148. Accordingly, the housing 108, which may include the reservoir 107, for example, may be coupled in fluid-flow communication with the cannula 148 that has been extended into the user-patient for delivering fluid from the reservoir 107 to the user-patient. In other embodiments, such a connection may be for conveying fluid from the user-patient to the reservoir 107.

While the connection sequence in some of the above embodiments involve securing the base 106 of the first member 102 to the user-patient prior to connection of the second member 103 to the first member 102, in other embodiments, the second member 103 may be connected to the first member 102, as described above, prior to securing the base 106 of the first member 102 onto the skin of the user-patient. In such embodiments, the first member 102 and the second member 103 may be connected together and, thereafter, may be secured to the user-patient, for example, by adhering one or both of the first member 102 and the second member 103 to the skin of the user-patient. In addition, while the connection sequence in the above embodiments involve activating the needle-inserting device 144 prior to the connection of the second member 103 to the first member 102, in other embodiments, the second member 103 may be connected to the first member 102, as described above, prior to activating the needle-inserting device 144.

In some embodiments, such as the embodiments shown in FIGS. 7 and 8, the receptacle 110 may be in the first member 102 and the connection portion 130 may be in the second member 103. In other embodiments, the receptacle 110 may be in the second member 103, for example, in or associated with a housing for a reservoir and the connection portion 130 may be in the first member 102, for example, in or associated with a housing containing an injection site structure.

In some embodiments, such as the embodiments shown in FIGS. 7 and 8, the receptacle 110 may be arranged to allow the connection portion 130 of the second member 103 to be inserted in a direction substantially parallel to a plane of an upper-facing (in the orientation of FIG. 7) surface of the base 106. For example, in the orientation of FIG. 7, the direction of insertion is shown as a horizontal direction of relative motion between the first member 102 and the second member 103.

Again referring to FIGS. 7 and 8, in other embodiments, the receptacle 110 may be arranged in other suitable orientations, including, but not limited to, an orientation allowing an insertion direction (i.e., relative motion of the first member 102 and the second member 103) to be substantially perpendicular to the plane of the upper-facing surface of the base 106. In yet other embodiments, the receptacle 110 may be arranged to allow any other suitable insertion direction at a non-perpendicular angle transverse to the plane of the upper-facing surface of the base 106.

Figure 13:
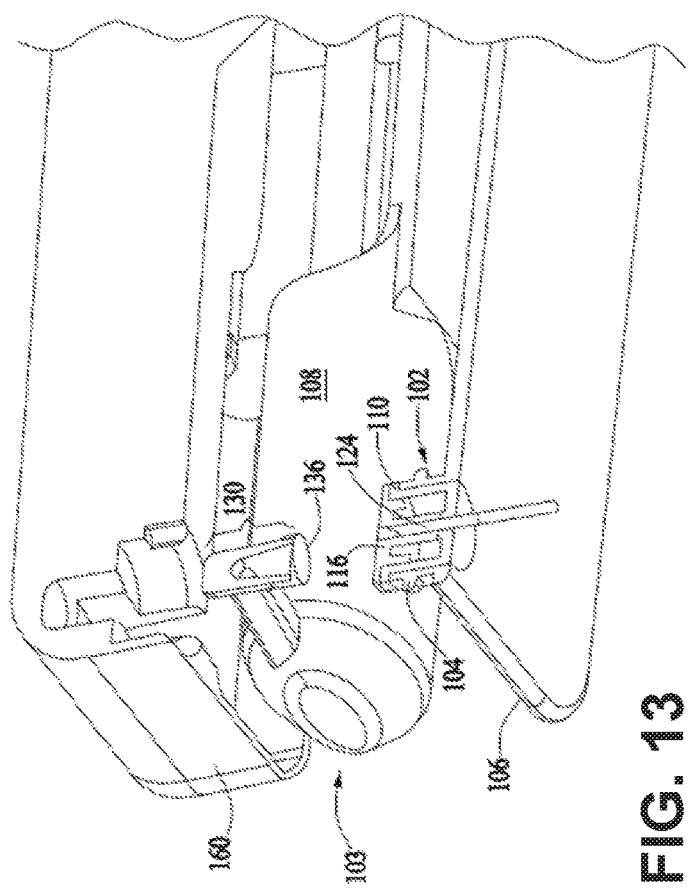
FIG. 13 illustrates a medical device in accordance with an embodiment of the present invention.
Figure 14:
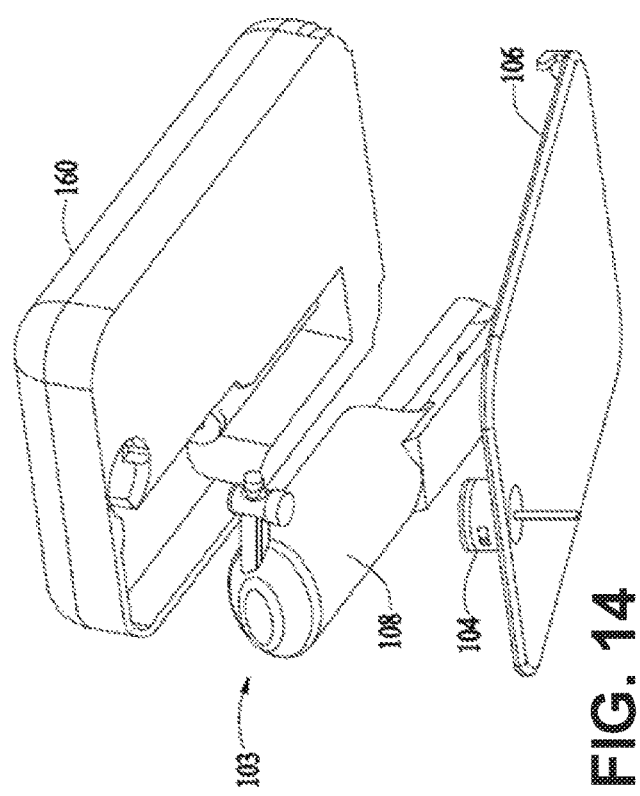
FIG. 14 illustrates a medical device in accordance with an embodiment of the present invention.

An example arrangement shown in FIGS. 13-16 provides an insertion direction (i.e., relative motion of the first member 102 and the second member 103) that may be substantially perpendicular to the plane of the upper-facing (in the orientation of FIG. 8) surface of the base 106. Components in FIGS. 13-16 are identified by reference numbers that are the same as reference numbers used in FIGS. 7-12 for components having similar structure and function. In FIGS. 13 and 14, the injection site section 105 in the housing 104 is shown in a state after a needle-inserting device has been operated to move a cannula 148 to the extended position.

Figure 15:
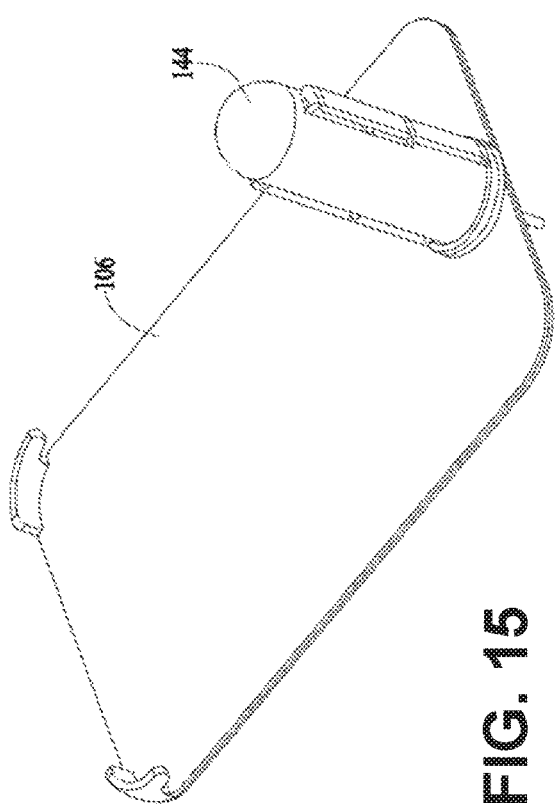
FIG. 15 illustrates a medical device in accordance with an embodiment of the present invention.
Figure 16:
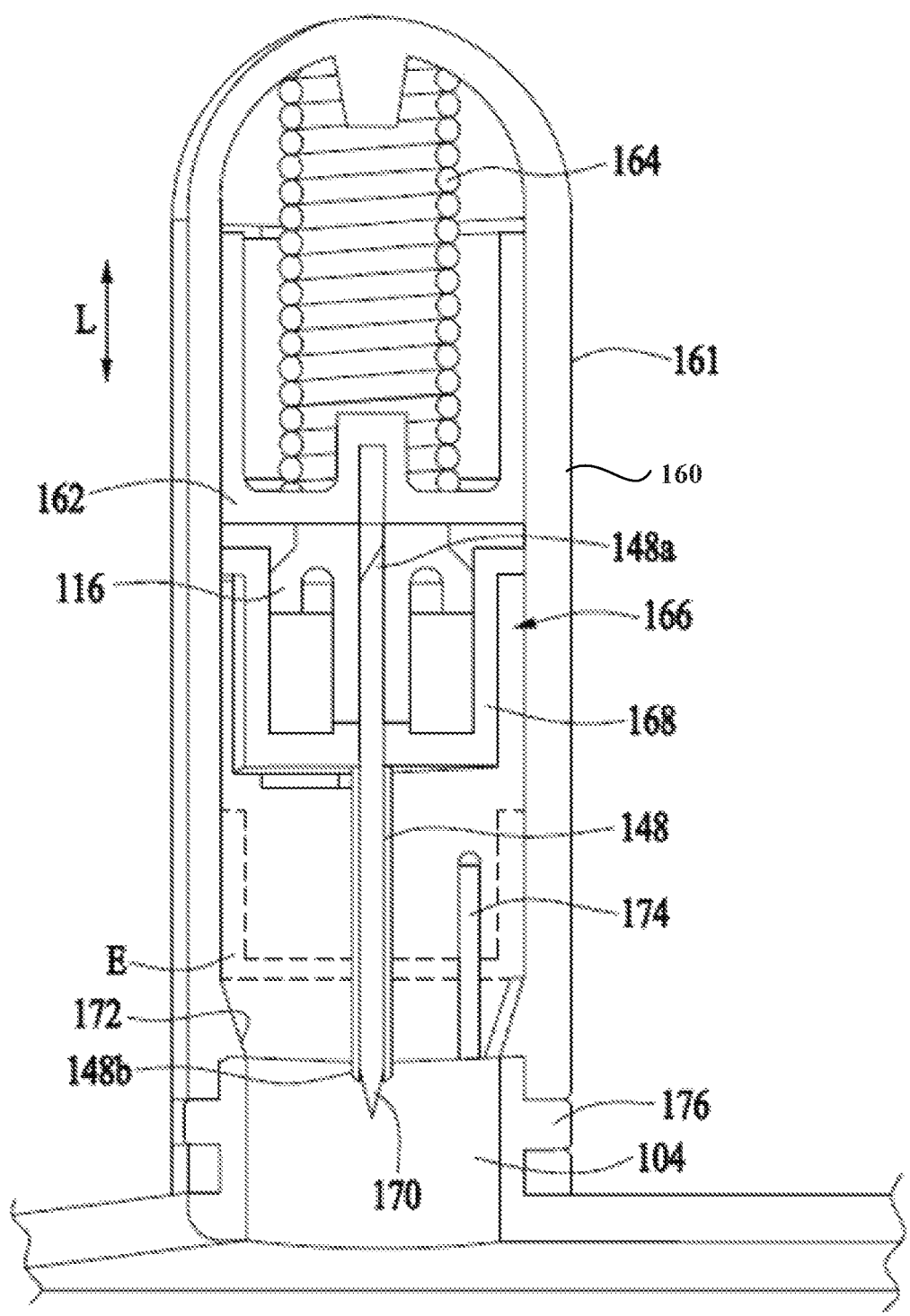
FIG. 16 illustrates cross-section of a needle-inserting device in accordance with an embodiment of the present invention.
Figure 17:
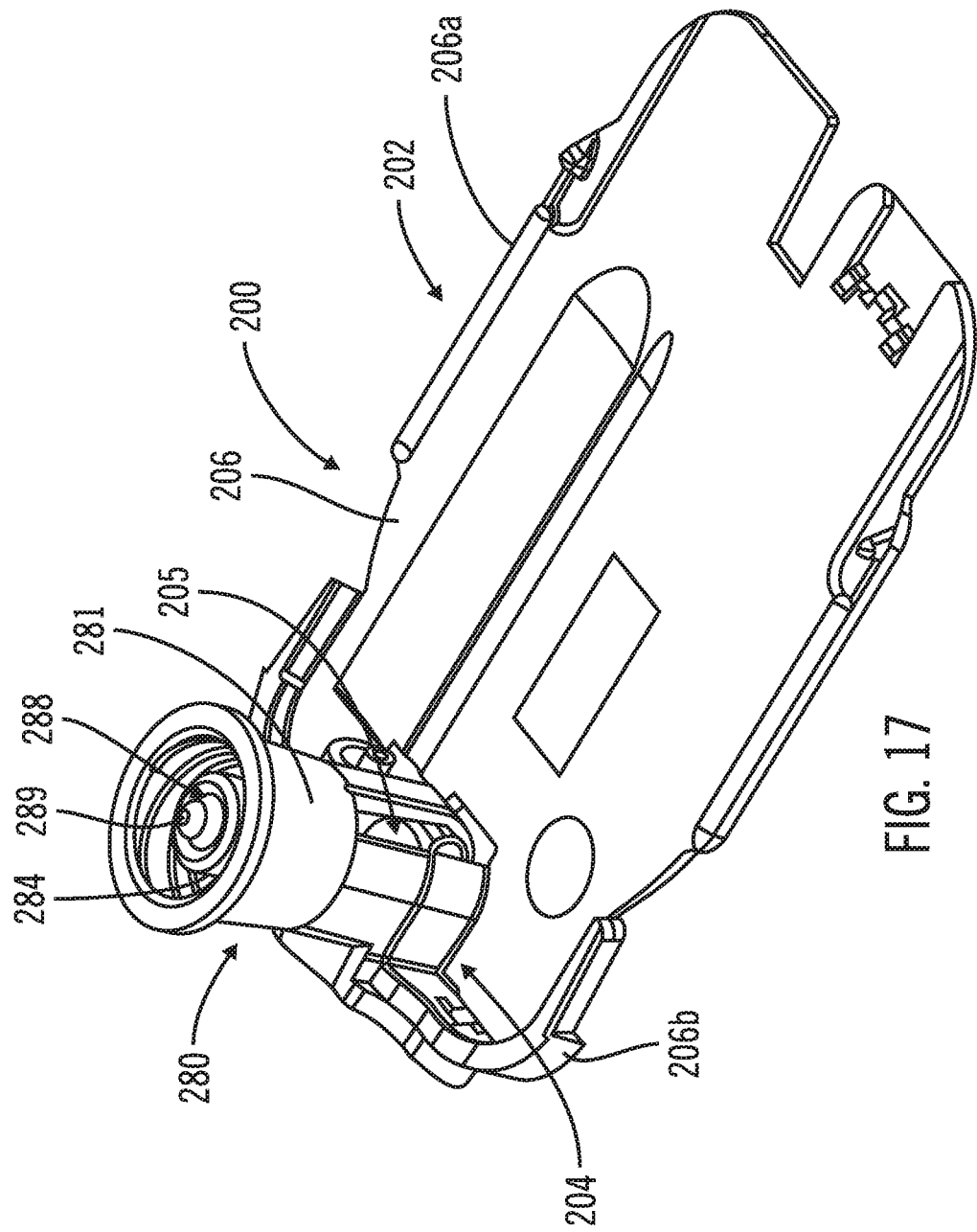
FIG. 17 illustrates a medial device in accordance with an embodiment of the present invention.

FIGS. 15 and 16 show the base 106 of the first member 102 (of the embodiment of FIGS. 13 and 14) with a needle-inserting device 144 attached to the housing 104. The needle-inserting device 144 may include a housing 160 adapted to be securable to the base 106 in any suitable manner, such as, but not limited to, the manners of connecting a needle-inserting device 144 to the injection site structure 105 discussed above with respect to the embodiment of FIGS. 7-12. Returning to FIGS. 15 and 16, the housing 160 may contain an internal chamber having a longitudinal dimension L and a moveable plunger 162 located within the housing 160 and moveable along the longitudinal dimension L from a retracted position (shown in solid lines in FIG. 16) to an extended position (in which the plunger 162 is moved to a position E shown in broken lines in FIG. 16).

A bias member 164, such as, but not limited to, a coil spring arranged within the housing 160 may be configured to impart a bias force on the plunger 162 when the plunger 162 is in the retracted position to urge the plunger 162 toward the extended position E. A locking mechanism (not shown) may be provided such as, but not limited to, a manually moveable projection, lever, slider, or the like, connected to or extending through the housing 160 and engages the plunger 162 or other structure holding the plunger 162 in a releasable manner to selectively hold the plunger 162 in its retracted state against the bias force of the bias member 164 and to allow a user-patient to selectively release the plunger 162 to move in the longitudinal direction L under the force of the bias member 164.

An insert structure 166 may be arranged within the housing 160 for movement in the longitudinal direction L by action of movement of the plunger 162. The insert structure 166 may include, for example, a cup-shaped body 168. The cup-shaped body 168 may be made of a material of suitable strength and durability such as, but not limited to, plastic, metal, glass, or the like. The cup-shaped body 168 may hold a first septum 116. The septum 116 may be made of a material such as silicone, rubber, plastic, a resealable membrane, or the like.

A hollow cannula 148 may have one open end 148*a* and a sharp tip arranged adjacent the first septum 116 or at least partially within the first septum 116. The hollow cannula 148 may extend through the cup-shaped body 168 and may have a second open end 148*b*. The hollow cannula 148 may be fixed to the cup-shaped body 168 to move with movement of the cup-shaped body 168. A needle 170 may be secured to the plunger 162 and may extend through the first septum 116 and cannula 148 when the plunger 162 is in the retracted position.

In operation, the user-patient (or medical practitioner) may secure the base 106 to skin of the user-patient, for example, as previously described. Once the base 106 is secured to the skin of the user-patient, the user-patient (or medical practitioner) may activate the needle-inserting device 144 to cause the plunger 162 to move from the retracted position to the extended position E and, as a result of such movement, to cause the insert structure 166 to be moved into an opening into the interior of the housing 104. Upon movement of the insert structure 166 into the housing 104, the insert structure 166 may connect to the housing 104 by any suitable connection structure.

As discussed above, in particular embodiments, one or the other of the cup-shaped body 168 of the insert structure 166 and the housing 104 may include one or more flexible pawls, protrusions, indentations, or the like, for engaging and receiving one or more corresponding pawls, protrusions, indentations, or the like, on the other of the housing 104 and the insert structure 166 to provide a suitable connection structure. Alternatively or in addition, the connection structure may include adhesive material or other suitable connectors.

In particular embodiments, the housing 160 of the needle-inserting device 144 may automatically release from the base 106 upon movement of the plunger 162 and the insert structure 166 from the retracted position to the extended position E. For example, the housing 160 of the needle-inserting device 144 may be made of a material that has sufficient rigidity to operate as described herein, but also has a suitable flexibility (at least at the portion of the device 144 that connects to the housing 104) to bend away from and release from the housing 104 upon movement of the insert structure 166 to the extended position E.

In some embodiments, such as the embodiment shown in FIG. 16, a portion 172 of the internal surface of the housing 160 may include a ramped, wedge-shaped, or angled (relative to an axial direction of the housing 144, cannula 148, and needle 170) cross-sectional shape that engages an outer peripheral surface of the insert structure 166 and/or the plunger 162 as the insert structure 166 and plunger 162 are moved toward the extended position E. By engaging the angled, ramped, or wedge-shaped portion 172 of the internal surface of the housing 160, the plunger 162 and/or the insert structure 166 may cause the wall(s) of the housing 160 to flex outward as the plunger 162 and/or insert structure 166 are moved into the extended position. One or more slots, grooves, or the like 174 may be formed in the housing 166 to enhance the ability of the wall(s) of the housing 160 to flex outward. One or more protrusions 176 and/or indentations may be provided on one or the other of the interior surface of the housing 166 and the exterior surface of the housing 104 for engaging one or more corresponding indentations 178 and/or protrusions in the other of the housing 104 and housing 166 when the plunger 162 and insert structure 166 are in the retracted state shown in FIG. 16.

The one or more protrusions 176 and the one or more indentations 178, when engaged, may lock the housing 160 of the needle-inserting device 144 to the housing 104. The one or more protrusions 176 and/or indentations 178 may disengage from each other when the wall(s) of the housing 160 are flexed outward by the movement of the plunger 162 and the insert structure 166 to the extended position E. As a result, the housing 160 of the needle-inserting device 144 may be automatically disengaged and released from the housing 104 upon movement of the plunger 162 and insert structure 166 to the extended position E.

After movement of the plunger 162 and insert structure 166 from the retracted position (shown in FIG. 16) to the extended position E at which the insert structure 166 may be locked into the housing 104, while the housing 160 of the needle-inserting device 144 is released from the housing 104, the bias member 164 (or a second bias member (not shown)) may act on the needle 170 to move the needle 170 toward the retracted position and, thus, withdraw the needle 170 from the cannula 148. For example, a return motion of the coil spring after moving from the retracted position to the extended position E may provide sufficient force to withdraw the needle 170 from the cannula 148.

Once the insert structure 166 has been locked into place within the housing 104 and the needle-inserting device 144 has been removed from the housing 104, the cannula 148 may be connected in fluid-flow communication with a connection portion 130 of a second member such as, but not limited to, a reservoir, in a manner similar to the manner in which the first member 102 and the second member 103 are connectable in the embodiments of FIGS. 7-12. More specifically, the housing 104 may form a receptacle (similar to the receptacle 110 described above for FIGS. 7-12) and may contain the first septum 116.

Similar to the embodiment of FIGS. 7-12, the connection portion 130 may also include a second septum 136. In particular, the connection portion 130 may be inserted into the receptacle formed by the housing 104 to connect the interior of the reservoir in fluid-flow communication with the cannula 148. The cannula 148 in FIG. 13 may include a sharp end 148a adjacent the first septum 116. As the connection portion 130 is inserted into the housing 104, the connection portion may push the first septum 116 against the sharp end 148a of the cannula 148 to cause the sharp end 148a of the cannula 148 to pierce the first septum 116. Further insertion motion of the connection portion 130 into the housing 104 may cause the sharp end 148a of the cannula 148 to pierce the second septum 136 in the connection portion 130 to form a flow path from or to the connection portion 130 through the cannula 148.

Figure 21:
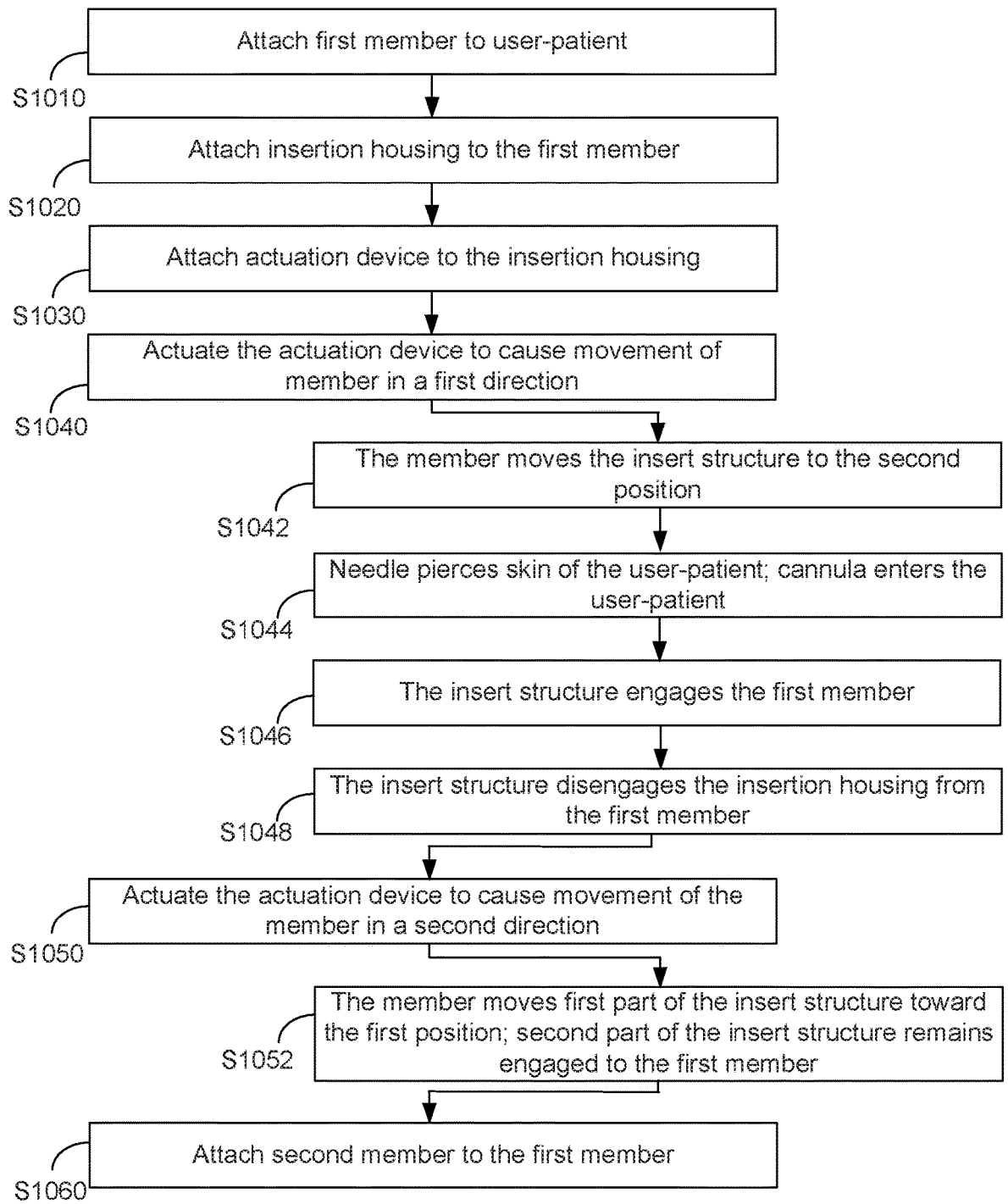
FIG. 21 illustrates flow chart for using a medial device in accordance with an embodiment of the present invention.

FIGS. 17-20 illustrate an inserting system 200 according to an embodiment of the present invention. FIG. 21 illustrates a process for using the inserting system 200. Although the inserting system 200 may be similar or used with the embodiments of FIGS. 1-16, it should be understood that the inserting system 200 may also include some or all of the same components and operate in a manner similar to that shown and described in the embodiments of FIGS. 22-43. In addition, some or all of the features shown in FIGS. 1-16 and 22-43 may be combined in various ways and included in the embodiments and process shown in FIGS. 17-21. Likewise, it should be understood that any of the features of the embodiments and process of FIGS. 17-21 may be combined or otherwise incorporated into any of the other embodiments and process of FIGS. 17-21 as well as any other embodiment herein discussed.

The inserting system 200 may include a first member 202, which may be similar to the first member 102 (e.g., FIGS. 7-12). The first member 202 may include a housing 204 on a base 206. The housing 204 may be formed integral with the base 206 or may be formed as a separate structure connected to the base 206 in a fixed relation to the base 206. The housing 204 and the base 206 each may be made of any suitably rigid material, including, but not limited to plastic, metal, ceramic, composite material, or the like.

The housing 204 may include an injection site section 205 containing an injection site structure in which a hollow needle or cannula may be inserted into a user-patient for conveying fluidic media to or from the user-patient. In other embodiments, instead of or in addition to an injection site, the housing 204 may contain, be part of, or be operatively connected to any other suitable structure for conveying, containing, and/or processing fluidic media.

The first member 202 may be operatively connectable to a second member (not shown), which may be similar to the second member 103 (e.g., FIGS. 7-12). As previously described with respect to FIGS. 7-12, the second member may also include a housing 108, which in the illustrated embodiment may include a reservoir 107 for containing fluidic media. The second member may be held within or otherwise be covered by an outer housing 109 configured to attach to the base 106. The outer housing 109 may be configured to connect to the base 206 (FIGS. 17-20) of the first member 202 (FIGS. 17-20) by any suitable connection structure. In some embodiments, upon coupling the first member 202 and the second member, fluid flow communication may be provided between the second member and the injection site section 205 in the first member 202.

In particular embodiments, at least one of the outer housing 109 and the base 206 (FIGS. 17-20) may include one or more flexible pawls, protrusions, indentations, or the like for engaging and/or receiving one or more corresponding pawls, protrusions, indentations, or the like on the other of the base 206 (FIGS. 17-20) and the outer housing 109 to provide a suitable connection structure. Alternatively or in addition, the connection structure may include adhesive material or other suitable connectors.

Returning to FIGS. 17-20, the housing 204 may have or be connected to a receptacle structure 210 having a chamber 214. The receptacle structure 210 may be similar to the receptacle structure 110 (e.g., FIGS. 7-12) previously described. In some embodiments, the receptacle structure 210 may be part of the housing 204 adjacent a section of the housing 204 containing the injection site section 205. In other embodiments, the receptacle structure 210 may include a further housing connected to the housing 204.

A fluid conduit 224, such as, but not limited to, a needle or the like may be supported within the chamber 214. The fluid conduit 224 may be supported by a supporting structure located within the receptacle structure 210. In some embodiments, the supporting structure may be a wall integral with the receptacle structure 210. In other embodiments, the supporting structure may be any suitable structure that is generally fixed relative to the receptacle structure 210 and is able to support the fluid conduit 224 in a generally fixed relation to the receptacle structure 210.

The fluid conduit 224 may be made of any suitably rigid material, including, but not limited to metal, plastic, ceramic, or the like, and may have a hollow channel extending in a lengthwise dimension of the fluid conduit 224. The hollow channel in the fluid conduit 224 may be open at a location (not shown) along the lengthwise dimension of the fluid conduit 224, such as, but not limited to, a first end of the fluid conduit 224. The hollow channel in the fluid conduit 224 may be open at another location 224b along the lengthwise dimension of the fluid conduit 224, such as, but not limited to, a second end of the fluid conduit 224 opposite the first end of the fluid conduit 224. One of the openings in the fluid conduit 224 may be provided with a septum 226 that may be pierceable by a needle (not shown), for example as previously described, when a reservoir is connected to the first member 202.

The injection site section 205 may include a channel 240 extending through the housing 204 and the base 206. The channel 240 may have an open end 240a on a bottom surface (relative to the orientation shown in FIG. 18) of the base 206. The channel 240 may have another open end 240b at an upper surface (relative to the orientation shown in FIG. 18) of the injection site section 205 of the housing 204. The channel 240 may include a channel section 242 having a larger radial dimension relative to a remaining portion of the channel 240 and may have a suitable shape and size to receive an insert structure, a needle, and/or a cannula, as will be described.

The insertion system 200 may include an insertion housing 280. The insertion housing 280 may be made of a material of suitable strength and durability such as, but not limited to, plastic, metal, glass, or the like. The insertion housing 280 may be located adjacent the open end 240b of the channel 240 and arranged to selectively extend a needle and/or cannula of an insert structure into the open end 240b of the channel 240 and at least partially through the channel 240 as will be described.

The insertion housing 280 may be a separate device from the housing 204 and may be selectively engaged or connected to, for example in alignment with the channel 240, and disengaged or disconnected from the injection site section 205 and/or the first member 202 or portion thereof. In some embodiments, the insertion housing 280 may be recommended for disposal after a specified number of uses.

Figure 18:
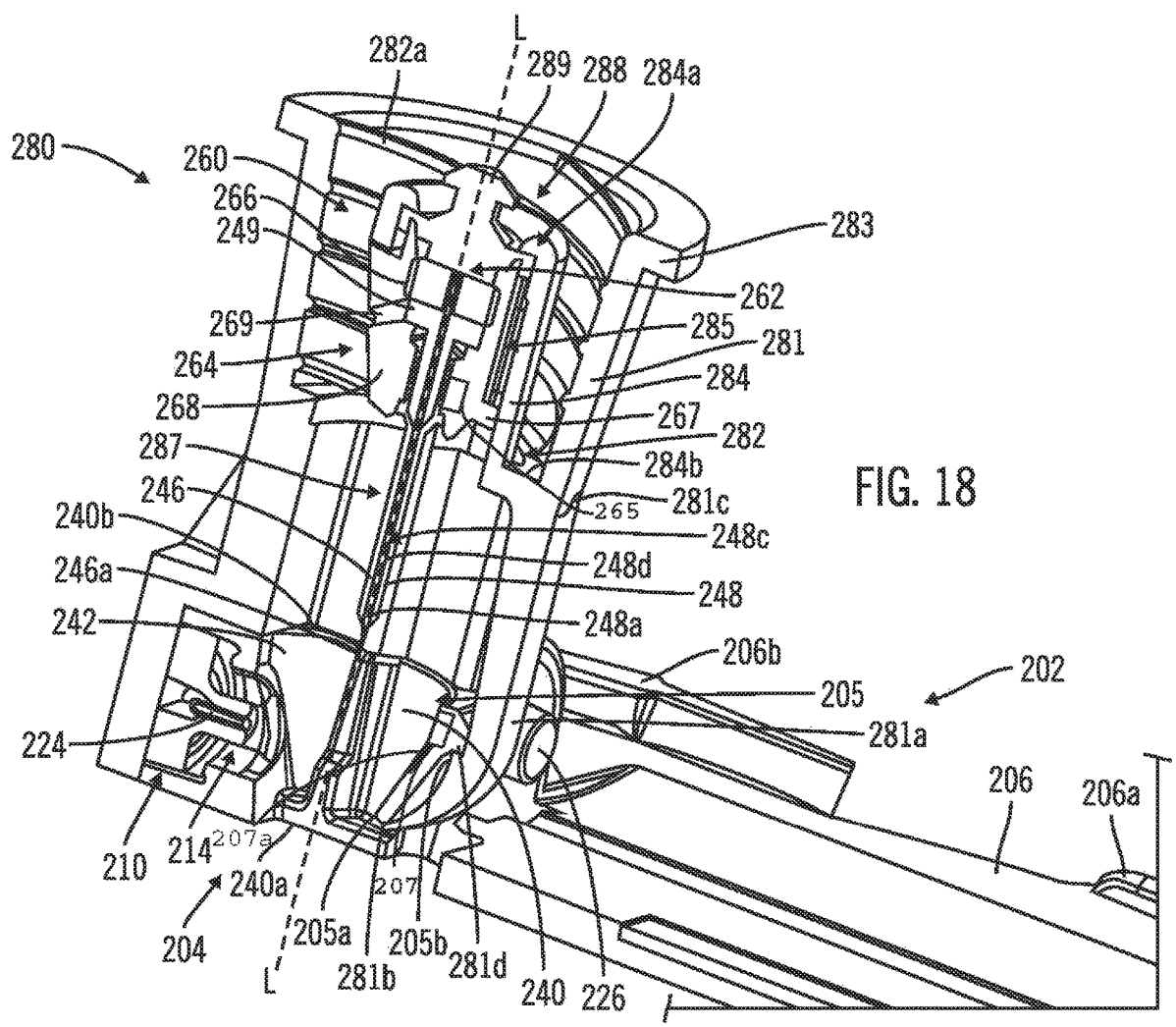
FIG. 18 illustrates a medial device in accordance with an embodiment of the present invention.
Figure 19:
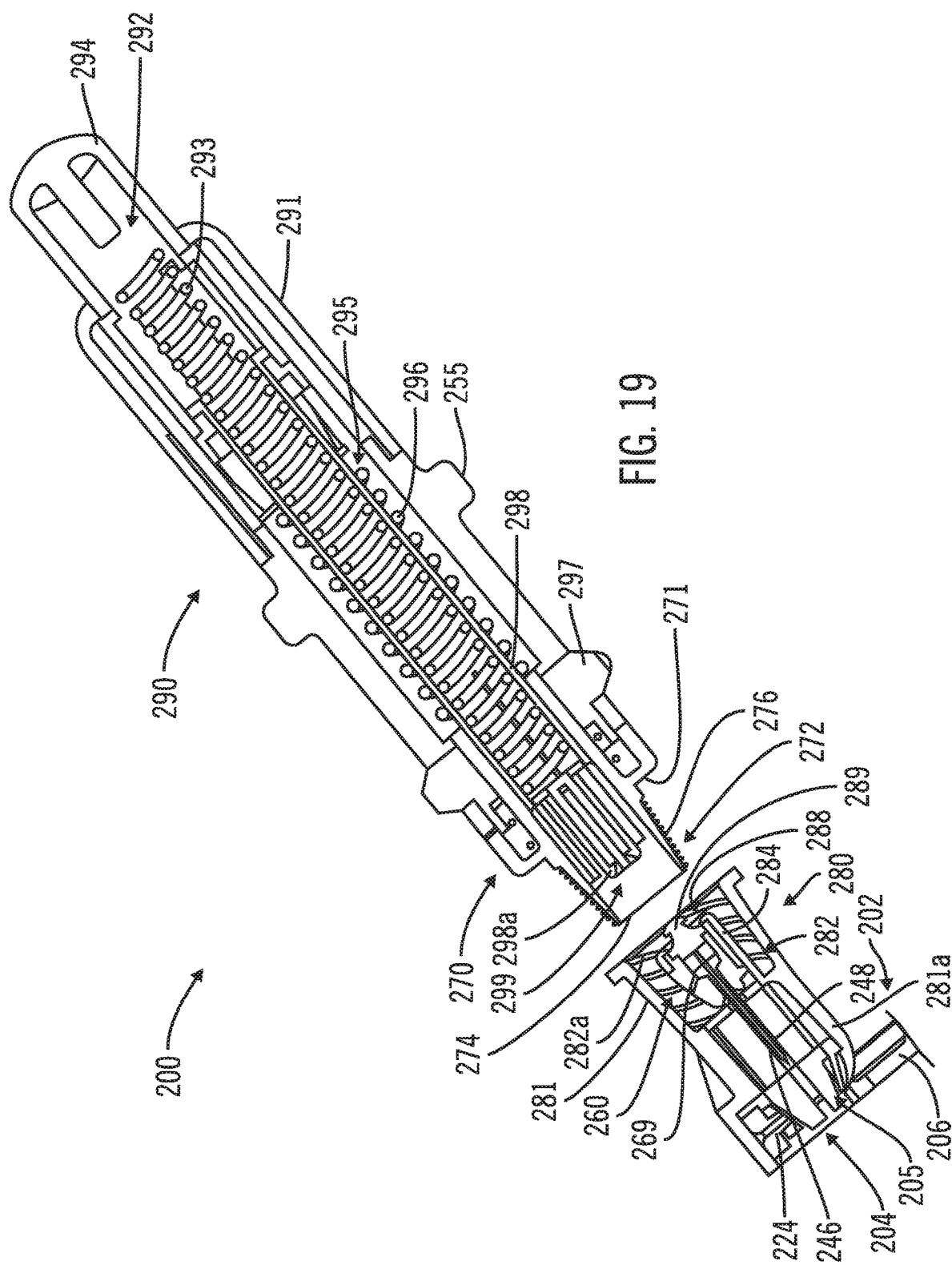
FIG. 19 illustrates a medial device in accordance with an embodiment of the present invention.
Figure 20:
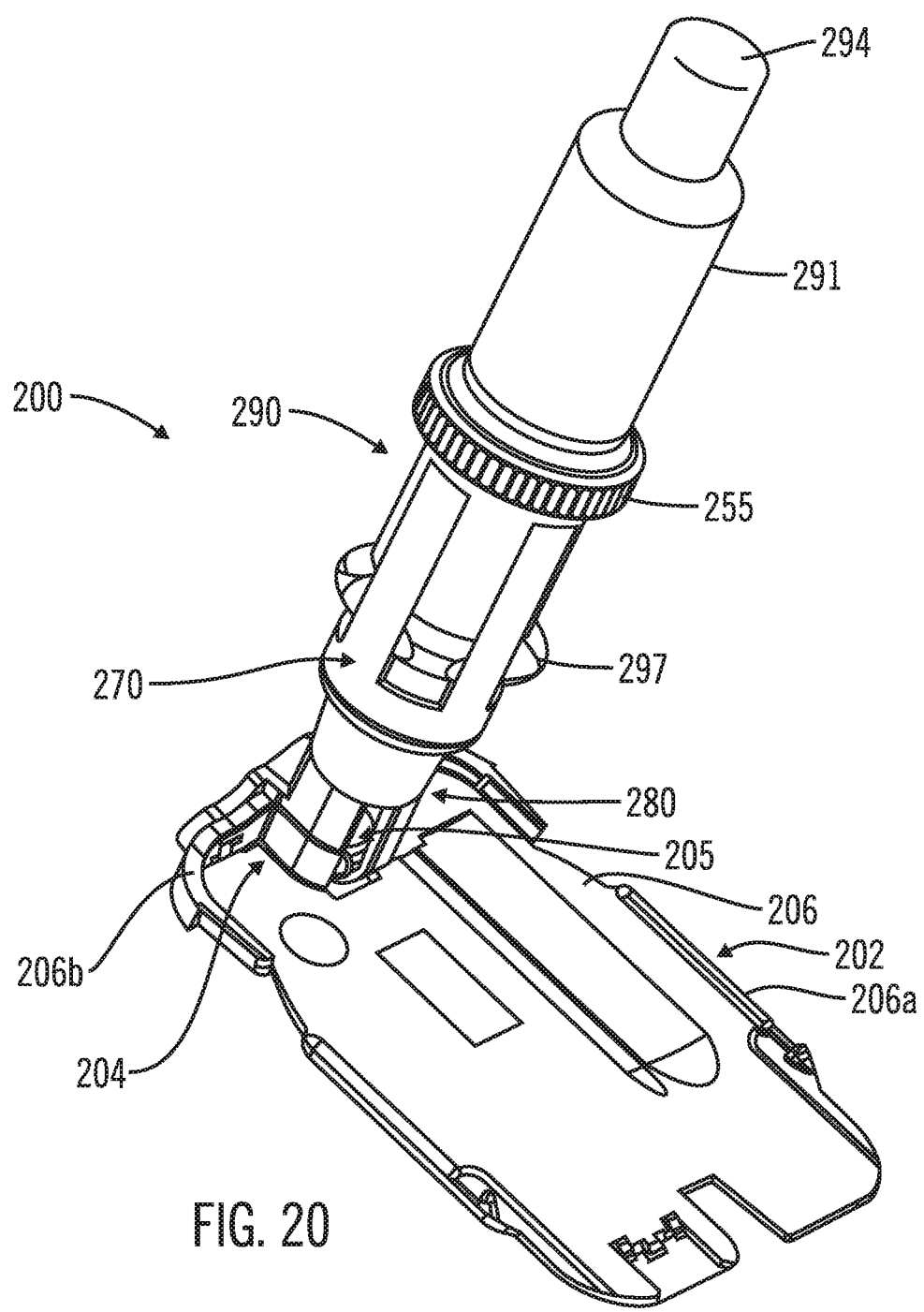
FIG. 20 illustrates a medial device in accordance with an embodiment of the present invention.

In the drawing of FIG. 18, the insertion housing 280 is shown as connected to the injection site section 205. With reference to FIGS. 17-20, a suitable connection structure may be provided on the insertion housing 280, the injection site section 205, and/or the first member 202 or portion(s) thereof to provide a manually releasable connection between those components. For example, the connection structure may include, but is not limited to, a threaded extension on one or the other of the insertion housing 280 and the injection site section 205 and a corresponding threaded receptacle on the other of the injection site section 205 and the insertion housing 280 for receiving the threaded extension in threaded engagement. In other embodiments, other suitable connection structures may be employed. These may include, but are not limited to, friction-fitted sections, flexible pawls or extensions on one or the other of the insertion housing 280 and the injection site section 205 (or the first member 202 or portion thereof) and a corresponding aperture, stop surface, or the like on the other of the injection site section 205 (or the first member 202 or portion thereof) and the insertion housing 280.

In some embodiments, the insertion housing 280 may include one or more arm 281a having an end 281b and/or a locking surface 281d adapted to operatively engage with and disengage from the first member 202, such as an aperture 205a and/or a retaining surface 205b, respectively, of the insertion site section 205, or the like. The arm 281a may be made of any suitably rigid material, such as plastic, glass, metal, composite material, ceramic, and/or the like. In some embodiments, the arm 281a may be made of similar material as the insertion housing 280. In other embodiments, the arm 281a may be made of different material from the insertion housing 280.

In some embodiments, the arm 281a may be integral with the insertion housing 280 and the arm 281a may be sufficiently flexible to operatively engage with and disengage from an engagement portion of the first member 202 as the arm 281a flexes toward and away from the first member 202. In other embodiments, the arm 281a may be operatively connected with the insertion housing 280. For example, the arm 281a may be adapted to pivot about a point 281c to allow the arm 281a to operatively engage with and disengage from the first member 202 as the arm 281 pivots toward and away from the engagement portion of the first member 202. The engagement portion may be, but is not limited to, an aperture, a ridge, an undersurface (or upper surface), a protrusion, a tab, an arm, a bias member, or any other suitable structure or mechanism arrangeable to allow the arm 281 to engage and/or disengage.

The insertion housing 280 may contain a main chamber 287 in alignment with the opening 240b. The insertion housing 280 may have a longitudinal dimension and an insert structure 260 located within the insertion housing 280. The insert structure 260 may be moveable along the longitudinal dimension in a direction L at least between a first position and a second position. The insert structure 260 may include a first part 262 and a second part 264 operatively connected to the first part 262 so that the first part 262 and the second part 262 may move together along the longitudinal dimension of the insertion housing 280. The insert structure 260 may be biased toward or otherwise held in the first position until sufficient force is applied to the insert structure 260 to move or otherwise actuate the insert structure 260 to the second position.

Various examples of suitable structures for insert structures are described in U.S. patent application Ser. No. 11/645,435, filed Dec. 26, 2006, entitled "Infusion Medium Delivery System, Device And Method With Needle Inserter And Needle Inserter Device And Method," which is assigned to the assignee of the present invention and is incorporated herein by reference in its entirety. Further examples of various insert structures are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in its entirety. Other examples of suitable structures for insert structures are described herein.

The first part 262 of the insert structure 260 may include a plunger head 288 and a needle 246 supported by the plunger head 288. The second part 264 of the insert structure 260 may include a collar 268 and a cannula 248 supported by the collar 268. The plunger head 288 may be connected to the collar 268. The first part 262 and the second part 264 may be configured to be removably attachable from each other, for example, in a friction fit engagement, snap fit engagement, or the like. For example, one of the plunger head 288 and the collar 268 may include protrusions or the like and the other of the plunger head 288 and the collar 268 may include apertures for receiving the protrusions.

The cannula 248 may extend at least partially through the collar 268. The cannula 248 may be fixed to the collar 268 to move with movement of the insert structure 260. The cannula 248 may have a hollow central channel 248c extending along a longitudinal length of the cannula 248 and open at one end 248a that may be adjacent a sharp end 246a of the needle 246 disposed within the cannula 248 as will be discussed. An end 248b of the cannula 248 opposite the open end 248a may have a head 249 having a larger radial dimension than a shaft portion 248d of the cannula 248.

A septum 266 may be supported or otherwise retained by the collar 268. The septum 266 may be a resealable member made of silicone, plastic, rubber, or the like. The septum 266 may be arranged between the plunger head 288 and the collar 268. The septum 266 may be pierceable by the needle 246.

The needle 246 may be arranged to extend through at least a portion of the cannula 248. The needle 246 may be supported by, secured, or operatively connected to the plunger head 288 to move with movement of the insert structure 260. Thus, in some embodiments, the plunger head 288 and the needle 246, which may be both part of the first part 262 of the insert structure 260, and the collar 268 and the cannula 248, which may be both part of the second part 264 of the insert structure 260, may be moveable at least between a first position and a second position.

In the second position, the needle 246 and the cannula 248 may extend through the opening 240b of the channel 240 and at least partially through the channel 240. As such, the sharp end 246a of the needle 246 and at least a portion of the length of the cannula 248 may extend out the opening 240a of the channel 240, for example, into skin of a user-patient.

The collar 268 of the insert structure 260 may have a suitable shape and size to fit into the channel section 242 of the channel 240 when the insert structure 260 is moved to the second position, for example, by an actuation device, as will be discussed later. In particular embodiments, the collar 268 may include one or more protrusions 267 and/or indentations that engage with one or more corresponding indentations, such as the aperture 205a, and/or protrusions in the injection site section 205 to provide a friction fit, snap fit, or the like, to lock or retain the second part 264 within the injection site section 205 upon the insert structure 260 being moved to the second position.

In further embodiments, instead of or in addition to engaging protrusions and indentations, one or more other mechanical structures may be employed to provide a suitable retaining function for retaining the second part 264 in place within the injection site section 205 upon the insert structure 260 being moved to the second position, for example, by an actuation device, including, but not limited to, a friction fit structure, snap fit structure, or the like.

In various embodiments, the arm 281a of the insertion housing 280 may be actuated to disengage the insertion housing 280 automatically from the first member 202 upon the insert structure 260 being moved to the second position. For example, the arm 281a may be adapted to flex or pivot away from the insertion housing 280 to disengage the first member 202 when the insert structure 260 is moved to the second position. In moving to the second position, one of the protrusions 267 may push against the end 281b of the arm 281a located in the aperture 205a. This may displace the end 281b of the arm 281 and release the arm 281a and/or the locking surface 281d from the retaining surface 205b from the first member 202. Accordingly, in such embodiments, the insertion housing 280 may be removed. In some embodiments, removal of the insertion housing 280 may also remove the first part 262 that may include the needle 246 and the plunger 288, while leaving the second part 264 that may include the cannula 248 and the collar 268 engaged to the injection site section 205.

The collar 268 may have a connection channel 269 provided in fluid flow communication with an opening (not shown) in the cannula 248 in fluid flow communication with the hollow central channel 248c of the cannula 248. Accordingly, the connection channel 269 may be in fluid flow communication with the hollow central channel 248c of the cannula 248. The connection channel 269 may be provided along the collar 268 at a location at which the connection channel 269 may align with the fluid conduit 224 when the insert structure 260 has been moved to the second position. Thus in some embodiments, in a case where the first member 202 and the second member are brought together (e.g., FIG. 9) and the insert structure 260 is in the second position, a fluid flow path may be established between the reservoir in the second member and the cannula 248 via the fluid conduit 224 and the connection channel 269.

In some embodiments, the insertion housing 280 may include an inner housing portion 284 concentrically arranged within an outer housing portion 281. The inner housing portion 284 may have an inner chamber 285 in alignment with the chamber 287 in which the insert structure 260 may be arranged for movement. A lip portion 284a or the like extending from the inner housing portion 284 may be for containing the insert structure 260 in the inner chamber 285. For example, the insert structure 260 may be in contact with or otherwise adjacent the lip portion 284a when the insert structure 260 is in the first position.

The outer housing 281 may have an outer chamber 282 between the outer housing 281 and the inner housing portion 284. The outer chamber 282 may be for receiving at least a portion of an actuation device for actuating the plunger head 288 as will be described. In various embodiments, the inner housing portion 284 may be integral with the outer housing portion 281. In other embodiments, the inner housing portion 284 may be separate and connected with the outer housing portion 281.

As previously discussed, in various embodiments, the insert structure 260 (i.e., the plunger head 288, the needle 246, the collar 268, and the cannula 248) may be actuated to move to the second position by an actuation device 290. The actuation device 290 may include a housing 291 securable to the insertion housing 280. A suitable connection structure may be provided on the actuation device 290 and/or the insertion housing 280 to provide a manually releasable connection between those components. In some embodiments, the connection structure may include, but is not limited to, a threaded extension on one or the other of the actuation device 290 and the insertion housing 280 and a corresponding threaded receptacle on the other of the insertion housing 280 and the actuation device 290 for receiving the threaded extension in threaded engagement.

For example, an end 272 of a distal portion 270 of the actuation device 290 may be adapted to be insertable into the insertion housing 280, for example, within the outer chamber 282. The distal portion 270 may have a threaded portion 276 for threaded engagement of a threaded portion 282a within the insertion housing 280. The end 272 may be insertable into the outer chamber 282 of the insertion housing 280, for example, until a surface 271 of the actuation device 290 abuts a lip portion 283 of the insertion housing 280 and/or the end 272 contacts a floor 284b of the insertion housing 280.

In other embodiments, other suitable connection structures may be employed. Such a connection structure may include, but is not limited to, friction-fitted sections of the insertion housing 280 and the actuation device 290, flexible pawls or extensions on one or the other of the actuation device 290 and the insertion housing 280 and a corresponding aperture, stop surface, or the like on the other of the insertion housing 280 and the actuation device 290.

The housing 291 may contain an internal chamber 292 having a longitudinal dimension and a member 298 arranged within the housing 291. The member 298 may be moveable in the direction L at least between a first position (e.g., FIG. 19) and a second position. The housing 291 may include a drive mechanism for actuating the member 298. The drive mechanism may be a bias member 293, such as, but not limited to, a coil spring, or the like, arranged within the internal chamber 292 of the housing 291. The bias member 293 may be configured to impart a bias force on the member 298 when the member 298 is in the first position to urge the member 298 toward the second position.

In some embodiments, an activation structure, such as a trigger, button, or the like, may be provided to control the actuation device 290. In further embodiments, a first trigger 294 may be configured to arm or prepare the actuation device 290 for firing or otherwise moving the member 298 to move the insert structure 260. For example, the first trigger 294 may be pressed to retract the member 298 to the first position. As such, the first trigger 294 may be adapted to selectively arm the member 298 and/or the bias member 293 into the first position (i.e., the retracted position).

A second trigger 297 or the like may be configured to selectively release the member 298 and/or the bias member 293 to allow the member 298 to move in the direction L under the force of the bias member 293 to the second position. In other embodiments, the first trigger 294 may be configured to selectively release the member 298 and/or the bias member 293 to allow the member 298 to move in the direction L under the force of the bias member 293 to the second position upon being operated after the actuation device 290 has been armed. For example, pressing the first trigger 294 a first time may retract the member 298 to the first position, and pressing the first trigger 294 a second time may release or otherwise allow the member 298 to advance to the second position. Other examples of insertion structures are described in U.S. Pat. Pub. No. US 2007/0142776, entitled "Insertion Device for an Insertion Set and Method of Using the Same," which is herein incorporated by reference in its entirety.

In yet further embodiments, a first locking mechanism (not shown) may be provided such as, but not limited to, a manually moveable projection, lever, slider, or the like. The first locking mechanism may be connected to or extending through the housing 291 and engaging the member 298 (or other structure holding the member 298) in a releasable manner to selectively hold the member 298 in the retracted position, for example after the first trigger 294 has been operated, against the bias force of the bias member 293.

In some embodiments, the actuation device 290 may be configured to allow the member 298 to be moved from the second position at least toward the first position automatically or upon manipulation by the user, for example, to a third position or a neutral position (e.g., position of the member before being moved to the first position when the actuation device is armed). That is, after the member 298 has been moved to the second position (e.g., an extended position), the member 298 may be moved to a third position automatically or upon manipulation of the actuation device 290 by the user-patient. The third position may be any suitable position at which the needle 246 is sufficiently withdrawn, for example, from the skin of the patient, as will be discussed, such as, but not limited to, the first position, a position between the first and second positions, or the like.

For example in some embodiments, the housing 291 may include a second chamber 295. The second chamber 295 may be concentrically arranged relative to the internal chamber 292, for example around the internal chamber 292. A drive mechanism may be arranged within the second chamber 295 of the housing 291 to move the member 298. The drive mechanism may be a second bias member 296, such as, but not limited to, a coil spring, or the like, arranged to impart a bias force on the member 298 when the member 298 is in the second position to urge the member 298 toward third position. Thus, in some embodiments, the member 298 can be moved to the first position (e.g., by pressing the first trigger 294), moved to the second position (e.g., by pressing the second trigger 297), and then automatically moved to a third position.

In some embodiments, an activation structure, such as a trigger (e.g., first trigger 294, second trigger 297, or a third trigger (not shown)), button or the like, may be provided to control movement of the member from the second position to the third position. Thus, in some embodiments, the member 298 can be moved to the first position (e.g., by pressing the first trigger 294), moved to the second position (e.g., by pressing the second trigger 297), and then further moved to a third position (e.g., by pressing the first trigger 294, the second trigger 297, or the like).

In yet further embodiments, a second locking mechanism (not shown) may be provided such as, but not limited to, a manually moveable projection, lever, slider, or the like. The second locking mechanism may be connected to or extending through the housing 291 and engaging the member 298 (or other structure holding the member 298) in a releasable manner to selectively hold the member 298 in the second position, for example after the second trigger 297 has been operated, against the bias force of the second bias member 296.

In various embodiments, the member 298 may be adapted to operatively engage the plunger head 288, for example, when the actuation device 290 is connected to the insertion housing 280. The member 298 or a portion thereof may be made of a sufficiently rigid material, but having a certain amount of flexibility. A protrusion, extension, arm, or the like may be provided on one or the other of the member 298 and the plunger 288 and a corresponding aperture, protrusion, extension, arm or the like on the other of the plunger 288 and the member 298 for engaging each other. For example, in particular embodiments, the member 298 may have one or more arms 299 for engaging a head portion 289 of the plunger head 288 upon the actuation device 290 being connected to the insertion housing 280.

Thus in some embodiments, in a case where the member 298 is operatively engaged with the plunger head 288 and the member 298 is actuated, the insert structure 260, which may include the plunger head 288, the needle 246, the collar 268, and the cannula 248, may be moved to the second position. Similarly as previously described, the member 298 can be further actuated to move the first part 262 of the insert structure 260, which may include the plunger head 288 and the needle 246, away from the first position (e.g., to (or toward) the first position and/or the third position). Thus, the second part 464 of the insert structure 260, which may include the collar 268 and the cannula 248, may remain in the second position to allow fluid to flow from the reservoir though the fluid conduit 224 and the connection channel 269 to the cannula 248 into the user-patient as previously described.

In various embodiments, the actuation device 290 may be configured for improved handling of the actuation device 290 by the user-patient. For example, the actuation device 290 may include a handling portion 255, grips, textured surfaces, or the like that may aid in handling of the actuation device 290.

FIG. 21 illustrates a flowchart describing use of the system 200 (e.g., FIGS. 17-20) according to an embodiment of the present invention. With reference to FIGS. 17-21, the system 200 may be operated according to process 1000. In step S1010, the base 206 of the first member 202 may be secured to skin of a user-patient at a suitable injection location with, for example, but not limited to, adhesive material, or the like. Examples for securing the first member to the skin of the user-patient are described herein and can be found in U.S. patent application Ser. No. 11/645,435, filed Dec. 26, 2006, entitled "Infusion Medium Delivery system, Device And Method With Needle Inserter And Needle Inserter Device And Method" and U.S. patent application Ser. No. 12/027,963, filed Feb. 7, 2008, entitled "Adhesive Patch Systems and Methods," all of which are herein incorporated by reference in their entirety. Alternatively or in addition, the base 206 may be secured to the user-patient by one or more other suitable structures, including, but not limited to, straps, or the like.

Once the base 206 is suitably secured the user-patient at a suitable injection location, in step S1020, the insertion housing 280 may be affixed to the inject site section 205. Then, in step S1030, the actuation device 290 may be connected to the insertion housing 280 to operatively engage the member 298 with the plunger 288. Then in step S1040, the actuation device 290 may be actuated, for example by actuating one or more of the first trigger 294 and the second trigger 297, to move the member 298 to the second position.

In step S1042, the member 298 may move the insert structure 260, which may include the plunger 288, the needle 246, the collar 268, and the cannula 248, to the second position. As a result, in step S1044, the needle 246 may pierce the skin of the user-patient allowing a portion of the cannula 248 to enter the user-patient. In step S1046, the insert structure 260 may engage the inject site section 205 to retain the cannula 248 within the user-patient. The cannula 248 and collar 268 may be retained in the second position by engagement of, for example, the collar 268 and the injection site section 205, as previously described. As the insert structure 260 engages the inject site section 205, in step S1048, the insert structure 260 may cause the insertion housing 280 to disengage from the first member 202.

Next in step S1050, with the cannula 248 and the body 268 locked in the second position, the actuation device 290 may be further actuated, for example automatically or by operating one of the triggers, to cause movement of the member 298 to the third position. In step S1052, the member 298 may cause the first part 262 of the insert structure 260, which may include the plunger head 288 and the needle 246, to move away from the second part 264 of the insert structure 260 (e.g., toward the first position). The second part 262 of the insert structure 260 may remain in the inject site section 205 and the cannula 248 within the user-patient. In step S1060, the second member may be attached to the first member 202 to provide a fluid flow path from the reservoir of the second member to the user-patient via the fluid conduit 224, the connection channel 269 in the collar 268 of the insert structure 260, and the cannula 248. In other embodiments, such a flow path may be for conveying fluid from the user-patient to the reservoir.

A connection sequence (e.g., the sequence of connecting the actuation device 290 to the injection site section 205, connecting the first member 202 to the second member, attaching the base 206 of the first member 202 to the skin of the user-patient, etc.) for connecting various components may be different for different embodiments. For example, in some embodiments, the user-patient may be provided with a first member 202 having a base 206, a housing 204, and an injection site section 205 in a pre-connected state with the actuation device 290. In this manner, the user-patient need not have to connect the actuation device 290 to the housing 204 as those parts are supplied to the user in a pre-connected state, for example, from a manufacturing or assembly facility. In such embodiments, the base 206 of the first member 202 may be secured to skin of the user-patient at a suitable injection location. After securing the base 206 to the skin of the user-patient, the actuation device 290 may be activated to cause the insert structure 260 to move to the second position so that the needle 246 can pierce the skin of the user-patient.

While the connection sequence in some of the above embodiments involve securing the base 206 of the first member 202 to the user-patient prior to connection of the second member to the first member 202, in other embodiments, the second member may be connected to the first member 202, as described above, prior to securing the base 206 of the first member 202 onto the skin of the user-patient. In such embodiments, the first member 202 and the second member may be connected together and, thereafter, may be secured to the user-patient, for example, by adhering one or both of the first member 202 and the second member to the skin of the user-patient. In addition, while the connection sequence in the above embodiments involve activating the actuation device 290 prior to the connection of the second member to the first member 202, in other embodiments, the second member may be connected to the first member 202, as described above, prior to activating the actuation device 290.

In some embodiments, the receptacle 210 may be in the first member 202 and a connection portion may be in the second member. In other embodiments, the receptacle 210 may be in the second member, for example, in or associated with a housing for a reservoir, and the connection portion may be in the first member 202, for example, in or associated with a housing containing an injection site structure.

Returning to FIGS. 17-20, in some embodiments, the system 200 may be configured to detect that the cannula 248 is properly positioned, for example, in the extended position or other desired position after operation by the actuation device 290.

In some embodiments, the insertion housing 280 may be provided with a first interactive element 265. The injection site section 205 or other portion of the first member 202 (e.g., the base 206) may be provided with a second interactive element 207. The first interactive element 265 and the second interactive element 207 may be configured to interact with each other in a detectable manner when in sufficiently close proximity to each other. As detailed in the disclosure, interaction between the various elements, such as (but not limited to) between the first interactive element 265 and the second interactive element 207, may include (but is not limited to) engaging of the elements, contact between the elements, application of a force (e.g., pressure) of one element on the other element, application of energy (e.g., electrical charge, magnetic charge, heat, etc.), and/or any suitable exchange between the elements that is detectable. In other embodiments, the insertion housing 280 may be provided with the second interactive element 207 and the injection site section 205 may be provided with the first interactive element 265. However, it should be noted that one or both of the first interactive element 265 and the second interactive element 207 may be provided in any suitable component and/or along any suitable location of the system 200. For example, the first interactive element 265 could be arranged in the actuation device 290. As another example, the second interactive element 207 could be arranged on the base 206 or component connected to the base 206. As a further example, both the first interactive element 265 and the second interactive element 207 could be arranged in the insertion housing 280.

The first interactive element 265 may be arranged in a fixed relation to the insertion housing 280, for example, by attaching, forming, or otherwise supporting the first interactive element 265 to a suitable location on a wall or on other structure of or in the insertion housing 280. In some embodiments, the first interactive element 265 may be provided on the collar 268 or other portion of the insertion housing 280 movable by the actuation device 290. The second interactive element 207 may be arranged in a fixed relation to the second member 202, for example, by attaching, forming, or otherwise supporting the second interactive element 207 to a suitable location on a wall or on other structure of or in the second member 202.

In some embodiments, the second interactive element 207 may be arranged on the second member 202 to be relative to the first interactive element 265 on the insertion housing 280 in a case where the insertion housing 280 and the second member 202 are connected or otherwise operatively engaged and the cannula 248 is properly positioned. Accordingly, the first interactive element 265 and the second interactive element 207 are properly positioned (i.e., at expected locations) relative to each other. As such, the first interactive element 265 and the second interactive element 207, for example, may interact with each other in a case where the insertion housing 280 and the second member 202 are connected or otherwise operatively engaged and the first interactive element 265 and the second interactive element 207 are properly positioned relative to each other.

An interaction between the first interactive element 265 and the second interactive element 207 (or between any other interactive element discussed in the disclosure) may occur in a case where the cannula 248 is positioned at a predefined position. The predefined position of the cannula 248, for example, may correspond to an extended position (e.g., the extended position E of FIG. 16) of the cannula 248, for example, after being moved or otherwise actuated by the actuation device 290. Once the cannula 248 is the extended position, the cannula 248 may be connected in fluid-flow communication with the reservoir of the second member 202 via the fluid conduit 224 and the connection channel 269. In some embodiments, the predefined positioned of the cannula 248 may be with respect to alignment in one or more dimensions (e.g., along the X-, Y-, and/or Z-axis).

In various embodiments, the first interactive element 265 and the second interactive element 207 may be similar types of devices. For instance, in some embodiments, the first interactive element 265 may be configured to interact with second interactive elements (e.g., the second interactive element 207) and/or the second interactive element 207 may be configured to interact with first interactive elements (e.g., the first interactive element 265).

In some embodiments, the first interactive element 265 and the second interactive element 207 may be dissimilar types of mechanisms. For example, the first interactive element 265 may be a ferrous conduit and the second interactive element 207 may be a magnet.

In some embodiments, suitable electronics may be connected to the first interactive element 265 and/or second interactive element 207 to provide a controlled power signal to selectively activate or otherwise control one or more of the first interactive element 265 and the second interactive element 207 and/or other components as described throughout the disclosure.

In various embodiments, some or all of the interactive elements (e.g., the first interactive element 265, the second interactive element 207) may be integrated with the insertion housing 280 and the second member 202 and/or be separate components placed in or on the insertion housing 280 and the second member 202. For example, the interactive elements may be placed in or on the insertion housing 280 and the second member 202 in a friction-fitting manner, during a molding a process, and/or the like. In some embodiments, one or more of the interactive elements may be insert mold labeled on its respective part. In some embodiments, a film cover may be provided for supporting one or more of the interactive elements.

In various embodiments, some or all of the interactive elements may have an exposed surface. The exposed surface of the interactive elements may be for allowing increased interactivity between each of the interactive elements. In other embodiments, some or all of the interactive elements may be covered, for example (but not limited to) being disposed completely within the insertion housing 280 and/or the second member 202. Such embodiments may allow for protecting the interactive elements from damage, debris collection, mitigating interference with other components (e.g., other interactive elements, electronics in the system 200, and/or the like), and/or the like.

Throughout various embodiments, the first interactive element 265 and the second interactive element 207 may be configured to interact such as, but not limited to, when the first interactive element 265 and the second interactive element 207 align in one dimension or more than one dimension, are sufficiently proximate to each other, contact each other, an electrical or magnetic connection is established between the components, and/or the like. Any one or combination of these events may occur, for example, in a case where the cannula 248 is positioned in a predetermined manner otherwise within an operating threshold (e.g., in the extended position).

In other embodiments, the first interactive element 265 may be arranged on the insertion housing 280 at a location to interact electronically (or magnetically) with the second interactive element 207 in a case where the cannula 248 is extended and the first interactive element 265 and the second interactive element 207 are in relative close proximity to each other, such as, but not limited to, in contact with each other. In some embodiments, suitable electronics may be connected to at least one of the first interactive element 265 and the second interactive element 207 to provide a controlled power signal to selectively activate or otherwise control the first interactive element 265 and/or the second interactive element 207.

In some embodiments, one or more additional first interactive elements and/or one or more additional second interactive elements may be provided on the insertion housing 280 and the second member 202 respectively, for example, to provide a more reliable detection of the cannula 248. For instance, a pair of second interactive elements 207 may be arranged to face each other to detect a single first interactive element 265. As another example, a pair of second interactive elements 207 may be arranged to interact with a respective first interactive element 265. In other embodiments, the one or more additional first interactive elements and/or the one or more additional second interactive elements may be arranged on different components than those in which the first interactive element 265 and the second interactive element 207 are provided, respectively. Examples of such arrangements are disclosed in (but are not limited to) U.S. application Ser. No. 12/649,619, filed Dec. 29, 2009, which is herein incorporated by reference in its entirety.

Thus in various embodiments, as part of a process of placing a medical delivery device in fluid communication with a user, the user may place a base 206 of the medical delivery device adjacent skin of the user, attach a insertion housing 280 to the base 206, attach an actuation device 290 to the insertion housing 280, and actuate the actuation device 290 to extend a cannula 248 to an extended position to put the user in fluid-flow communication with a reservoir of the medical delivery device. Accordingly, a first interactive element 265 and a second interactive element 207 may interact with each other to determine, for example, whether the 248 is properly positioned.

In some embodiments, the interactive elements (e.g., the first interactive element 265, the second interactive element 207) may be configured to help a user-patient properly position the cannula 248 or otherwise ensure that the cannula 248 is properly positioned. For example, the first interactive element 265 and the second interactive element 207 may be arranged at one or more appropriate locations on the insertion housing 280 and the second member 202 (or other suitable components) to allow an indicator or indicator device 420 (e.g., FIG. 44) associated with the system 100 to provide an indication when the cannula 248 is properly positioned.

In some embodiments, a conductive medium 207*a* may be at a position adjacent one of the interactive elements, for example the second interactive element 207, or otherwise in communication with the interactive elements to allow the conductive medium 207*a* to function as a conductor for the interactive element. In such embodiments, the interactive element may interact with the conductive medium 207*a* to allow the conductive medium 207*a* to be have similar characteristics or properties, though not necessarily exactly the same characteristics or properties, as the interactive element. For example, a magnetic second interactive element 207 may provide a magnetic charge to a magnetic conductive medium 207*a*. The conductive medium 207*a* may be made of a material, such as, but not limited to, an electrically conductive material (e.g., metal, graphite, salt solutions, plasma, and/or the like), a magnetically attractive material (e.g., metal), and/or the like. In some embodiments, the conductive medium 207*a* may be a sufficiently high thermally conductive material (e.g., metal, or any other material with a thermal conductivity, for example (but not limited to), above 1), and/or the like.

In further embodiments, the conductive medium 207*a* may be arranged on its respective part (e.g., the second member 202) to allow the interactive element (e.g., the second interactive element 207) to interact with the other interactive element (e.g., the first interactive element 265) on the opposing part (e.g., the insertion housing 280) via the conductive medium 207*a* in any of the manners described throughout the disclosure. For example, in particular embodiments, the first interactive element 265 may interact with the conductive medium 207*a* in a case where the cannula 248 is positioned properly. Accordingly, the first interactive element 265 and the second interactive element 207 may interact with each other via the conductive medium 207a. Thus, some embodiments may allow the first interactive element 265 to interact with the conductive medium 207a in addition to or alternative to the second interactive element 207. For example, a magnetic second interactive element 207 may magnetize a magnetically attractive conductive medium 207a, which may then interact with the first interactive element 265.

In some embodiments, the conductive medium 207a may be arranged at a position adjacent the other interactive element (e.g., the first interactive element 265) or otherwise in communication with the other interactive element to allow the conductive medium 207a to function as a conductor for the other interactive element. In further embodiments, the conductive medium 207a may be arranged on its respective part to allow the other interactive element to interact with the interactive element (e.g., the second interactive element 207) on the opposing part via the conductive medium 207a in any of the manners described throughout the disclosure. For example, in particular embodiments, the second interactive element 207 may interact with the conductive medium 207a in a case where the cannula 248 is properly positioned. Accordingly, the first interactive element 265 and the second interactive element 207 may interact with each other via the conductive medium 207a. Thus, some embodiments may allow for second interactive element 207 to interact with the conductive medium 207a in addition to or alternative to the first interactive element 265. For example, an electrical connection between the first interactive element 265 and the second interactive element 207 may be established upon the second interactive element 207 contacting the conductive medium 207a (e.g., electrically conductive medium).

In some embodiments, the indicator 420 may be configured to provide an indication corresponding to a type of position of the cannula 248, for example, that the position of the cannula 248 is within a most preferred range, an acceptable range (i.e., acceptable, but not most preferred), and/or the like. In some embodiments, the indicator may be configured to provide an indication corresponding to various stages of movement of the cannula 248, for example, that the cannula 248 has not yet moved from the first position (e.g., as shown in FIG. 18), the cannula 248 has moved from the first position, but has not reached the extended position, the cannula 248 is at the extended position, the cannula 248 has moved beyond the extended position, the cannula 248 is or is not moving, and/or the like.

In various embodiments, one or more of the interactive elements (e.g., the first interactive element 265, the second interactive element 207, and/or the like) may be a spring, finger, or other bias member for contacting one or more of the other interactive elements upon the cannula 248 being moved to the extended position. In such embodiments, the one or more of the interactive elements may be made of a suitably rigid material, such as, but not limited to, metal, plastic, glass, composite materials, rubber, and/or the like. Examples of such configurations are disclosed in (but are not limited to) U.S. application Ser. No. 12/649,619, filed Dec. 29, 2009, which is herein incorporated by reference in its entirety.

In various embodiments, more than one interactive element (e.g., the first interactive element 265, the second interactive element 207, and/or the like) may be spaced apart from each other on one of the insertion housing 280 and the second member 202. At least one of the more than one interactive element (e.g., second interactive element 207) or a portion thereof may be movable by a portion (e.g., first interactive element 265, a finger, pusher, and/or the like) of the other of the insertion housing 280 and the second member 202 upon the cannula 248 being moved to the extended position. Examples of such configurations are disclosed in (but are not limited to) U.S. application Ser. No. 12/649,619, filed Dec. 29, 2009, which is herein incorporated by reference in its entirety.

In some embodiments, for example, the first interactive element 265 and the second interactive element 207 can be arranged on one of the insertion housing 280 and the second member 202 to be spaced apart and movable relative to each other in a manner such as that previously described. In such embodiments, for instance, a portion of the other of the insertion housing 280 and the second member 202, such as a tab, finger, and/or the like, may be arranged to urge the first interactive element 265 and the second interactive element 207 toward each other to allow the interactive elements to interact (e.g., contact) with each other. Thus in such embodiments, most or all of the interactive elements may be provided on one of the housing portions, for example in the injection site section 205 of the second member 202, which may allow for reuse of the interactive elements. In other embodiments, the movable interactive element may be any suitable intermediary member configured to be movable relative to one or more of the interactive elements in a manner as described in the disclosure. Accordingly, movement of the intermediary member may allow for interaction (e.g., an electrical connection) between the first interactive element 265 and the second interactive element 207.

In other embodiments, the movable interactive element (or a portion thereof) may instead be a flexible layer, such as a film made of a suitably flexible material including, but not limited to, a Mylar and/or the like, that can be pushed upon by the portion of the opposing part to contact the other interactive element. In further embodiments, the flexible layer may be a conductive layer, such an electrically conductive medium (e.g., metal and/or the like), magnetically conductive medium (e.g., a ferrous conduit), thermally conductive medium, and/or the like.

In various embodiments, the interactive elements (e.g., the first interactive element 265, the second interactive element 207, and/or the like) may allow for, but is not limited to, tracking a number of times of use, a number of times a component has been connected to and/or disconnected from other components, verifying proper connection and/or alignment of components in a medication delivery system prior to each delivery step, checking, sensing, and/or measuring parameters, such as ambient parameters (e.g., ambient magnetic fields), operating parameters, and/or the like, alerting users to conditions, such as conditions outside operating parameters of the delivery system, and/or the like.

Various embodiments may employ different arrangements of interactive elements on its respective components. For instance, in embodiments in which one of the components is intended to be disposable (e.g., disposed of after one or a prescribed number of uses or period of use), some of the interactive elements may be provided on the disposable part, while other interactive elements may be provided on a durable part (i.e., not intended to be disposed). As a result, after a period of usage, the interactive element(s) on the disposable part that may have attracted and collected stray material can be disposed of with the disposable part.

On the other hand, the interactive element(s) on the durable part can be sufficiently clean and free (or be cleaned) of stray material for further usage. In such embodiments, arranging at least some of the interactive element(s) on the durable portion may provide certain advantages, such as, but not limited to, being more cost-effective, for example, by arranging interactive elements on respective parts based on cost; easier to manufacture and/or install, and/or the like. For example, electronics and circuitry (as discussed in the disclosure), such as, but not limited to, a sensor, a responsive device, and/or other circuitry or electronics, may be arranged on the durable part.

In yet other embodiments, arranging at least some of the interactive element(s) on the disposable portion may provide certain advantages, such as, but not limited to, maintenance, cost, and/or the like. For example, such embodiments may allow for the interactive element(s) that have worn down, been contaminated, or otherwise collected stray material to be disposed of with the disposable part.

In some embodiments, at least one of the first interactive element 265 and the second interactive element 207 may be a suitable sensor for sensing the other of the first interactive element 265, the second interactive element 207, or other element, such as the conductive medium 207a operatively connected to or otherwise associated with the other of the first interactive element 265 and the second interactive element 207. Accordingly, upon the sensor detecting the presence of the other of the first interactive element 265 and second interactive element 207, the system may determine whether the cannula 248 has been properly positioned. Such embodiments may be used in addition to or alternatively of embodiments in which a first interactive element interacts with a second interactive elements, for example, as described in the disclosure.

In various embodiments, suitable electronics may be connected to the sensor and/or the other of the first interactive element 265 and the second interactive element 207 to provide a controlled power signal to selectively activate or otherwise control the sensor and/or the other of the first interactive element 265 and the second interactive element 207. For example, the sensor may be controlled to activate upon connecting to the actuation device 290, a manual activation of a control button, switch, or other manual operator on one of the connectable components or on a remote-controller device (not shown) connected in wireless communication with the sensor through suitable control electronics. As another example, the sensor may be controlled to activate automatically after a certain action, such as activation of a button, and/or the like or after a certain amount of time. In some embodiments, the sensor may be controlled to activate upon activation or insertion of a particular component or device, such as, but not limited to, connecting to the actuation device 290.

Examples of various needle insertion tools are described in the disclosure and also in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in their entirety. Thus, in such examples, the sensor may be activated, for example, before or after, the cannula 248 is extended so that a determination can made whether the cannula 248 is properly positioned.

In some embodiments, the sensor may be activated upon interacting with the other of the first interactive element 265 and the second interactive element 207. In some embodiments, an activating element, such as an activating magnet and/or the like, may be provided on at least one of the insertion housing 280 and the second member 202. The activating element may activate the sensor upon interacting with each other, for example by contacting each other as the cannula 248 is extended. In particular embodiments, the activating element may be one of the interactive elements.

The sensor may be any suitable detector configured to detect a detectable feature, such as an interactive element (e.g., the first interactive element 265, the second interactive element 207, and/or the like) or a presence of an interactive element, such as a magnetic field, electric field, and/or the like provided by the interactive element. In further embodiments, the sensor may be configured to and/or associated with electronics configured to produce an electronically detectable state or signal upon detecting the detectable feature. For example, the sensor may be a sensor pad and/or the like configured to sense, detect, and/or otherwise interact with an interactive element upon the interactive element being in sufficient proximity (e.g., in contact) with the sensor pad. In certain embodiments, the sensor may include a conventional activating switch or a conventional device capable of detecting a particular detectable feature such as an interactive element (e.g., the first interactive element 265, the second interactive element 207, and/or the like) or a presence of an interactive element, such as a magnetic field, electric field, and/or the like provided by the interactive element.

In some embodiments, the sensor may be configured to sense, detect, or measure a presence of the interactive element. For example, such embodiments may allow for the sensor to sense a presence (e.g., a magnetic field) of the interactive element rather than the element itself. In particular, the sensor may be configured to sense, detect, or measure, but is not limited to, magnetic fields; electric fields; temperature or heat; optical and/or visual features (e.g., barcodes, colors, grayscale, and/or the like); tactile features; audio features; radio frequencies (RF) or other radio signals; ultraviolet light, or other light; force; torque; resistances (e.g., coded resistance pattern); capacitances; inductances; ultrasonic signals, and/or the like; and/or the like provided by, emitted from, produced by, or otherwise present in an interactive element.

For example, the sensor may be configured to sense a magnetic field emitted by a magnetic first interactive element 265 to determine whether the cannula 248 is properly positioned. If the sensor fails to detect the magnetic field provided by the magnetic first interactive element 265, then this may indicate that the cannula 248 is not properly positioned. On the contrary, if the sensor detects the magnetic field provided by the magnetic first interactive element 265, then this may indicate that the cannula 248 is properly positioned (e.g., the cannula 248 is extended to a location within a certain tolerance).

In further embodiments, the sensor may be configured to measure a value or presence parameter, magnitudes, changes, gradients, polarities, vectors, field directions, and/or any other measurable parameter suitable for detecting and/or measuring a detectable feature. For example, the sensor may be configured to measure a gauss level of a magnetic field provided by the first interactive element 265.

In various embodiments, the detectable feature (e.g., the first interactive element 265) may be selected, configured, and/or arranged to provide a particular detectability (i.e., a characteristic or trait capable of being detected) such that, for example, the interactive element and/or the presence of the interactive element may be sensed by the sensor only when the first cannula 248 is properly positioned. For instance, a magnetic first interactive element 265 may be selected to provide a magnetic field having a particular gauss level that may be detectable by the sensor only if the sensor is sufficiently located relative to the magnetic first interactive element 265, which would occur, for example, if the cannula 248 is properly positioned.

Alternatively or in addition, the sensor may be selected, configured, and/or arranged to provide a sensitivity or otherwise control an amount sensed of the detectable feature by the sensor. Thus, for instance, the interactive element and/or the presence of the interactive element may be sensed by the sensor only when the cannula 248 is properly positioned; otherwise, the detectable feature would not be sufficiently proximate to the sensor to be detectable by the sensor. For instance, a sensor may be configured to sense, for example, a first interactive element 265 or field thereof only if sufficiently proximate to the magnetic first interactive element 265.

Such embodiments may allow, for example, for a lesser tolerance in positioning the cannula 248. Accordingly, such embodiments may be used in a case where positioning of the cannula 248 needs (but not limited to) more precision. In other embodiments, the sensor may have an increased sensitivity or the like. Such embodiments may allow, for example, for a greater tolerance in positioning the cannula 248.

In some embodiments, the sensor or other associated circuitry may be configured such that a detection not meeting a certain range (e.g., below the range or above the range) or threshold may be ignored or otherwise determined to be unacceptable by the sensor (or other associated circuitry). Thus, in such embodiments, a case where the sensor does not detect the interactive element and/or the presence of the interactive element, the sensor (or other circuitry) may provide an indication that the cannula 248 is not properly positioned.

In yet further embodiments, the sensor and/or other associated electronics may be configured such that a detection not meeting a certain range or threshold (i.e., determined to be unacceptable) may provide an indication that the detection does not meet the certain range or threshold. For example, such an indication may indicate that the cannula 248 has been extended, but has not reached the proper depth or position.

In some embodiments, other interactive elements or structures may be provided to regulate the sensing and/or measuring ability of the sensor and/or the detectability and/or measurability of the detectable feature. For instance, a heat-emitting first interactive element 265 may be at least partially surrounded by a low thermally conductive material, such as plastic, rubber, wood, and/or the like. This may allow a heat-sensing sensor to sense the heat-emitting first interactive element 265 and/or a suitable presence thereof only when the cannula 248 is properly positioned, thus substantially preventing a false detection of heat that may be emitted, for example, laterally from the heat-emitting first interactive element 265.

In various embodiments, one of the interactive elements may have a capacitance that is measurable. Another interactive element (or other component) may be configured to affect the capacitance of the one of the interactive elements, for example, by being brought in proximity or contact with the one of the interactive elements. The affected capacitance of the one of the interactive elements may be measured or otherwise detected by the sensor to indicate a change in state, for example, when the cannula 248 is properly positioned.

In various embodiments, one of the interactive elements may have an inductance that is measurable. Another interactive element (or other component) may be configured to affect the inductance of the one of the interactive elements, for example, by being brought in proximity or contact with the one of the interactive elements. The affected inductance of the one of the interactive elements may be measured or otherwise detected by the sensor to indicate a change in state, for example, when the cannula 248 is properly positioned.

In some embodiments, one or more additional sensors interactive elements may be provided on the insertion housing 280 and the second member 202 respectively, for example, to provide a more reliable detection of the cannula 248. For instance, a pair of sensors may be arranged to face each other to detect a single first interactive element 265. As another example, a pair of sensors may be arranged to interact with a respective first interactive element 265. In other embodiments, the one or more additional sensors may be arranged on different components than those in which the first interactive element 265 and the second interactive element 207 are provided, respectively. Examples of such arrangements are disclosed in (but are not limited to) U.S. application Ser. No. 12/649,619, filed Dec. 29, 2009, which is herein incorporated by reference in its entirety.

In some embodiments, both the first interactive element 265 and the second interactive element 207 may each be a sensor. In such embodiments, the one or more of the sensors may be configured to detect the other sensor and/or other interactive element(s). For example, the cannula 248 may be determined to have been positioned properly in a case where (but not limited to) one of the sensors detects the other sensor, the sensors both detect each other, at least one of the sensors detects an interactive element, the sensors both detect a same (or different) interactive element, and/or the like.

In further embodiments, further sensors may be provided for detecting other sensors (and/or interactive elements). In such embodiments, the cannula 248 may be determined to have been positioned properly, but is not limited to, upon one or more or a predetermined amount of the sensors detecting a particular or any of the other sensors, the sensors detecting each other, at least one of the sensors detecting an other interactive element, the sensors detecting a same (or different) interactive element and/or the like.

In various embodiments, one or more additional sensing structures, such as those described in the disclosure, may be provided to properly position the cannula 248, for example, to increase reliability of cannula 248 positioning and/or decrease time for sensing proper positioning of the cannula 248.

Thus in various embodiments, as part of a process of placing a medical delivery device in fluid communication with a user, the user may place a base 206 of the medical delivery device adjacent skin of the user, attach a insertion housing 280 to the base 206, attach an actuation device 290 to the insertion housing 280, and actuate the actuation device 290 to extend a cannula 248 to an extended position to put the user in fluid-flow communication with a reservoir of the medical delivery device. Accordingly, a sensor (e.g., second interactive element 207) may detect a detectable feature (e.g., first interactive element 265) to determine, for example, whether the cannula 248 is properly positioned.

Further examples of arrangements of sensors for detecting detectable features (e.g., interactive elements, conductive medium, etc.) or the like are disclosed in (but are not limited to) U.S. application Ser. No. 12/649,619, filed Dec. 29, 2009, which is herein incorporated by reference in its entirety.

In various embodiments, the interactive element(s) (e.g., first interactive element 265, second interactive element 207, conductive medium 207a, sensors) and the like need not be used or otherwise limited to two housing portions. Examples of interactive elements arranged among three or more housing portions are disclosed in (but are not limited to) U.S. application Ser. No. 12/649,619, filed Dec. 29, 2009, which is herein incorporated by reference in its entirety.

Thus various embodiments may allow for verification of multiple distinct and separate components or steps, verification of correct positioning of multiple distinct and separate components, a safety mechanism to provide notification of separation (intentional or accidental) of any individual component in a multi-component system, and/or the like. For instance, an interactive element positioned in each of the actuation device 290, the insertion housing 280, and the second member 202 may allow for a determination that the actuation device 290 has been properly connected to the insertion housing 280 and a determination that the cannula 248 has been properly positioned upon actuation of the actuation device 290.

In various embodiments, the system may include at least one responsive device (not shown) configured to provide an electronically detectable state or signal in response to an interaction (or lack thereof) between two or more interactive elements (e.g., the first interactive element 265, the second interactive element 207, the conductive medium 207a, the sensor, etc.). Thus, in some embodiments, a responsive device may be configured to provide a signal in a case where the cannula 248 is properly positioned. The signal may indicate, for example, the two or more interactive elements have interacted, and thus the cannula 248 is properly positioned. Examples of configurations using at least one responsive device are disclosed in (but not limited to) U.S. application Ser. No. 12/649,619, filed Dec. 29, 2009, which is herein incorporated by reference in its entirety. Thus, for instance, the responsive device.

In various embodiments, the responsive device, the sensor, and/or other interactive element(s) may be connected in electrical communication with control electronics (not shown). The control electronics may be incorporated within the control electronics for controlling a drive device 44 (e.g., FIG. 4) such as, but not limited to, the control electronics 52 (e.g., FIG. 4) for controlling the drive device 44. Alternatively, the control electronics may be separate from and in addition to the control electronics 52, but connected in electrical communication with the control electronics 52 and/or the drive device 44 to provide a drive control signal to the drive device 44. More specifically, the control electronics may be configured to inhibit operation of the drive device 44, unless the responsive device (or the like) provides a signal or a change in state to the control electronics. For instance, as previously discussed, the responsive device 410 may provide such a signal or a change in state upon being activated by an interactive element, for example, when the cannula 248 is properly positioned. In other words, the drive device 44 may be inoperable unless the cannula 248 is properly positioned.

In particular embodiments, the control electronics may include a wake-up function that allows the drive device 44 (or other component) to remain in a first mode (e.g., low-power mode) until the responsive device (or the like) provides a signal or a change in state to the control electronics, for example, upon proper positioning of the cannula 248. Upon providing the signal or the change in state to the control electronics, the drive device 44 (or other component) may switch from the first mode to a second mode.

In some embodiments, the control electronics may provide a detect signal such as, but not limited to an electronic signal, flag setting, or other indicator to the control electronics 52 and/or the drive device 44 upon activation of the responsive device (or the like) by an interactive element. In such embodiments, the control electronics 52 and/or the drive device 44 may be configured to allow operation of the drive device 44 only upon the presence of the detect signal.

In further embodiments, in which multiple responsive devices (and/or the like) are used, the control electronics may be configured to provide a detect signal, for example, to allow operation of the drive device 44 only upon an activation of all or a predefined number or set of the responsive devices (and/or the like). In yet further embodiments, the control electronics may be configured to provide a detect signal, for example, to allow operation of the drive device 44 only upon an activation of all or a predefined number or set of the responsive devices (and/or the like) in a particular order. Such embodiments may allow, for example, for connection of components in a particular sequence, orientation, and/or in a particular direction, as well as performance of steps in a particular sequence, and/or the like.

The control electronics and/or the control electronics 52 (e.g., FIG. 4) may be configured to control the drive device 44 (e.g., FIG. 4) in various manners in accordance with various embodiments of the invention. For instance, the drive device may be controlled to prevent pumping (delivery) operation unless the cannula 248 is properly positioned. Or for instance, the drive device 44 may be controlled to stop pumping (delivery) operation upon a detection of an interruption of a fluid-flow path or a disconnection of a critical component, for example, if the cannula 248 is dislodged from the proper position.

In alternative or in addition, the control electronics and/or the control electronics 52 (e.g., FIG. 4) may be configured to detect a first-time proper positioning of the cannula 248 or other first-time action, as compared to a re-positioning of the cannula 248 after previous or partial usage. In this manner, the drive device 44 may be controlled to provide a priming operation or other suitable first-time operation(s) upon detection of a first-time proper positioning. As another example, the drive device 44 may be controlled to prevent a delivery even if the cannula 248 is properly positioned if it has been determined that the cannula 248 has moved out of the proper position (e.g., outside the skin of the user-patient) and back to the proper position.

In yet further embodiments, the system may include additional sensors, responsive devices, and/or the like connected for electrical communication with the control electronics. Such additional sensors, responsive devices, and/or the like may comprise magnetically and/or electronically actuating switches, magnetic and/or electric field magnitude and direction sensors, inductive sensors, other proximity sensors, contact sensors, and/or the like for providing a detectable signal or change in a state upon properly positioning the cannula 248 or upon predetermined action. Such predetermined actions may comprise, for example, one or more of a proper connection of a reservoir into a housing portion or base, a proper connection of a conduit to a reservoir, a proper connection of two conduits together, a proper setting of a needle or cannula in an inserted state, a proper connection of a conduit to a cannula or needle, or a proper connection of other components of or to the system.

Alternatively, or in addition, the additional sensors, responsive devices, and/or the like may include or be one or more flow detectors for detecting the occurrence or blockage of a fluid flow path in the system. In such embodiments, the control electronics may be configured to provide a detect signal, for example, to allow operation of the drive device 44 only upon an activation of all or a predefined number or set of additional sensors, responsive devices, and/or the like or a proper state of the additional sensors, responsive devices, and/or the like.

In various embodiments, the system 200 is configured to determine whether the cannula 248 is properly positioned, for example, upon the cannula 248 being moved to the extended position by the actuation device 290. In further embodiments, the system 200 is configured to determine whether the cannula 248 is properly positioned each time a pump command is issued by the drive device 44 (or the like). Thus, for example, if the cannula 248 is not in position, the pump command is not issued or an issued pump command is not carried out.

Figure 44:
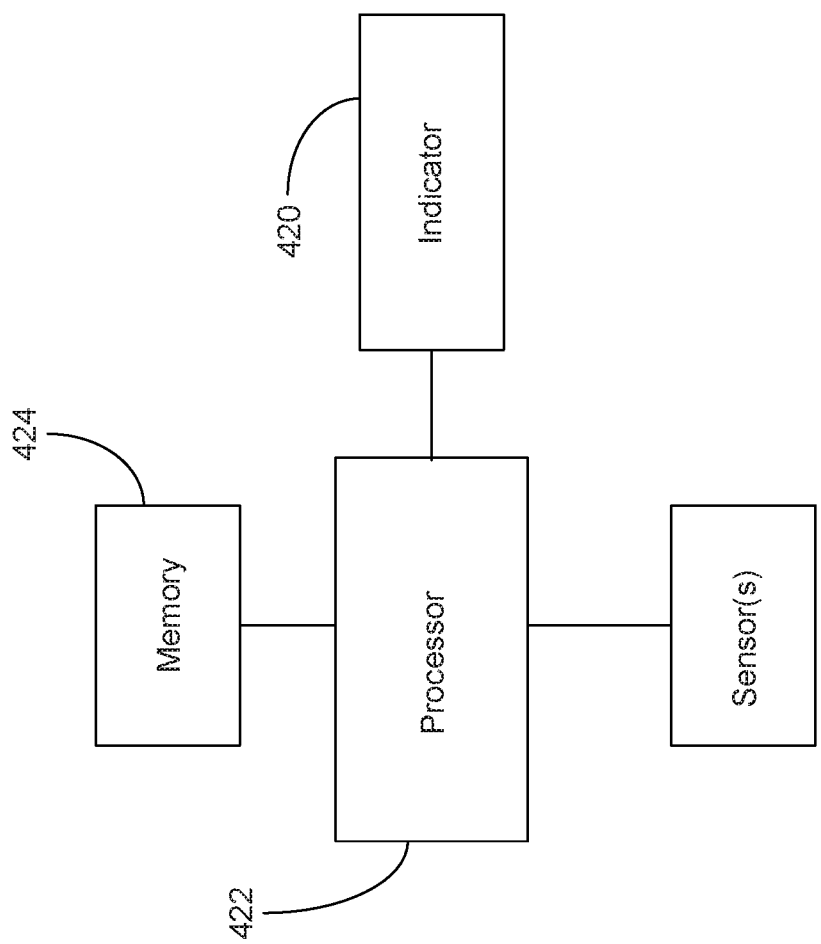
FIG. 44 is a block diagram of a portion of a medical device in accordance with an embodiment of the present invention.

In some embodiments, the control electronics 414 and/or the control electronics 52 (e.g., FIG. 4) may be configured to provide a user-perceptible indication of a proper positioning of the cannula 248 or other action, such as connecting the actuation device 290 to the insertion housing 280. For example, upon detection of a proper positioning of the cannula 248, the control electronics (or the control electronics 52) may provide a suitable control signal to activate an indicator device 420, as shown in FIG. 44.

The indicator device 420 may operated by a processor 422. The processor 422 may be configured to execute various programs and/or to process various information, such as data received from one or more sensors, responsive devices, and/or other interactive elements. The processor 422, for example, may be configured to compare detected signals with thresholds and/or pre-stored values in memory 424.

With reference to FIGS. 18-20 and 44, the indicator device 420 may include, but is not limited to, an audible indicator, an optical indicator, a tactile indicator, combinations of one or more those indicators, and/or the like. For example, upon positioning of the cannula 248 or other predetermined action as described above, an audible beeping sound or other suitable sound may be generated by a sound generating device in or associated the system. For example, upon properly positioning the cannula 248, a flashing light or other suitable visual indicator may be generated by an LED or other light source or a display device on or associated with the system. For example, upon properly positioning the cannula 248, a vibration and/or the like may be generated by a vibration device and/or the like in or associated with the system.

In some embodiments, one or more signals may be communicated from a transmitter (not shown) in the system to a remotely located communication device (not shown), such as, but not limited to, a hand-held controller, a computer, and/or the like. Accordingly, the transmitter may provide one or more of the above-noted user-perceptible indications to a user of the communication device. In some embodiments, a text or graphic message may be displayed on a display screen on the system and/or on the communication device as an indicator of a proper positioning of the cannula 248.

In various embodiments, the system 200 is configured to determine whether the cannula 248 is properly positioned, for example, in the extended position after operation by the actuation device 290 or other desired position. However, in other embodiments, the system 200 may be configured to determine (but is not limited to) whether the cannula 248 is at another position, such as the starting position (e.g., shown in FIG. 18), somewhere between the starting position and the extended position, or the like. In other embodiments, the system 200 may be configured to determine whether another component is properly positioned. For example, the system may be configured to determine (but is not limited to) whether the actuation device 290 is properly connected to the insertion housing 280, the insertion housing 280 is properly connected to the second member 202. In particular embodiments, the system 200 may be configured to determine whether a particular fluid connector is positioned properly (e.g., one that would allow for fluid-flow without leaking, exposure to contaminants, or the like). For example, the system 200 may be configured to determine whether the needle 124 (FIG. 8) is properly positioned in the reservoir housing 108 (FIG. 8) when the first member 102 (FIG. 8) is brought together with the second member 103 (FIG. 8).

In various embodiments, the system 200 may be configured to provide information relating to one or more of the interactive elements. For instance, in some embodiments, the detectable feature (or other interactive element) may include data, information, or the like that when detected by or otherwise interacting with the sensor (or other interact element), the sensor may detect the data. For example, a first cannula having a first length may provide first data and a second cannula having a second length (different from the first length) may provide second data. Accordingly, the sensor can detect whether the system 200 is using the first cannula or the second cannula based on the data the sensor detects.

In further embodiments, the system 200 may be configured to perform an action based on the detected data. For example, if the sensor detects the first cannula, the first cannula is properly positioned when the first cannula is positioned at a first location. If the sensor detects the second cannula, the second cannula is properly positioned when the second cannula is positioned at a second location different from the first location.

Thus in various embodiments, the system 200 may be configured to determine a type and/or characteristics of a cannula (or other appropriate component) being used. In such embodiments, for example, the system 200 may be configured to determine a length (and/or other dimension) of the cannula, material of the cannula, and/or the like.

Figure 22:
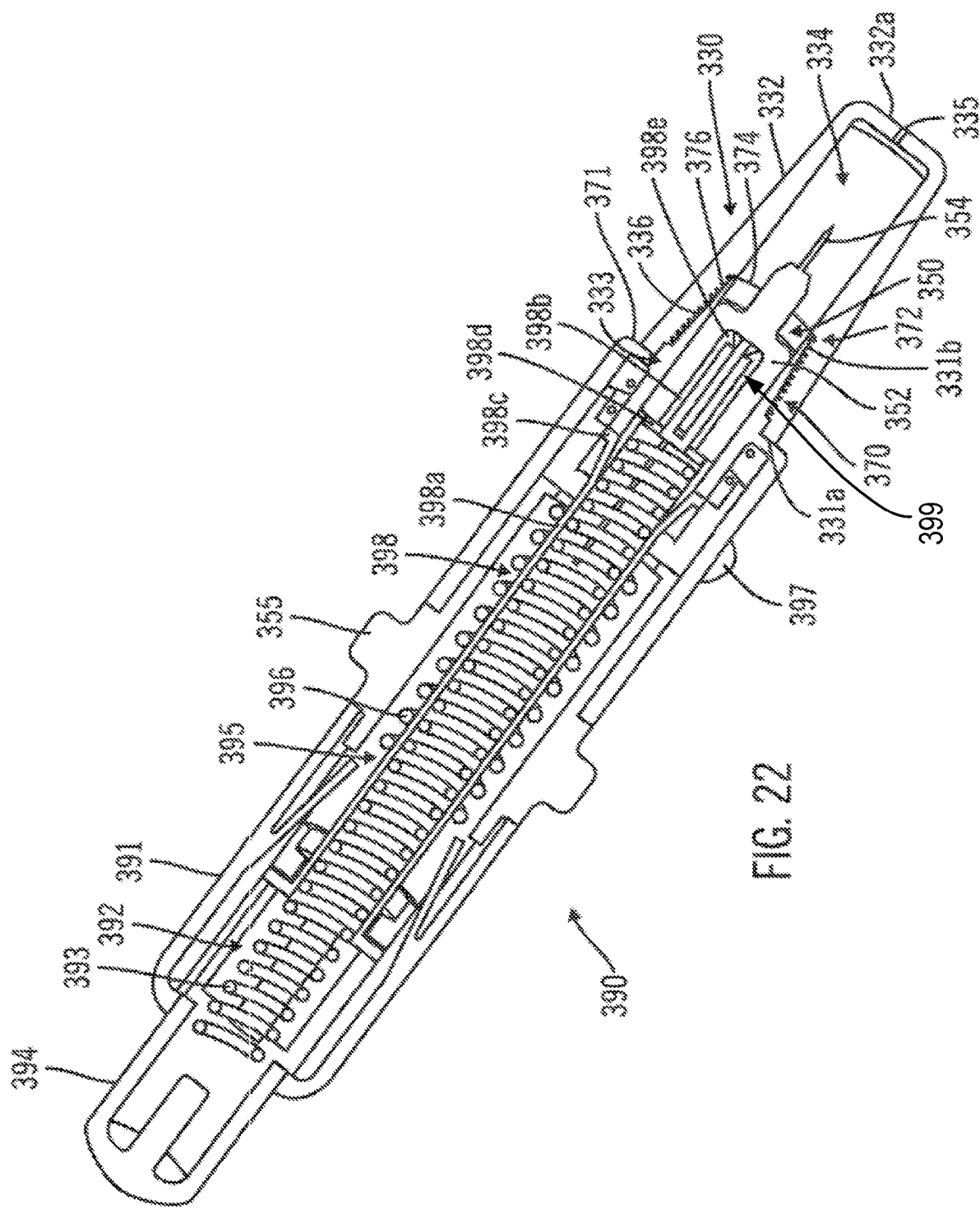
FIG. 22 illustrates a medial device in accordance with an embodiment of the present invention.
Figure 23:
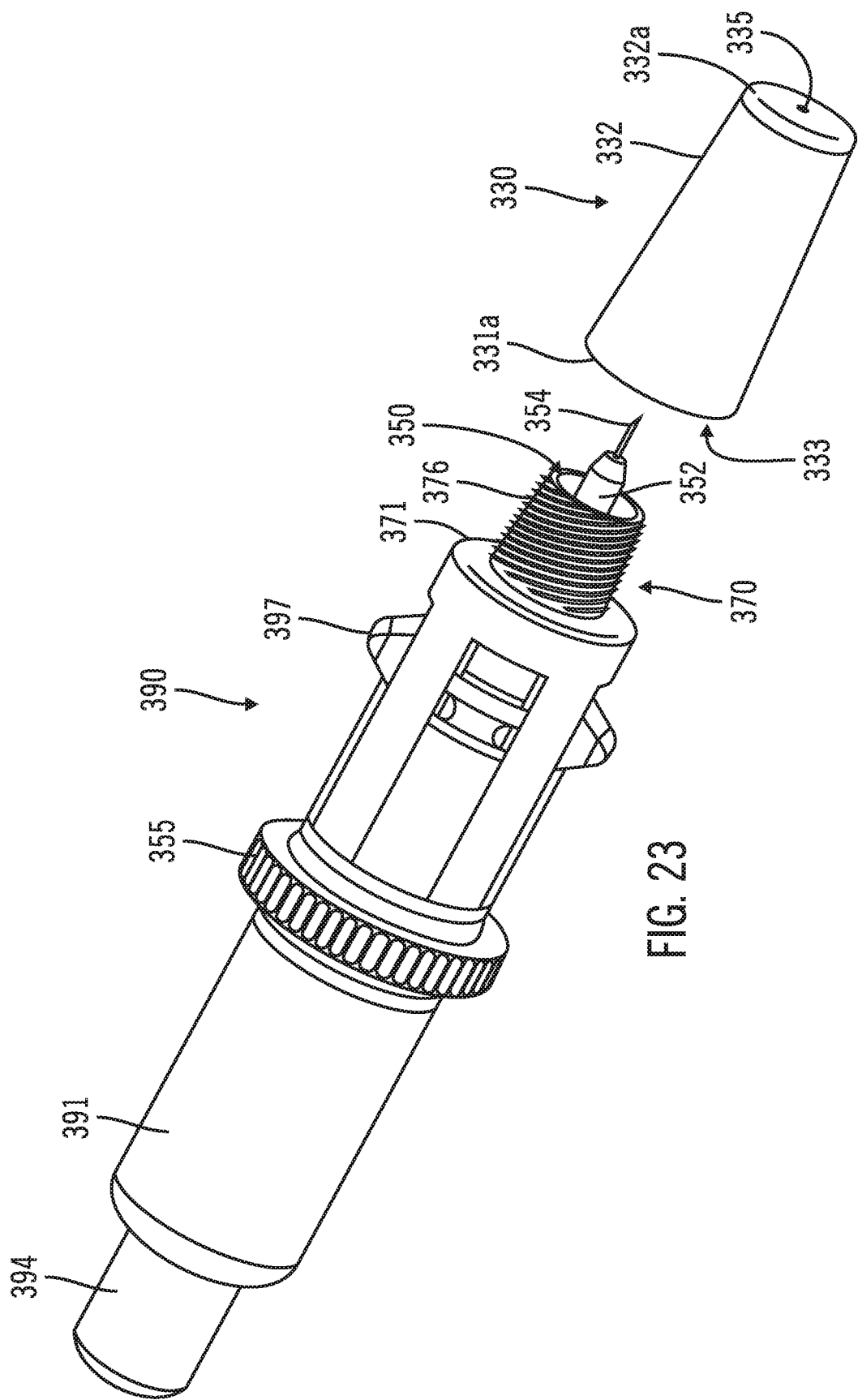
FIG. 23 illustrates a medial device in accordance with an embodiment of the present invention.
Figure 24:
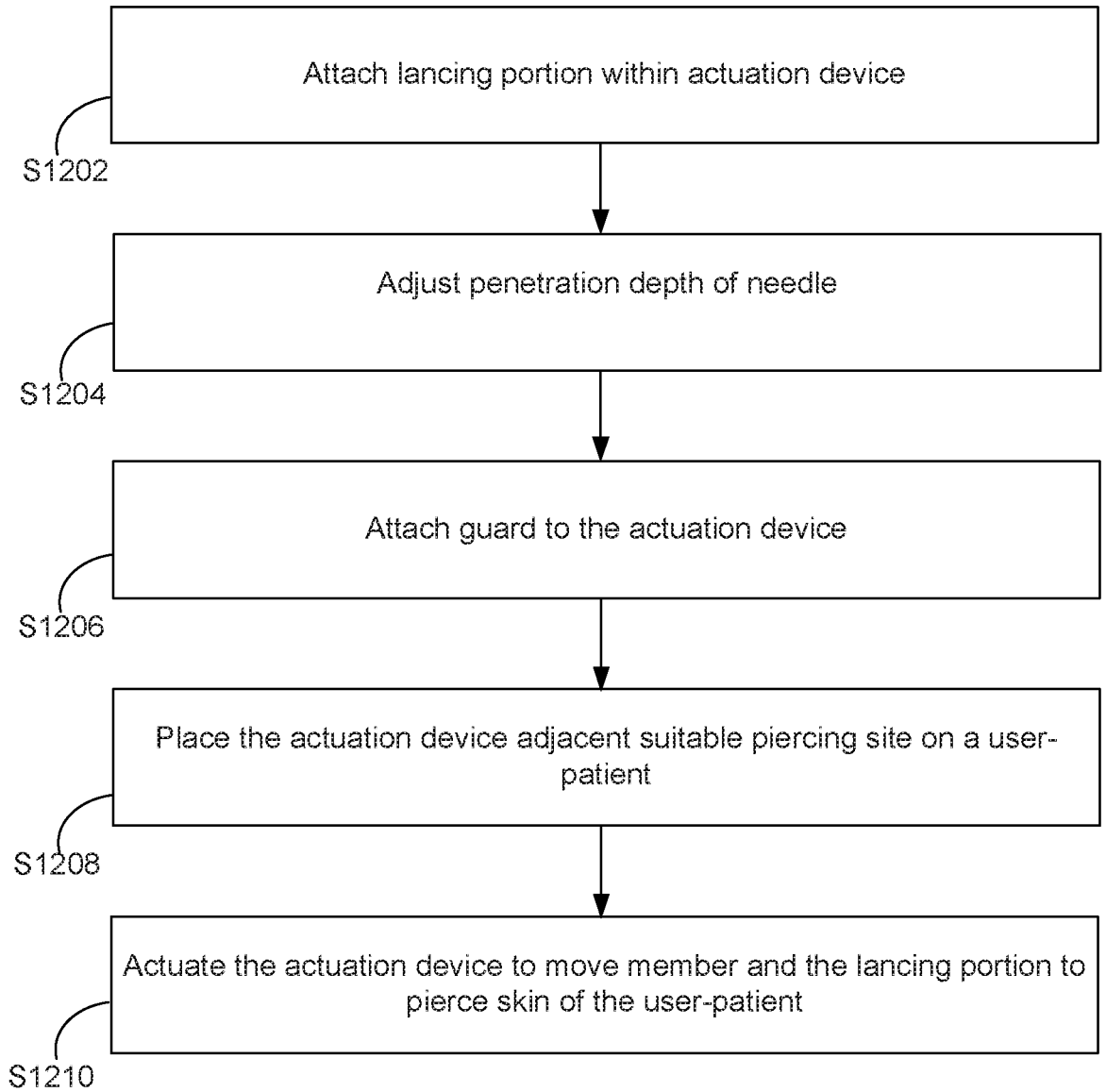
FIG. 24 illustrates flow chart for using a medial device in accordance with an embodiment of the present invention.
Figure 25:
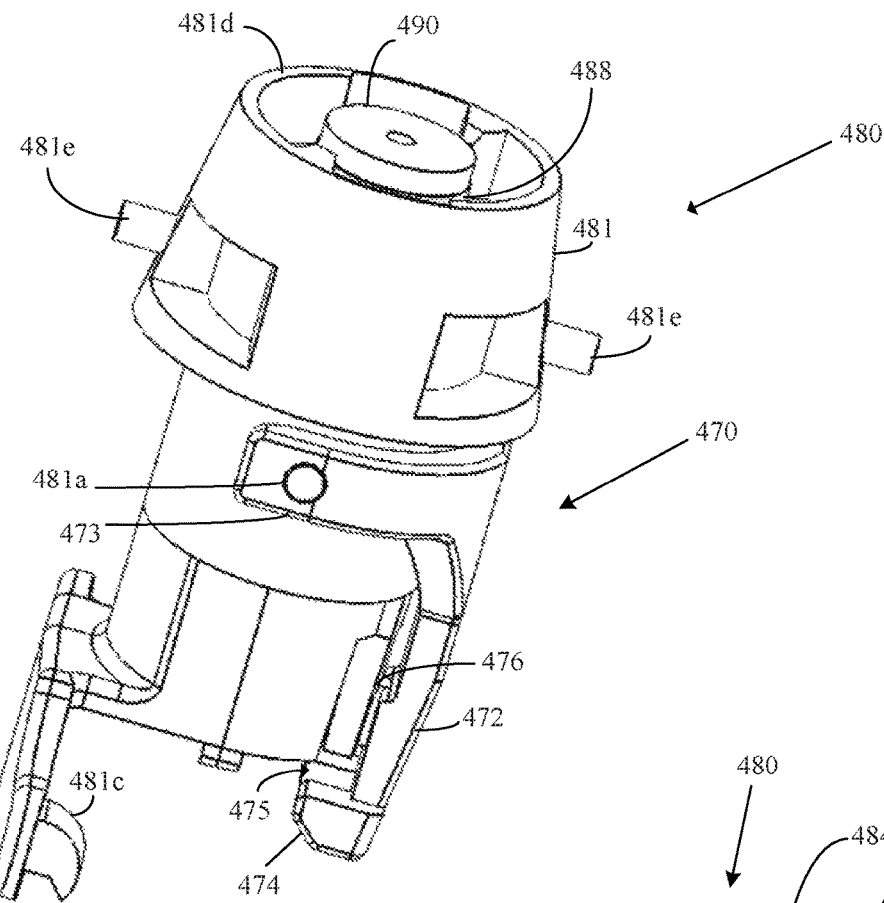
FIG. 25 illustrates a portion of a medial device in accordance with an embodiment of the present invention.
Figure 26:
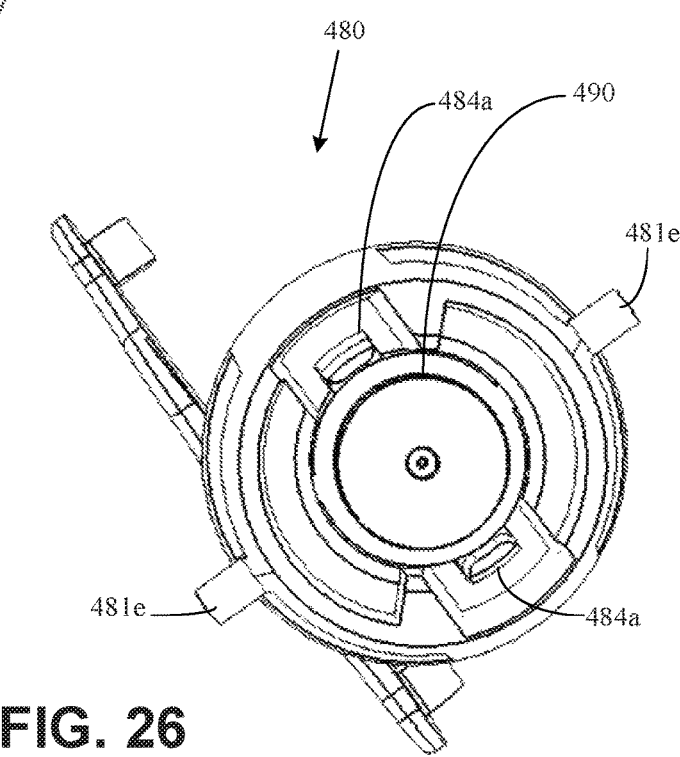
FIG. 26 illustrates a portion of a medial device in accordance with an embodiment of the present invention.
Figure 27:
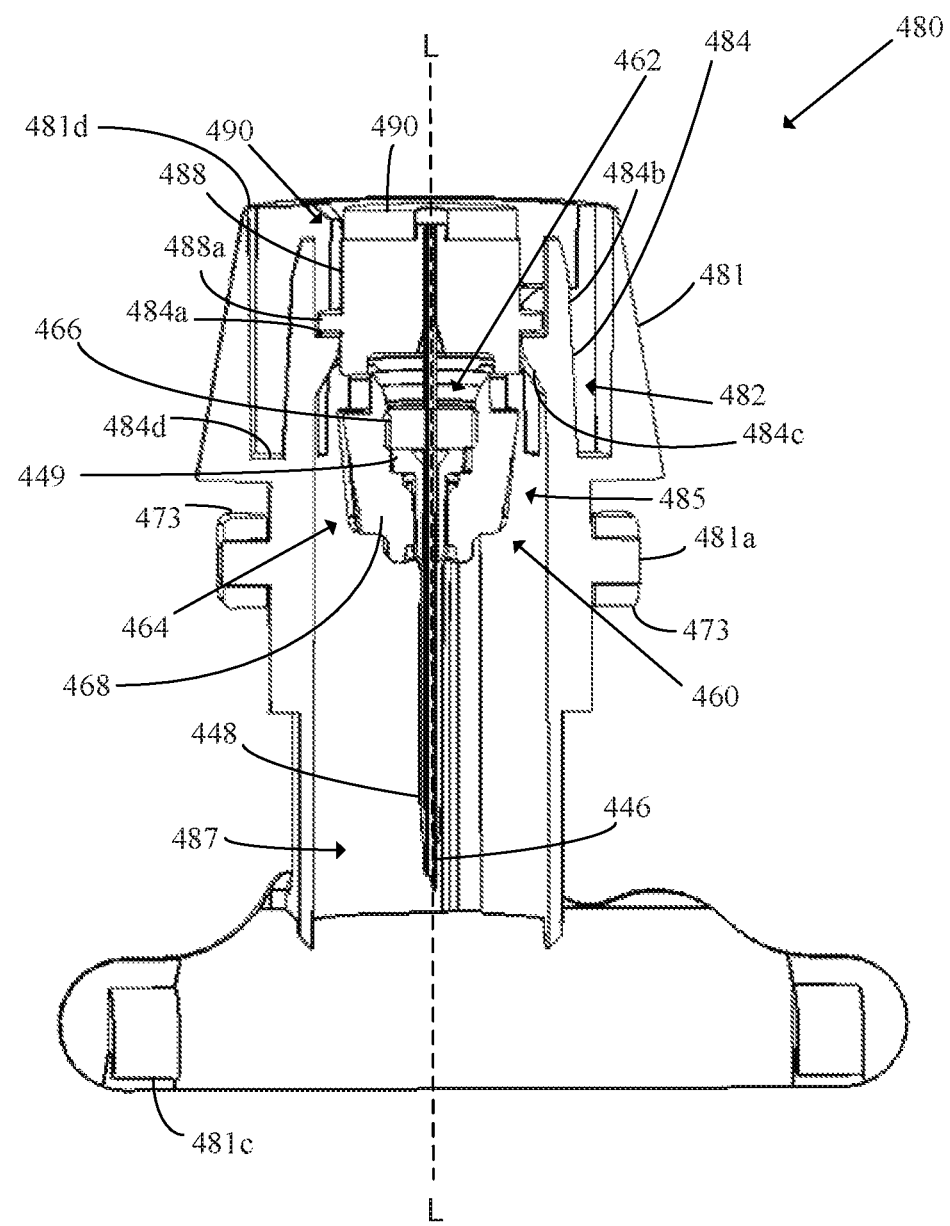
FIG. 27 illustrates a portion of a medial device in accordance with an embodiment of the present invention.
Figure 28:
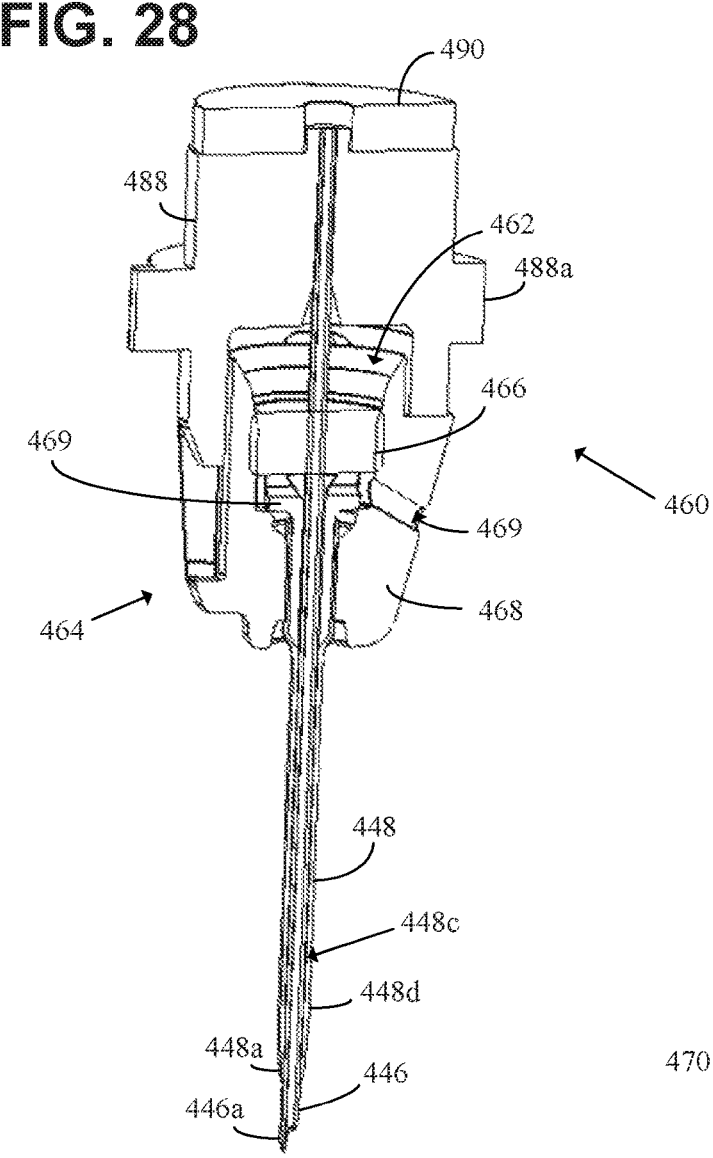
FIG. 28 illustrates a portion of a medial device in accordance with an embodiment of the present invention.
Figure 29:
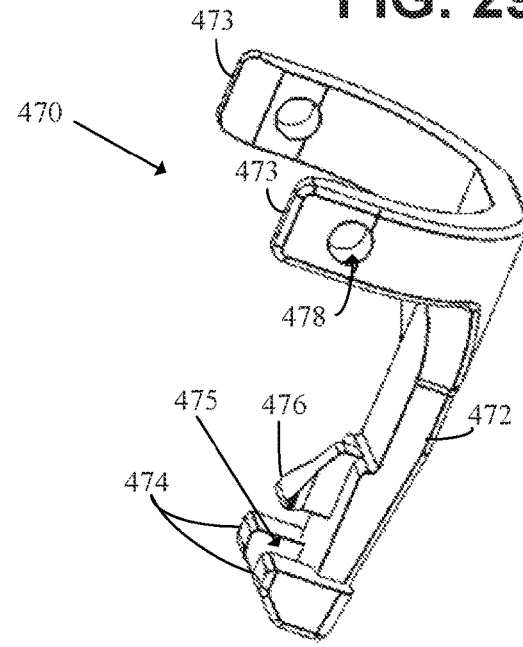
FIG. 29 illustrates a portion of a medial device in accordance with an embodiment of the present invention.
Figure 30:
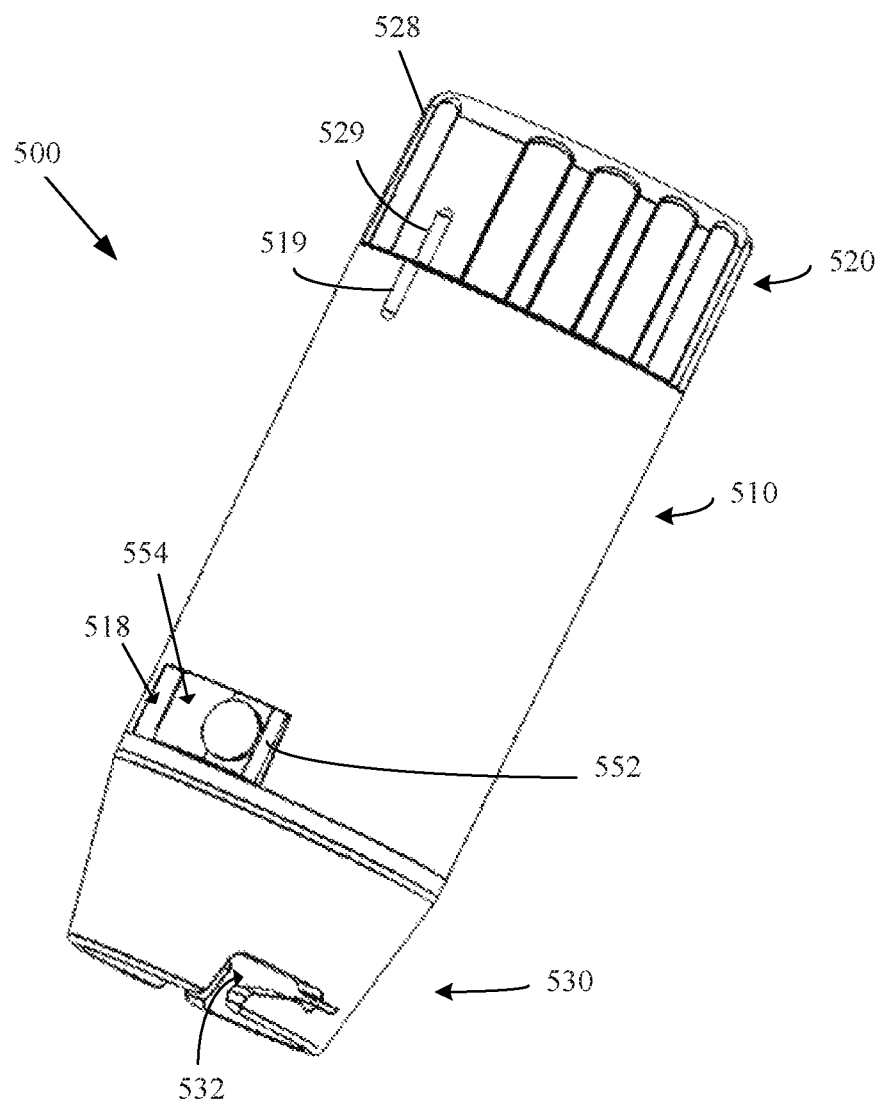
FIG. 30 illustrates a portion of a medial device in accordance with an embodiment of the present invention.
Figure 31:
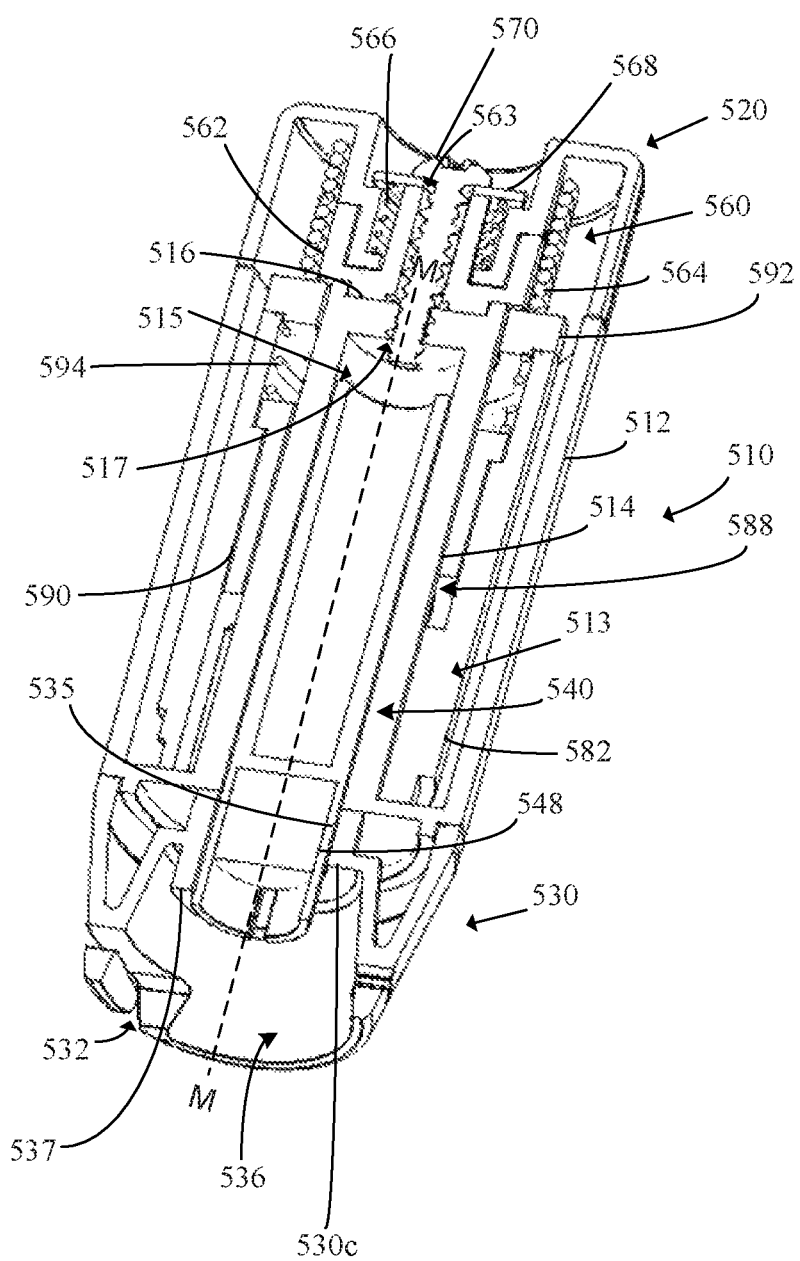
FIG. 31 illustrates a portion of a medial device in accordance with an embodiment of the present invention.
Figure 32:
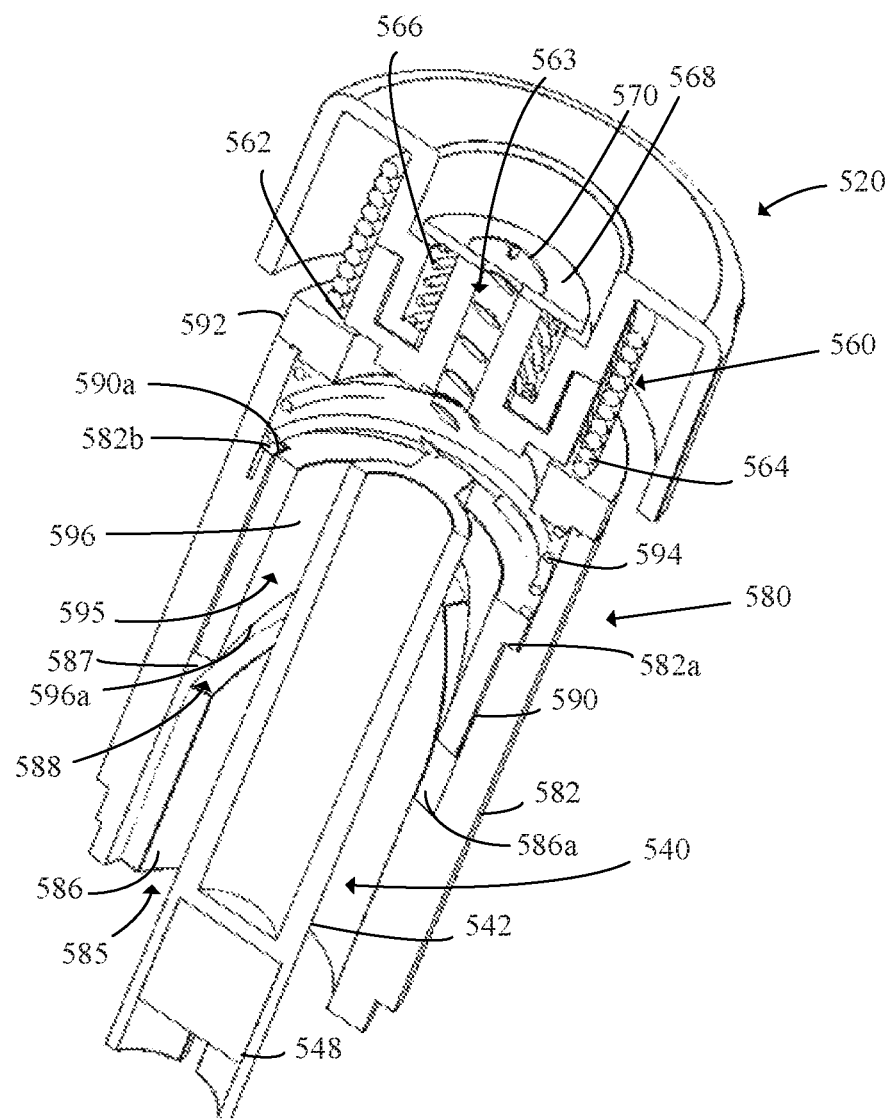
FIG. 32 illustrates a portion of a medial device in accordance with an embodiment of the present invention.
Figure 36:
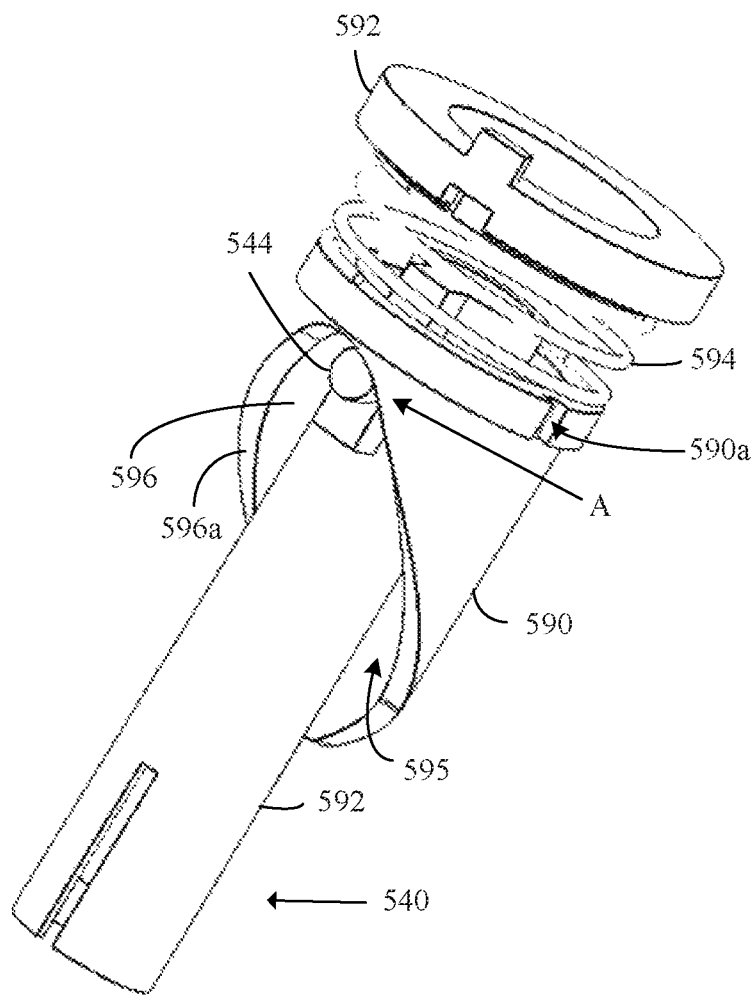
FIG. 36 illustrates a portion of a medial device in accordance with an embodiment of the present invention.
Figure 37:
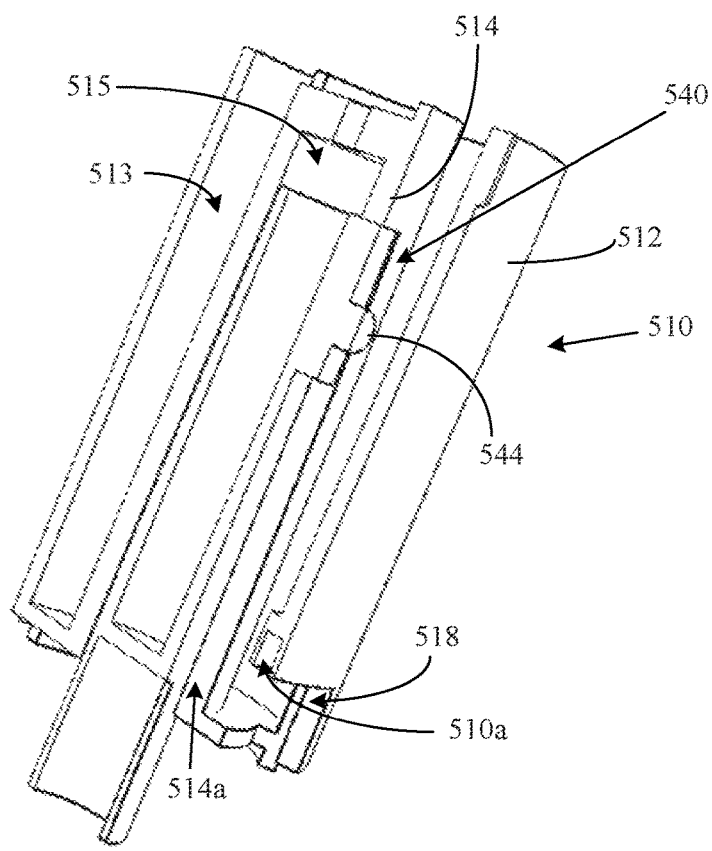
FIG. 37 illustrates a portion of a medial device in accordance with an embodiment of the present invention.
Figure 38:
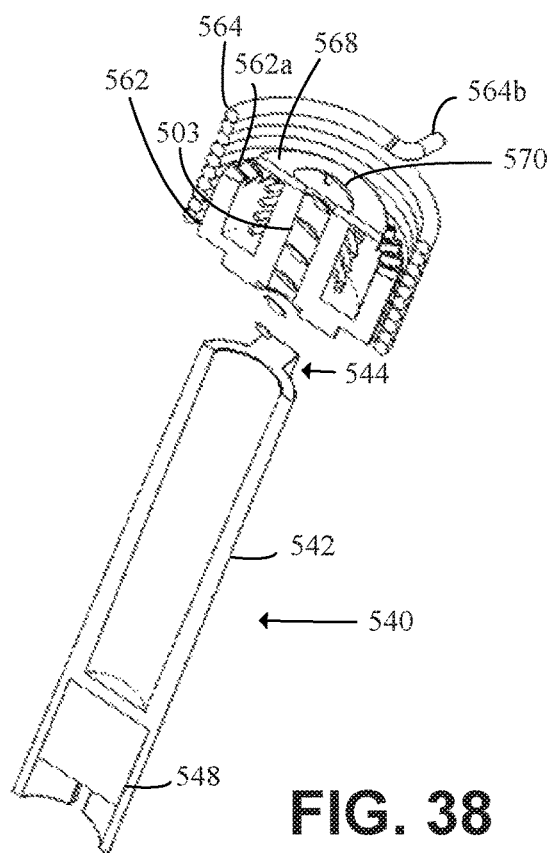
FIG. 38 illustrates a portion of a medial device in accordance with an embodiment of the present invention.
Figure 42:
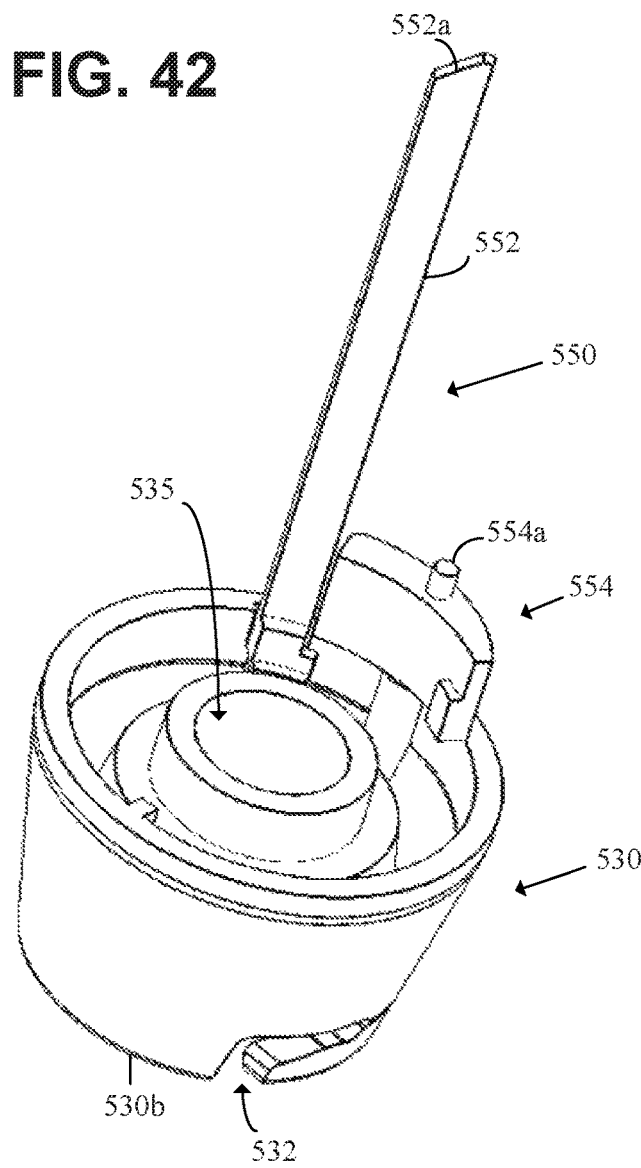
FIG. 42 illustrates a portion of a medial device in accordance with an embodiment of the present invention.
Figure 43:
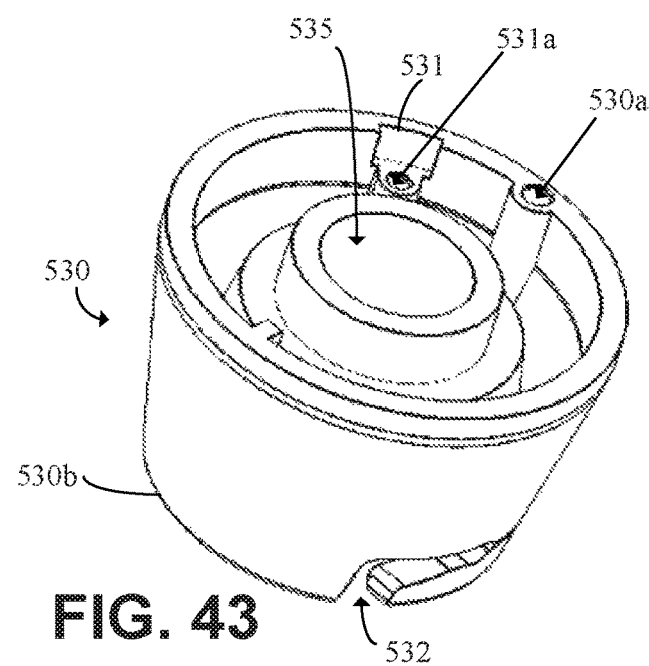
FIG. 43 illustrates a portion of a medial device in accordance with an embodiment of the present invention.

FIGS. 22 and 23 illustrate an actuation device 390 according to an embodiment of the present invention. FIG. 24 illustrates a process for using the actuation device 390. Although the actuation device 390 may be similar or used with the embodiments of FIGS. 17-21, it should be understood that the actuation device 390 may also include some or all of the same components and operate in a manner similar to that shown and described in the embodiments of FIGS. 1-16. In addition, some or all of the features shown in FIGS. 1-21 may be combined in various ways and included in the embodiments and process shown in FIGS. 22-24. Likewise, it should be understood that any of the features of the embodiments and process of FIGS. 22-24 may be combined or otherwise incorporated into any of the other embodiments and process of FIGS. 22-24 as well as any other embodiment herein discussed.

The actuation device 390 may be similar to the actuation device 290 (e.g., FIGS. 17-20). With reference to FIGS. 17-23, the actuation device 390 may include a housing 391 securable to the insertion housing 280. A suitable connection structure may be provided on the actuation device 390 and/or the insertion housing 280 to provide a manually releasable connection between those components. For example, the connection structure may be similar to the connection structure previously described for connecting the actuation device 290 to the insertion housing 280. In some embodiments, the connection structure may include, but is not limited to, a threaded extension on one or the other of the actuation device 390 and the insertion housing 280 and a corresponding threaded receptacle on the other of the insertion housing 280 and the actuation device 390 for receiving the threaded extension in threaded engagement.

For example, an end 372 of a distal portion 370 of the actuation device 390 may be adapted to be insertable into the insertion housing 280, for example, within the outer chamber 282. The distal portion 370 may have a threaded portion 376 for threaded engagement of a threaded portion 282a within the insertion housing 280. The end 372 may be insertable into the outer chamber 282 of the insertion housing 280, for example, until a surface 371 of the actuation device 390 abuts a lip portion 283 of the insertion housing 280 and/or the end 372 contacts a floor 284b of the insertion housing 280.

In other embodiments, other suitable connection structures may be employed. Such a connection structure may include, but is not limited to, flexible pawls or extensions on one or the other of the actuation device 390 and the insertion housing 280 and a corresponding aperture, stop surface, or the like on the other of the insertion housing 280 and the actuation device 390.

The housing 391 may contain an internal chamber 392 having a longitudinal dimension and a member 398 arranged within the housing 391. The member 398 may be moveable in the direction L at least between a first position and a second position. The housing 391 may include a drive mechanism for actuating the member 398. The drive mechanism may be a bias member 393, such as, but not limited to, a coil spring, or the like, arranged within the internal chamber 392 of the housing 391. The bias member 393 may be configured to impart a bias force on the member 398 when the member 398 is in the first position to urge the member 398 toward the second position.

In some embodiments, an activation structure, such as a trigger, button, or the like, may be provided to control the actuation device 390. In further embodiments, a first trigger 394 may be configured to arm or prepare the actuation device 390 for firing or otherwise moving the member 398 to move the insert structure 260. For example, the first trigger 394 may be manually pressed to retract the bias member 393 to the first position. As such, the first button 394 may be adapted to selectively arm the member 398 and/or the bias member 393 into the first position (i.e., the retracted position).

A second trigger 397 or the like may be configured to selectively release the member 398 and/or the bias member 393 to allow the member 398 to move in the direction L under the force of the bias member 393 to the second position. In other embodiments, the first trigger 394 may be configured to selectively release the member 398 and/or the bias member 393 to allow the member 398 to move in the direction L under the force of the bias member 393 to the second position upon being operated after the actuation device 390 has been armed. For example, pressing the first trigger 394 a first time may retract the member 398 to the first position, and pressing the first trigger 394 a second time may release or otherwise allow the member 398 to advance to the second position. Other examples of insertion structures are described in U.S. Pat. Pub. No. US 2007/0142776, entitled "Insertion Device for an Insertion Set and Method of Using the Same," which is herein incorporated by reference in its entirety.

In yet further embodiments, a first locking mechanism (not shown) may be provided such as, but not limited to, a manually moveable projection, lever, slider, or the like. The first locking mechanism may be connected to or extending through the housing 391 and engaging the member 398 (or other structure holding the member 398) in a releasable manner to selectively hold the member 398 in the retracted position, for example after the first trigger 394 has been operated, against the bias force of the bias member 393.

In some embodiments, the actuation device 390 may be configured to allow the member 398 to be moved from the second position at least toward the first position automatically or upon manipulation by the user, for example, to a third position or a neutral position (e.g., position of the member before being moved to the first position when the actuation device is armed). That is, after the member 398 has been moved to the second position (e.g., an extended position), the member 398 may be moved to a third position automatically or upon manipulation of the actuation device 390 by the user-patient. The third position may be any suitable position at which the needle 246 is sufficiently withdrawn, for example, from the skin of the patient, such as, but not limited to, the first position, a position between the first and second positions, or the like.

For example in some embodiments, the housing 391 may include a second chamber 395. The second chamber 395 may be concentrically arranged relative to the internal chamber 392, for example around the internal chamber 392. A drive mechanism may be arranged within the second chamber 395 of the housing 391 to move the member 398. The drive mechanism may be a second bias member 396, such as, but not limited to, a coil spring, or the like, arranged to impart a bias force on the member 398 when the member 398 is in the second position to urge the member 398 toward third position. Thus, in some embodiments, the member 398 can be moved to the first position (e.g., by pressing the first trigger 394), moved to the second position (e.g., by pressing the second trigger 397), and then automatically moved to a third position.

In some embodiments, an activation structure, such as a trigger (e.g., first trigger 394, second trigger 397, or a third or further trigger (not shown)), button or the like, may be provided to control movement of the member from the second position to the third position. Thus, in some embodiments, the member 398 can be moved to the first position (e.g., by pressing the first trigger 394), moved to the second position (e.g., by pressing the second trigger 397), and then further moved to a third position (e.g., by pressing the first trigger 394, the second trigger 397, or the like).

In yet further embodiments, a second locking mechanism (not shown) may be provided such as, but not limited to, a manually moveable projection, lever, slider, or the like. The second locking mechanism may be connected to or extending through the housing 391 and engaging the member 398 (or other structure holding the member 298) in a releasable manner to selectively hold the member 398 in the second position, for example after the second trigger 397 has been operated, against the bias force of the second bias member 396.

In various embodiments, the member 398 may be adapted to operatively engage the plunger head 288, for example, when the actuation device 390 is connected to the insertion housing 280. The member 398 or a portion thereof may be made of a sufficiently rigid material, but having a certain amount of flexibility. A protrusion, extension, arm, or the like may be provided on one or the other of the member 398 and the plunger 288 and a corresponding aperture, protrusion, extension, arm or the like on the other of the plunger 288 and the member 398 for engaging each other. For example, in particular embodiments, the member 398 may have one or more arms 399 for engaging a head portion 289 of the plunger head 288 upon the actuation device 390 being connected to the insertion housing 280.

Thus in some embodiments, in a case where the member 398 is operatively engaged with the plunger head 288 and the member 398 is actuated, the insert structure 260, which may include the plunger head 288, the needle 246, the collar 268, and the cannula 248, may be moved to the second position. Similarly as previously described, the member 398 can be further actuated to move the first part 262 of the insert structure 260, which may include the plunger head 288 and the needle 246, away from the first position (e.g., to (or toward) the first position and/or the third position). Thus, the second part of the insert structure 260, which may include the collar 268 and the cannula 248, may remain in the second position to allow fluid to flow from the reservoir though the fluid conduit 224 and the connection channel 269 to the cannula 248 into the user-patient as previously described.

In various embodiments, the actuation device 390 may be configured for improved handling of the actuation device 390 by the user-patient. For example, the actuation device 390 may include a handling portion 355, grips, textured surfaces, or the like that may aid in handling of the actuation device 390.

Additionally, the actuation device 390 may allow for lancing or piercing the skin of the user-patient, for example, to obtain a blood sample. A lancing portion 350 may be removably attachable to the actuation device 390. The lancing portion 350 may be attached to or within the distal portion 370 in a friction fit, snap fit, threaded engagement, or the like. The lancing portion 350 may be adapted to operatively engage the member 398 such that movement of the member 398 causes movement of the lancing portion 350.

In various embodiments, the lancing portion 350 may be adapted to be removably attachable from the actuation device 390. For instance, when the lancing portion 350 is not in use, for example, the actuation device 390 may be coupled with an insertion housing (e.g., 280 in FIGS. 17-20) for inserting a needle and a cannula into the skin of the user-patient as previously described. Moreover, when the actuation device 390 is not being used with the insertion housing, the lancing portion 350 may be attached to the actuation device 390 for piercing the skin of the user-patient. The lancing portion 350 may be made of a material of suitable strength and durability such as, but not limited to, plastic, metal, glass, or the like.

The lancing portion 350 may include a collar body 352 and a piercing member, such as a needle 354. The collar body 352 may be made of a material of suitable strength and durability such as, but not limited to, plastic, metal, glass, or the like. The needle 354 may be supported by the collar body 352 so that the needle 354 may move with the collar body 352. For example, the needle 354 may extend through the collar body 352 or be operatively connected to the collar body 352. As previously discussed, in a case where the lancing portion 350 is operatively engaged with the member 398 and the member 398 is actuated, the lancing portion 350 may be caused to move by the member 398. Accordingly, the needle 354 may be actuated to move and exit the actuation device 390 to "prick" or otherwise pierce the skin of the user-patient. In other embodiments, the piercing member (e.g., needle 354) may be connected to the member 398 such that movement of the member 398 causes movement of the piercing member.

In various embodiments, a penetration depth of the needle 354 into the skin of the user-patient may be adjustable. In some embodiments, the lancing portion 350 may be adapted to be arranged relative to the actuation device 390 to adjust the penetration depth of the needle 354. For example, by inserting the lancing portion 350 further into or further along the actuation device 390, the penetration depth of the needle 354 can be reduced accordingly. Conversely, the penetration depth of the needle 354 can be increased by arranging or otherwise extending the lancing portion 350 further from the actuation device 390. In some embodiments, the needle 354 may be adapted to be adjustable relative to the collar body 352 in a similar fashion to decrease or increase the penetration depth of the needle 354.

In some embodiments, the actuation device 390 may include an adjustment member (not shown) for selectively adjusting the penetration depth of the needle 354. The adjustment member may be an at least partially rotatable dial, a slide, a trigger, a button, or the like. The adjustment member may be operatively engaged with the member 398, the first bias member 393, the second bias member 396, the collar body 352 of the lancing portion 350, and/or the needle 354 so that the penetration depth of the needle 354 can be varied. For example, rotation of the adjustment member may cause the lancing portion 350, portion thereof, and/or operatively connected components to advance or retreat relative to the actuation device 390 to increase or decrease the penetration depth of the needle 354.

In some embodiments, the actuation device 390 may be adapted to engage with and disengage from a guard 330 or cover. The guard 330 may have a housing 332 having an interior chamber 334. The guard 330 may be made of a material of suitable strength and durability such as, but not limited to, plastic, metal, glass, or the like. A suitable connection structure, such as one of the connection structures previously described, may be provided on the actuation device 390 and/or the guard 330 to provide a manually releasable connection between those components. In some embodiments, the connection structure may include, but is not limited to, a threaded extension on one or the other of the actuation device 390 and the guard 330 and a corresponding threaded receptacle on the other of the guard 330 and the actuation device 390 for receiving the threaded extension in threaded engagement.

For example, the end 372 of the distal portion 370 of the actuation device 390 may be adapted to be insertable into the interior chamber 334 of the guard 330 through an opening 333 to attach the guard 330 to the actuation device 390. The distal portion 370 may have a threaded portion 376, which may or may not be similar to the threaded portion 276 for engaging the inserting housing 280, for threaded engagement of a threaded portion 336 within the guard 330. The end 372 may be insertable into the guard 330, for example, until a surface 371, which may or may not be similar to the surface 271, of the actuation device 390 contacts a portion, such as an outer surface 331a, of the guard 330 and/or the end 372 contacts a portion, such as an inner surface 331b, within guard 330. In other embodiments, a portion of the guard 330 may be configured to be insertable into the actuation device 390, for example through opening 374 through which the lancing portion 350 may be attached to the actuation device 390, to attach the guard 330 to the actuation device 390.

In other embodiments, other suitable connection structures may be employed for connecting the guard 330 with the actuation device 390. Such a connection structure may include, but is not limited to, flexible pawls or extensions on one or the other of the actuation device 390 and the guard 330 and a corresponding aperture, stop surface, or the like on the other of the other of the guard 330 and the actuation device 390.

An aperture 335 or the like may be provided on the housing 332 of the guard 330 and extending through to the interior chamber 334. The aperture 335 may be located on an end 332*a* opposite the opening 333. The aperture 335 may allow the needle 354 or a portion thereof to extend beyond the end 332*a* of the guard 330 to pierce the skin of the user-patient, for example, when the member 398 is actuated to move the lancing portion 350. In various embodiments, the guard 330 may be arrangeable to adjust the penetration depth of the needle 354. For example, by arranging the guard 330 (e.g., screwing on the guard 330) further into or further along the actuation device 390, the penetration depth of the needle 354 can be increased accordingly. Conversely, the penetration depth of the needle 354 can be decreased by arranging guard 330 further from the actuation device 390.

As previously discussed, in some embodiments, the actuation device 390 may be configured to retract the needle 354 automatically after the needle 354 pierces the skin of the user-patient. In such embodiments, the needle 354 may pierce or prick the skin of the user-patient and then return to a position (e.g., the third position) within the actuation device 390 and/or the guard 330. In other embodiments, the actuation device 390 may be configured such that the needle 354 can be manually retracted after piercing the skin of the user-patient, for example, by operating the second trigger 397, or the like.

FIG. 24 illustrates a flowchart for using an actuation device according to an embodiment of the present invention. With reference to FIGS. 22-24, in step S1202, the lancing portion 350 may be attached to the actuation device 390. In step S1204, the penetration depth of the needle 354 may be adjusted.

Next in step S1206, the guard 330 may be attached to the actuation device 390. In step S1208, the actuation device 390 may be placed adjacent a suitable injection site on the user-patient. In step S1210, the member 398 and the lancing portion 350 may be actuated to prick the user-patient at the injection site. In further embodiments, the lancing portion 350 may be removed from the actuation device 390, and the actuation device 390 may be used similar to the actuation device 290 and an infusion set, such as, but not limited to, the system 200 described with respect to FIGS. 17-21.

FIGS. 25-29 illustrate an insertion housing 480 according to an embodiment of the present invention. The insertion housing 480 may be similar to or employed as an embodiment of the insertion housing 280 (e.g., FIGS. 17-20), and for example, may be used with the inserting system 200 (e.g., FIGS. 17-20) and/or the like discussed in this disclosure. Although the insertion housing 480 may be similar or used with the embodiments of FIGS. 17-20, it should be understood that the insertion housing 480 may also include some or all of the same components and operate in a manner similar to that shown and described in the embodiments of FIGS. 1-16 and 30-43. In addition, some or all of the features shown in FIGS. 1-16 and 30-43 may be combined in various ways and included in the embodiments shown in FIGS. 25-29. Likewise, it should be understood that any of the features of the embodiments of FIGS. 25-29 may be combined or otherwise incorporated into any of the other embodiments of FIGS. 25-29 as well as any other embodiment herein discussed.

With reference to FIGS. 25-29, in some embodiments, the insertion housing 480 may be used with a first member (e.g., 202 in FIGS. 17-20) having a housing (e.g., 204 in FIGS. 17-20) on a base (e.g., 206 in FIGS. 17-20). The housing 204 may be formed integral with the base 206 or may be formed as a separate structure connected to the base 206 in a fixed relation to the base 206. The housing 204 and the base 206 each may be made of any suitably rigid material, including, but not limited to plastic, metal, ceramic, composite material, or the like.

The housing may include an injection site section (e.g., 205 in FIGS. 17-20) containing an injection site structure in which a hollow needle or cannula may be inserted into a user-patient for conveying fluidic media to or from the user-patient. In other embodiments, instead of or in addition to an injection site, the housing 204 may contain, be part of, or be operatively connected to any other suitable structure for conveying, containing, and/or processing fluidic media.

The first member 202 may be operatively connectable to a second member (not shown), which may include a housing (e.g., 108 in FIGS. 7-12), which in the illustrated embodiment may include a reservoir (e.g., 107 in FIGS. 7-12) for containing fluidic media. The second member may be held within or otherwise be covered by an outer housing (e.g., 109 in FIGS. 7-12) configured to attach to the base 206. The outer housing 109 may be configured to connect to the base 206 of the first member 202 by any suitable connection structure. In some embodiments, upon coupling the first member 202 and the second member, fluid flow communication may be provided between the second member and the injection site section 205 in the first member 202.

In particular embodiments, at least one of the outer housing 109 and the base 206 may include one or more flexible pawls, protrusions, indentations, or the like for engaging and/or receiving one or more corresponding pawls, protrusions, indentations, or the like on the other of the base 206 and the outer housing 109 to provide a suitable connection structure. Alternatively or in addition, the connection structure may include adhesive material or other suitable connectors.

The housing 204 may have or be connected to a receptacle structure (e.g. 110, 210 in FIGS. 7-12 and 17-20) having a chamber (e.g., 214 in FIGS. 17-20). In some embodiments, the receptacle structure 210 may be part of the housing adjacent a section of the housing containing the injection site section 205. In other embodiments, the receptacle structure 210 may include a further housing connected to the housing.

A fluid conduit (e.g., 224 in FIGS. 17-20), such as, but not limited to, a needle or the like may be supported within the chamber. The fluid conduit 224 may be supported by a supporting structure located within the receptacle structure 210. In some embodiments, the supporting structure may be a wall integral with the receptacle structure 210. In other embodiments, the supporting structure may be any suitable structure that is generally fixed relative to the receptacle structure 210 and is able to support the fluid conduit 224 in a generally fixed relation to the receptacle structure 210.

The fluid conduit 224 may be made of any suitably rigid material, including, but not limited to metal, plastic, ceramic, or the like, and may have a hollow channel extending in a lengthwise dimension of the fluid conduit 224. The hollow channel in the fluid conduit 224 may be open at a location (not shown) along the lengthwise dimension of the fluid conduit 224, such as, but not limited to, a first end of the fluid conduit 224. The hollow channel in the fluid conduit 224 may be open at another location (e.g., 224b in FIGS. 17-20) along the lengthwise dimension of the fluid conduit 224, such as, but not limited to, a second end of the fluid conduit 224 opposite the first end of the fluid conduit 224. One of the openings in the fluid conduit 224 may be provided with a septum (e.g., 226 in FIGS. 17-20) that may be pierceable by a needle (not shown), for example as previously described, when a reservoir is connected to the first member 202.

The injection site section 205 may include a channel (e.g., 240 in FIGS. 17-20) extending through the housing 204 and the base 206. The channel 240 may have an open end (e.g., 240a in FIGS. 17-20) on a bottom surface (e.g., relative to the orientation shown in FIG. 18) of the base. The channel 240 may have another open end (e.g., 240b in FIGS. 17-20) at an upper surface (e.g., relative to the orientation shown in FIG. 18) of the injection site section 205 of the housing 204. The channel 240 may include a channel section (e.g., 242 in FIGS. 17-20) having a larger radial dimension relative to a remaining portion of the channel 240 and may have a suitable shape and size to receive an insert structure, a needle, and/or a cannula, as will be described.

The insertion housing 480 may be made of a material of suitable strength and durability such as, but not limited to, plastic, metal, glass, or the like. The insertion housing 480 may be located adjacent the open end of the channel 240 and arranged to selectively extend a needle and/or cannula of an insert structure into the open end of the channel 240 and at least partially through the channel 240, as will be described.

The insertion housing 480 may be a separate device from the housing 204 and may be selectively engaged or connected to, for example in alignment with the channel 240, and disengaged or disconnected from the injection site section 205 and/or the first member 202 or portion thereof. In some embodiments, the insertion housing 480 may be recommended for disposal after a specified number of uses.

A suitable connection structure, such as that described throughout this disclosure, may be provided on the insertion housing 480, the injection site section 205, and/or the first member 202 or portion(s) thereof to provide a manually releasable connection between those components. For example, the connection structure may include, but is not limited to, a threaded extension on one or the other of the insertion housing 480 and the injection site section 205 and a corresponding threaded receptacle on the other of the injection site section 205 and the insertion housing 480 for receiving the threaded extension in threaded engagement. In other embodiments, other suitable connection structures may be employed. These may include, but are not limited to, friction-fitted sections, flexible pawls or extensions on one or the other of the insertion housing 480 and the injection site section 205 (or the first member 202, or portion thereof) and a corresponding aperture, stop surface, or the like on the other of the injection site section 205 (or the first member 202, or portion thereof) and the insertion housing 480.

In some embodiments, the insertion housing 480 may include one or more latches 470 configured to operatively engage with and disengage from the insertion site section 205 (or the first member 202), or the like. For instance, in some embodiments, the latch 470 may include an arm 472 with one or more protrusions 474 for engaging with and disengaging from an aperture (e.g., 205a in FIGS. 17-20), a retaining surface (e.g., 205b in FIGS. 17-20), and/or the like of the insertion site section 205 (or the first member), or the like. In some embodiments, the arm 472 may have a recess 475, for example defined by the one or more protrusions 474 or formed in the arm 472, for engaging a protrusion or the like provided on the injection site section 205 (or the first member 202). In other embodiments, the arm 472 may have one or more apertures (not shown) or the like for receiving one or more protrusions (not shown) or the like from the insertion site section 205 (or the first member 202), or the like.

The latch 470 may be made of any suitably rigid material, such as plastic, glass, metal, composite material, ceramic, and/or the like. In some embodiments, the latch 470 may be made of similar material as the insertion housing 480. In other embodiments, the latch 470 may be made of different material from the insertion housing 480.

In some embodiments, the latch 470 may be integral with the insertion housing 480. The latch 470 may be sufficiently flexible to operatively engage with and disengage from an engagement portion, for example as previously described, of the first member 202 as the latch 470 flexes toward and away from the first member.

In other embodiments, the latch 470 may be operatively connected with the insertion housing 480. For instance, the latch 470 may be adapted to pivot about a portion of the insertion housing 480 to allow the latch 470 to operatively engage with and disengage from the first member 202 as the latch 470 pivots toward and away from the engagement portion of the first member 202. For example, the latch 470 may include one or more apertures for receiving a protrusion 481a on the insertion housing 480 to allow the latch 470 to pivot about the protrusion 481a. As another example, the latch 470 may include one or more protrusions (not shown) pivotable in one or more apertures (not shown) provided in the insertion housing 480 to allow the latch 470 to pivot about the apertures in the insertion housing 480.

Throughout various embodiments in the disclosure, the engagement portion of the first member 202 may be, but is not limited to, an aperture, a ridge, an undersurface (or upper surface), a protrusion, a tab, an arm, a bias member, or any other suitable structure or mechanism arrangeable to allow the latch 470 to engage with and/or disengage from the first member 202.

In some embodiments, the insertion housing 480 may include a protrusion 481c for engaging an aperture (not shown) or the like in the first member 202 to connect the insertion housing 480 to the first member 202. In other embodiments, the insertion housing 480 may include an aperture (not shown) for receiving a protrusion (not shown) or the like in the first member 202 to connect the insertion housing 480 to the first member 202. In particular embodiments, once the insertion housing 480 is connected with the first member 202 in any suitable manner, for example (but not limited to) as described above, the latch 480 may be connected with the first member 202 to further secure the insertion housing 480 to the first member 202.

In further embodiments, an abutment 476, such a tab, finger, protrusion, or the like, may be provided on the arm 472 to substantially prevent the latch 470 from engaging the first member 202 after the latch 470 has been disengaged from the first member 202, for example, as discussed in the disclosure. Thus, once the latch 470 is disengaged from the first member 202, the abutment 476 may prevent the latch 470 from re-engaging the first member 202, for example, by preventing the latch 470 from sufficiently pivoting forward.

The insertion housing 480 may contain a main chamber 487 in alignment with the opening of the injection site section 205. The insertion housing 480 may have a longitudinal dimension. An insert structure 460 may be located within the insertion housing 480 and moveable along the longitudinal dimension along a line L. The insert structure 460 may be moveable at least between a first position and a second position. The insert structure 460 may include a first part 462 and a second part 464 operatively connected to the first part 462 so that the first part 462 and the second part 462 may move together along the line L. The insert structure 460 may be biased toward or otherwise held in the first position until sufficient force is applied to the insert structure 460 to move or otherwise actuate the insert structure 460 to the second position.

Various examples of suitable structures for insert structures are described in this disclosure, as well as in U.S. patent application Ser. No. 11/645,435, filed Dec. 26, 2006, entitled "Infusion Medium Delivery System, Device And Method With Needle Inserter And Needle Inserter Device And Method," which is assigned to the assignee of the present invention and is incorporated herein by reference in its entirety. Further examples of various insert structures are described in, but are not limited to, U.S. patent application Ser. No. 11/645,972, filed Dec. 26, 2006, "Infusion Medium Delivery System, Device And Method With Needle Inserter And Needle Inserter Device And Method"; U.S. patent application Ser. No. 11/646,052, filed Dec. 26, 2006, "Infusion Medium Delivery System, Device And Method With Needle Inserter And Needle Inserter Device And Method"; U.S. patent application Ser. No. 11/645,435, filed Dec. 26, 2006, "Infusion Medium Delivery System, Device And Method With Needle Inserter And Needle Inserter Device And Method"; U.S. patent application Ser. No. 11/646,000, filed Dec. 26, 2006, "Infusion Medium Delivery System, Device And Method With Needle Inserter And Needle Inserter Device And Method," all of which are herein incorporated by reference in its entirety. Other examples of suitable structures for insert structures are described herein.

The first part 462 of the insert structure 460 may include a plunger head 488 and a needle 446 supported by the plunger head 488. The second part 464 of the insert structure 460 may include a collar 468 and a cannula 448 supported by the collar 468. The first part 462 and the second part 464 may be configured to be removably attachable from each other, for example, in a friction fit engagement, snap fit engagement, or the like. For example, one of the plunger head 488 and the collar 468 may include protrusions or the like and the other of the plunger head 488 and the collar 468 may include apertures for receiving the protrusions. Accordingly, the first part 462 may be separable from the second part 464 upon application of a sufficiently strong separating force. In particular embodiments, the plunger head 488 may be connected to the collar 468.

The cannula 448 may extend at least partially through the collar 468. The cannula 448 may be fixed to the collar 468 to move with movement of the insert structure 460. The cannula 448 may have a hollow central channel 448c extending along a longitudinal length of the cannula 448 and open at one end 448a that may be adjacent a sharp end 446a of the needle 446 disposed within the cannula 448 as will be discussed. An end 448b of the cannula 448 opposite the open end 448a may have a head 449 having a larger radial dimension than a shaft portion 448d of the cannula 448.

In some embodiments, the head 449 may be separate from the cannula 448. In such embodiments, the head 449 may be in fluid communication with the cannula 448. For example, a portion of the head 449 may be aligned with the cannula 448 to allow fluid to flow therebetween. In other embodiments, the head 449 may be integral with the cannula 448.

A septum 466 may be supported or otherwise retained by the collar 468. The septum 466 may be a resealable member made of silicone, plastic, rubber, Teflon, or the like. The septum 466 may be arranged between the plunger head 488 and the collar 468. The septum 466 may be pierceable by the needle 446.

The needle 446 may be arranged to extend through at least a portion of the cannula 448. The needle 446 may be supported by, secured, and/or operatively connected to the plunger head 488 to move with movement of the insert structure 460. Thus, in some embodiments, the plunger head 488 and the needle 446, which may be both part of the first part 462 of the insert structure 460, and the collar 468 and the cannula 448, which may be both part of the second part 464 of the insert structure 460, may be moveable at least between the first position and the second position.

In the second position, the needle 446 and the cannula 448 may extend through the opening of the channel 240 and at least partially through the channel 240. As such, the sharp end 446a of the needle 446 and at least a portion of the length of the cannula 448 may extend out the opening of the channel 240, for example, into skin of a user-patient.

The collar 468 of the insert structure 460 may have a suitable shape and size to fit into the channel section 242 of the channel 240 when the insert structure 460 is moved to the second position, for example, by an actuation device, as will be discussed. In particular embodiments, the collar 468 may include one or more protrusions (not shown) and/or indentations that engage with one or more corresponding indentations, such as the aperture, and/or protrusions in the injection site section 205 to provide a friction fit, snap fit, or the like. Accordingly, the second part 464 may be retained within the injection site section 205 upon the insert structure 460 being moved to the second position.

In further embodiments, instead of or in addition to engaging protrusions and indentations, one or more other mechanical structures may be employed to provide a suitable retaining function for retaining the second part 464 in place within the injection site section 205 upon the insert structure 460 being moved to the second position, for example, by an actuation device. These mechanical structures may include, but are not limited to, a friction fit structure, snap fit structure, or the like.

In various embodiments, the latch 470 of the insertion housing 480 may be actuated to disengage the insertion housing 480 automatically from the first member 202 upon the insert structure 460 being moved to the second position. For example, the latch 470 may be adapted to flex or pivot away from the insertion housing 480 to disengage the first member 202 when the insert structure 460 is moved to the second position. In moving to the second position, a protrusion or the like on the insert structure 460 may push against the one or more protrusions 474 of the latch 470 engaged with the first member 202. This may displace the one or more protrusions 474 of the latch 470 and release the latch 470 from the first member 202. Accordingly, in such embodiments, the insertion housing 480 may be removed.

In some embodiments, removal of the insertion housing 480 may also remove the first part 462 (or portion thereof) that may include the needle 446 and the plunger 488, while leaving the second part 464 (or portion thereof) that may include the cannula 448 and the collar 468 engaged to the injection site section 205. In other embodiments, removal of the insertion housing 480 may also remove the first part 462

(or portion thereof), which may include the needle 446 and the plunger 488, and the second part 464 (or portion thereof), which may include the cannula 448 and the collar 468.

The collar 468 may have a connection channel 469 provided in fluid flow communication with an opening (not shown) in the cannula 448 in fluid flow communication with the hollow central channel 448c of the cannula 448. In some embodiments, the connection channel 469 may be in fluid flow communication with an opening in the head 449, which may be in fluid flow communication with the hollow central channel 448c of the cannula 448. Thus in various embodiments, the connection channel 469 may be in fluid flow communication with the hollow central channel 448c of the cannula 448.

The connection channel 469 may be provided along the collar 468 at a location at which the connection channel 469 may align with the fluid conduit 224 upon the insert structure 460 being moved to the second position. Thus in some embodiments, in a case where the first member 202 and the second member are brought together (e.g., FIG. 9) and the insert structure 460 is in the second position, a fluid flow path may be established between the reservoir in the second member and the cannula 448 via the fluid conduit and the connection channel 469.

In some embodiments, the insertion housing 480 may include an inner housing portion 484 concentrically arranged within an outer housing portion 481. The inner housing portion 484 may have an inner chamber 485 in alignment with the chamber 487 in which the insert structure 460 may be arranged for movement. A lip portion (not shown) or the like extending from the inner housing portion 484 may be for containing the insert structure 460 in the inner chamber 485. For example, the insert structure 460 may be in contact with or otherwise adjacent the lip portion when the insert structure 460 is in the first position.

The outer housing 481 may have an outer chamber 482 between the outer housing 481 and the inner housing portion 484. The outer chamber 482 may be for receiving at least a portion of an actuation device for actuating the plunger head 488 as will be described. In various embodiments, the inner housing portion 484 may be integral with the outer housing portion 481. In other embodiments, the inner housing portion 484 may be separate from the outer housing portion 481.

In some embodiments, the inner housing portion 484 may have one or fingers 484b that extend away from the inner housing portion 484 (in a direction facing an attached actuation device). One or more of the fingers 484b may include a ridge 484a for supporting at least a portion of the plunger head 488, for example one or more protrusions 488a or the like of the plunger head 488, prior to movement of the insert structure 460. The fingers 484b may be sufficiently rigid, yet flexible to allow the fingers 484b and the ridge 484a to support the insertion structure 460 and allow the fingers 484b to be flexed (e.g., toward the outer housing portion 481) or otherwise separated to allow the insertion structure 460 to move past the ridge 484a (e.g., the first position).

In particular embodiments, the fingers 484b and a corresponding actuation device (as will be described) for the insertion housing 480 may be configured such that the actuation device sufficiently flexes or otherwise separates the fingers 484b to allow movement of the insertion structure 460 beyond the ridge 484a. Thus, for example, in a case where the actuation device is properly connected and the actuation device is actuated, the actuation device may cause the insertion structure 460 to move from the first position to the second position.

Thus various embodiments may allow for inhibiting a false firing of the insertion structure 460 unless the actuation device is properly connected with the insertion housing 480. In other words, in these embodiments, even if a force is applied to the insertion structure 460, for example, from an actuation device, the insertion structure 460 will not be advanced unless the fingers 484b are flexed or otherwise separated (e.g., by properly attaching the actuation device) to provide sufficient clearance to allow the insertion structure to advance. In further embodiments, the ridge 484a may have a sloped surface 484c to allow the insertion structure 460 to move past the ridge 484a, for example after the cannula 448 is inserted into the user, to return the insertion structure 460 to a position in which the insertion structure 460 is supported by the ridge 484a.

As previously discussed, in various embodiments, the insert structure 460 (i.e., the plunger head 488, the needle 446, the collar 468, and the cannula 448) may be actuated to move to the second position by (but not limited to) an actuation device 290 or 390 (e.g., FIGS. 17-24) or other actuation device discussed in this disclosure. FIGS. 30-43 illustrate an actuation device 500 according to an embodiment of the present invention. The actuation device 500 may be similar to or employed as an embodiment of the actuation device 290 or 390 (e.g., FIGS. 17-24), and for example, may be used with (but not limited to) the inserting system 200 (e.g., FIGS. 17-20) and/or the like discussed in this disclosure.

Although the actuation device 500 may be similar or used with the embodiments of FIGS. 17-24, it should be understood that the actuation device 500 may also include some or all of the same components and operate in a manner similar to that shown and described in the embodiments of FIGS. 1-16 and 25-29. In addition, some or all of the features shown in FIGS. 1-16 and 25-29 may be combined in various ways and included in the embodiment shown in FIGS. 30-43. Likewise, it should be understood that any of the features of the embodiments of FIGS. 30-43 may be combined or otherwise incorporated into any of the other embodiments of FIGS. 30-43 as well as any other embodiment herein discussed.

With reference to FIGS. 25-43, the actuation device 500 may include a housing 510, a drive mechanism 560, and a drive member 540. The housing 510 may be securable to the insertion housing 480 or any other insertion housing, for example (but not limited to) as described in this disclosure. The housing 510 may be made of any suitably rigid material, including, but not limited to plastic, metal, ceramic, glass, composite material, and/or the like. A suitable connection structure may be provided on the actuation device 500 and/or the insertion housing 480, for example as described in this disclosure, to provide a manually releasable connection between those components. In some embodiments, the connection structure may include, but is not limited to, a threaded extension on one or the other of the actuation device 500 and the insertion housing 480 and a corresponding threaded receptacle on the other of the insertion housing 480 and the actuation device 500 for receiving the threaded extension in threaded engagement.

In some embodiments, a distal portion 530 of the actuation device 500 may be adapted to engage the insertion housing 480. The distal portion 530 may have an inner chamber 536 for receiving at least a portion of the insertion housing 480. The distal portion 530 may be integral with the housing 510. In other embodiments, the distal portion 530 may be separate and connected with the connected with the housing 510. The distal portion 530 may be made of any suitably rigid material, including, but not limited to plastic, metal, ceramic, glass, composite material, and/or the like.

The distal portion 530 may have least one slot 532 or the like for engaging at least one tab 481e or the like of the insertion housing 480, which may be located on an outer periphery of the outer housing portion 481. For example, the slot 532 may receive the tab 481e as the actuation device 500 is connected with the insertion housing 480.

In further embodiments, the distal portion 530 and/or the insertion housing 580 may be configured so that an additional rotation of the actuation device 500 relative to the insertion housing 480 may lock the tab 481e in the slot 532. In yet further embodiments, the additional rotation of the actuation device 500 relative to the insertion housing 480 may cause the legs 484b to separate to allow the insertion structure 460 to be moved by the actuation device 500 as described. For example, the distal portion 530 may have an edge 537, surface, tab, or the like within the chamber 536 for forcing the legs 484b apart, for example, in a case where the actuation device 500 receives a portion of the insertion housing 480 and the actuation device 500 is rotated relative to the insertion housing 480. In other embodiments, the insertion housing 480 may include at least one slot (not shown) for receiving at least one tab (not shown) of the actuation device 500. In other embodiments, the distal portion 530 of the actuation device 500 may be adapted to be insertable into the insertion housing 480, for example, within the outer chamber 482.

Thus in various embodiments, the insertion housing 480 and/or the actuation device 500 may be configured to lock the actuation device 500 to the insertion housing 480, for example, in a case where the tab 481e is received in the slot 532 and the actuation device 500 is rotated relative to the insertion housing 480. The actuation device 500 may be unlocked from the insertion housing 480, for example, by rotating the actuation device 500 relative to the insertion housing 480 in an opposite direction from the direction for locking the two components.

In other embodiments, other suitable connection structures may be employed. Such a connection structure may include, but is not limited to, friction-fitted sections of the insertion housing 480 and the actuation device 500, flexible pawls or extensions on one or the other of the actuation device 500 and the insertion housing 480 and a corresponding aperture, stop surface, or the like on the other of the insertion housing 480 and the actuation device 500.

The housing 510 may include an outer body 512 and an inner body 514 concentrically arranged within the outer body 512. The outer body 512 and the inner body 514 may define an outer chamber 513. The inner body 514 may have an inner chamber 515. The inner chamber 515 may be in communication with the inner chamber 536 of the distal portion 530 of the actuation device 500. A cam assembly 580 may be supported in the outer chamber 513 between the outer body 512 and the inner body 514.

The drive member 540 may be supported in the inner chamber 515 of the inner body 514 and moveable along a longitudinal dimension of the actuation device 500 through at least a portion of the inner chamber 515 and the inner chamber 536 at least between a first position and a second position. The inner body 514 may have a groove 514a extending at least a portion of the inner body 514 to allow movement of a portion (e.g., protrusion 544) of the drive member 540.

The drive member 540 may be made of any suitably rigid material, including, but not limited to plastic, metal, ceramic, glass, composite material, and/or the like. The drive member 540 may be moveable along a line M at least between a first position and a second position. The line M traveled by the drive member 540 and line L traveled by the insert structure 460 may share a common axis, for example, in a case where the actuation device 500 and the insertion housing 480 are connected properly.

In various embodiments, the drive member 540 may be adapted to operatively engage the plunger head 488, for example, when the actuation device 500 is connected to the insertion housing 480, in any suitable manner discussed in this disclosure. In some embodiments, the drive member 540 may include a magnet 548 or the like for interacting with a magnet or magnetically attractive element 490 (e.g., metal, ferrous conduit, and/or the like) operatively connected with the plunger head 488 to allow the drive member 540 to operatively engage the insert structure 460.

In other embodiments, the drive member 540 may include a magnetically attractive element (not shown) (e.g., metal, ferrous conduit, and/or the like) for interacting with a magnet (not shown) operatively connected with the plunger head 488 to allow the drive member 540 to operatively engage the insert structure 460. Such embodiments including a magnet in at least one of the insertion housing 480 and the actuation device 500 may allow for operatively engaging the actuation device 500 and the insertion housing 480. In addition, such embodiments may allow for improved alignment of the actuation device 500 with the insertion housing 480 when the two components are being connected.

Thus in various embodiments, in a case where the drive member 540 is operatively engaged with the plunger head 488 and the drive member 540 is actuated, the insert structure 460, which may include the plunger head 488, the needle 446, the collar 468, and the cannula 448, may be moved to the second position. Thus movement of the drive member 540 along the line M from the first position to the second position may cause the insert structure 460 to move from the first position to the second position.

Similarly as previously described, the drive member 540 can be further actuated to move the first part 462 of the insert structure 460, which may include the plunger head 488 and the needle 446, away from the second position (e.g., to (or toward) the first position and/or a third position). Thus, the second part 464 of the insert structure 460, which may include the collar 468 and the cannula 448, may remain in the second position to allow fluid to flow from the reservoir though the fluid conduit and the connection channel 469 to the cannula 448 into the user-patient as previously described. As such, the needle 446 may be removed from the user-patient while retaining the cannula 448 in the user-patient. In particular embodiments that include a magnet (e.g., magnet 548) in at least one of the insertion housing 480 and the actuation device 500, an attractive force between the magnet and an attractive element (e.g., another magnet, metal, ferrous conduit, and/or the like) may allow for retraction of the needle 446 from the user-patient in a case where the drive member 540 is moved away from the insertion housing 480 (e.g., toward the first position).

The drive mechanism 560 may be for actuating the drive member 540. The drive mechanism 560, which may include or may be a bias member 564, such as, but not limited to, a coil spring, or the like, arranged within the actuation device 500. The bias member 564 may be configured to impart a force on the drive member 540 to urge the drive member 540 at least from the first position toward the second position.

In various some embodiments, the drive mechanism 560 may be employed to move the drive member 540 at least between the first position and the second position. The drive mechanism 560 may be any suitable mechanism, for example (but not limited to) as described in this disclosure, for providing a driving force to the drive member 540 to move the drive member 540 at least between the first position and the second position.

In various embodiments, the drive mechanism may include an activation mechanism, such as the knob 520, trigger, button, or the like, for controlling the actuation device 500. For instance, the knob 520 may be configured to arm, prime, or otherwise prepare the actuation device 500 for moving the drive member 540 to move the insert structure 460. As such, the knob 520 may be for adjusting or otherwise setting the driving force (e.g., priming) for moving the drive member 540 at least between the first position and the second position.

In particular embodiments, the knob 520 may be operatively engaged with the cam assembly 580, as will be described, so that movement (e.g., rotation) of the knob 520 causes movement (e.g., rotation) of the cam assembly 580. In such embodiments, the knob 520 may be for priming the actuation device 500 for firing.

In some embodiments, the bias member 564 may be a torsion spring 564 or the like. The drive mechanism 560 may include a retainer member 562. The knob 520 may be operatively engageable with the retainer member 562. For example, the knob 520 may include teeth (not shown) or the like for mating with teeth 562a of the retainer member 562. As such, the knob 520 and the retainer member 562 may engage each other so that the retainer member 562 can be moved with movement of the knob 520, for example, in a clockwise or counter-clockwise direction. In some embodiments, the torsion spring 564 may be provided around the retainer member 562 (or any other suitable location).

In various embodiments, the torsion spring 564 and the knob 520 may be operatively connected with the cam assembly 580 such that movement of the knob 520 (in one or more directions) winds or otherwise primes the torsion spring 564. For instance, the torsion spring 564 may have an end 564a for fitting into an aperture or the like (not shown) in the cam assembly 580 and the knob 520 may be operatively engaged with the cam assembly 580, for example as described in this disclosure. As such, rotation of the cam assembly 580, for example by winding the knob 520, may wind the torsion spring 564 to prime the torsion spring 564. Thus in various embodiments, the knob 520 may be configured to selectively arm the actuation device 500.

In various embodiments, the torsion spring 564 may be operatively connected with the cam assembly 580 to allow the torsion spring 564 to apply a force on the cam assembly 580, for example, in a case where the torsion spring 564 has been primed (e.g., by winding the knob 520 sufficiently in a first direction) and energy stored by the torsion spring 564 (from priming the torsion spring 564) is released (or the torsion spring 564 is otherwise allowed to move the cam assembly 580 in a second direction, opposite the first direction), for example, by actuating a trigger or the like as will be described. Thus, the actuation device 590 (e.g., the drive member 540) may be fired by priming the torsion spring 564, and releasing the energy stored by the torsion spring 564 to apply a force on the cam assembly 580 to cause the cam assembly 580 to drive or otherwise move the drive member 540 at least between the first position and the second position.

In some embodiments, a bias member, such as a spring 566, or the like may be operatively engaged with the drive mechanism 560 to provide a bias force to the drive mechanism 560, for example, to prevent the knob 520 from rotating in a direction opposite (e.g., the second direction) a direction (e.g., the first direction) for priming the drive mechanism 560. In some embodiments, the knob 520 and/or the retainer member 562 may be configured to act as a ratchet or the like. Such embodiments may allow the user-patient to apply multiple partial rotations to the knob 520 to arm the actuation device 500 as opposed to having to rotate the knob completely in a single attempt to arm the actuation device 500. For example, the teeth of the knob 520 may engage with the teeth 562a of the retaining member 562 as the knob is rotated 520 to allow continued movement of the knob 520 in one direction (e.g., the first direction) while preventing the knob from 520 moving in the opposite direction (e.g., the second direction).

The knob 520 and/or the retainer 562 may be secured or otherwise operatively connected to the housing 510 in any suitable manner including, but not limited to, screws, bolts, fasteners, and/or the like. In particular embodiments, a self-tapping screw 570 (or the like) may be employed in a bore 563 of the retainer member to fasten the knob 520 and/or the retainer 562 to the housing 510. In further embodiments, a washer 568 or the like may be provided with the self-tapping screw (or other fastener).

The cam assembly 580 may comprise a drum cam 582 and a drum cam top 590. Each of the drum cam 582 and the drum cam top 590 may be made of any suitably rigid material, including, but not limited to plastic, metal, ceramic, glass, composite material, and/or the like. The drum cam 582 may have an interior 585 in which the drum cam top 590 may be supported. For example, the drum cam 582 may have a ridge 582a upon which at least a portion of the drum cam top 590 may sit. The drum cam 582 may include one or more tabs 582b that fit into corresponding apertures 590a in the drum cam top 590. The tabs 582b may prevent the drum cam top 590 from rotating (relative to the drum cam 582) in the interior 585 of the drum cam 582. Thus the drum cam top 590 may move (e.g., rotate) with movement (e.g., rotation) of the drum cam 582, for example, relative to the housing 510 and the drive member 540. In other embodiments, the drum cam 582 may include apertures (not shown) for receiving corresponding tabs (not shown) of the drum cam top 590.

The drum cam 582 may have a first interior surface 587 and a second interior surface 586 that is raised relative to the first interior surface 587. A sloped surface 586a may define a perimeter of the second interior surface 586. The second interior surface 586 may be relatively flush with an interior surface 596 of the drum cam top 590 in a case where the drum cam top 590 is supported in the interior 585 of drum cam 582. A sloped surface 596a may define a perimeter of the interior surface 596 of the drum cam top 590. The interior surface 596 of the drum cam top 590 and a sloped surface 596a may define an interior 595.

The sloped surface 596a of the drum cam top 590 and the sloped surface 586a of the drum cam 582 may define a track 588, groove, or the like between the two components. The drive member 540 may have a protrusion 544 or the like arranged for movement in the track 588. The protrusion 544 may be guided or otherwise moved by the cam assembly 580 along the track 588 to move the drive member 540 at least between the first position and the second position. For instance, the sloped surface 596a of the drum cam top 590 and the sloped surface 586a of the drum cam 582 may provide a circular track that spirals along the cam assembly 580 to allow the cam assembly 580 to rotate relative to the drive member 540. As such, rotation of the cam assembly 580 may guide the protrusion 544 along the track 588 to cause movement of the drive member 540 at least between the first position and the second position.

Thus in some embodiments, a cam assembly with a track along which a protrusion (or other portion) of a drive member is guided may be assembled using two separate components. Such embodiments may allow for cheaper and easier manufacturing (e.g., molding) processes. In other embodiments, the cam assembly 580 may be formed as one component with the track 588 formed therein. In yet other embodiments, the cam assembly may be assembled using any number of suitable components.

As mentioned, in some embodiments, the protrusion 544 of the drive member 540 may be arranged in the track 588 of the cam assembly 580. In such embodiments, when the actuation device 500 is fired, for example when the torsion spring 564 is released, the cam assembly 580 may rotate (e.g., in the second direction) relative to the drive member 540. As a result, a portion of the cam assembly (e.g., the sloped surface 596a of the drum cam top 590) may push or otherwise guide the protrusion 544 of the drive member 540 along the track 588. Thus, as the cam assembly 580 rotates, the drive member 540, via the cam assembly 580 pushing on the protrusion 544, may be moved between the first position and the second position.

In further embodiments, when the actuation device 500 is primed, for example when the knob 520 is wound, the cam assembly 580 may be rotated (e.g., in the first direction) relative to the drive member 540. As a result, a portion of the cam assembly (e.g., the sloped surface of the drum cam 582) may push or otherwise guide the protrusion 544 of the drive member 540 along the track 588. Thus, as the cam assembly 580 rotates, the drive member 540, via the cam assembly 580 pushing on the protrusion 544, may be moved between the second position and the first position.

In some embodiments, the cam assembly 580 may be configured to compensate or otherwise provide a tolerance for the protrusion 544 of the drive member 540 (relative to the cam assembly 580) as the protrusion 544 is guided along the track 588 by the cam assembly 580 to move the drive member 540 between the first position and the second position.

In particular embodiments, the cam assembly 580 may include a cap 592 and a bias member, such as a spring 594 or the like. The cap 592 may be supported on the drum cam 582. The drum cam top 590 may be supported within the drum cam 582 such that the drum cam top 590 may slide or otherwise move within the interior 585 of the drum cam 582, for example, toward and away from the cap 592 (e.g., along the line M). The spring 594 may be arranged between the drum cam top 590 and the cap 592 to provide a bias force on the drum cam top 590. For instance, the spring 594 may provide a bias force in a direction away from the cap 592, for example, when the actuation device 500 is fired so that the cam assembly 580 is rotated (e.g., in the second direction) causing the drum cam top 590 to push or otherwise guide the protrusion 544 to move the drive member 540 from the first position to the second position.

As such, the spring 594 may compensate for any shifting or other variation between the drum cam top 590 and the drum cam 582 caused by the cam top 590 guiding the protrusion 544 toward the bottom of the track 588 (e.g., position B in FIG. 35). For instance, the spring 594 may cause continued movement of the protrusion 544 until reaching the bottom of the track 588. Such embodiments may allow for compensating any variation in distance between, for example, the sloped surface 596 of the drum cam top 590 and the sloped surface 586a of the drum cam 582. Thus, any variation can be compensated before the protrusion 544 guided up the track 588 (e.g., toward position A in FIG. 35), for example to prime the actuation device 500 again (or for the first time). This may ensure that the drive member 540 and/or the insert structure 560 has traveled an expected distance, for example, a distance required to sufficiently insert the cannula 448 into the user-patient.

In addition, in various embodiments, the spring 594 may provide a bias force in a direction away from the cap 592, for example, when the actuation device 500 is primed so that the cam assembly 580 is rotated (e.g., in the first direction) causing the drum cam 582 to push or otherwise guide the protrusion 544 to move the drive member 540 from the second position to the first position (or other position). As such, the spring 594 may compensate for any shifting or other variation between the drum cam top 590 and the drum cam 582 caused by the drum cam 582 guiding the protrusion 544 toward the top of the track 588 (e.g., position A in FIG. 35). For instance, the spring 594 may cause continued movement of the protrusion 544 until reaching the top of the track 588. Such embodiments may allow for compensating any variation in distance between, for example, the sloped surface 596 of the drum cam top 590 and the sloped surface 586a of the drum cam 582. Thus, any variation can be compensated before the protrusion 544 guided down the track 588 (e.g., toward position B in FIG. 35), for example to fire the actuation device 500 again (or for the first time). This may ensure that the drive member 540 and/or the insert structure 560 has traveled an expected distance, for example, a distance required to sufficiently prime the actuation device 500 or component thereof.

In particular embodiments, the drum cam 582 and the cap 592 may be keyed to fit with each other. For instance, the drum cam 582 may have a tab 582b, protrusion or the like that fits into a recess 592b in the cap 592. In other embodiments, the drum cam 582 may have a recess (not shown) for receiving a tab (not shown), protrusion, or the like of the cap 592. In other embodiments, the cap 592 may be fit with the cam assembly 580 in any suitable manner such as (but not limited to) a friction fitting, welding, adhesive fitting, and/or the like. In some embodiments, the cap 592 may be a separate component from the drum cam 582. In other embodiments, the cap 592 may be integral with the drum cam 582. The cap 592 may be made of any suitably rigid material, including, but not limited to plastic, metal, ceramic, glass, composite material, and/or the like.

A trigger 554 or the like may be configured to selectively fire or otherwise actuate the actuation device 500, for example after the knob 520 has sufficiently primed the actuation device 500. For instance, the trigger 554 may be operatively connected to the bias member 564 to allow a force of the bias member to drive the drive member 540, for example by rotating the cam assembly 580, to the second position upon activation of the trigger 554.

In some embodiments, the trigger 554 may be configured to lock or otherwise prevent movement of at least one of the drive member 540, the cam assembly 580, and the bias member 564 in a particular direction or orientation until the trigger 554 is released or otherwise activated. For example, the trigger 554 may include a catch 555 for engaging with and disengaging from a portion of the drum cam 582, such as an abutment 583a of the drum cam 582. As such, rotation of the drum cam 582, for example in the second direction, may be substantially prevented in a case where, for example, the actuation device 500 is armed (e.g., by sufficiently winding the knob 520) and the abutment 583a of the drum cam 582 is engaged by the catch 555.

The trigger 554 may be mounted in the housing 510 and/or the distal portion 530. For example, the trigger 554 may have one or more of a first protrusion 554a and a second protrusion 554b for fitting into one or more of an aperture 510a in the housing 510 and an aperture 530a in the distal portion 530, respectively. Accordingly, the trigger 554 may be pivotable about the first protrusion 554a and the second protrusion 554b. For instance, the trigger 554 may be pressed (or otherwise activated) to pivot the trigger 554 to provide sufficient clearance between the catch 555 and the abutment 583a of the drum cam 582 to disengage the catch 555 from the abutment 583a. In other embodiments, the trigger 554 may have one or more of a first aperture (not shown) and a second aperture (not shown) for receiving one or more of a protrusion (not shown) of the housing 510 and/or a protrusion (not shown) of the distal portion 530, respectively In a case where the actuation device 500 is not primed (or in a case where the actuation device 500 has been fired), the catch 555 may rest against an abutment 583b of the drum cam 582. As the actuation device 500 is armed, for example, by winding the knob 520, the drum cam 582 may be rotated (e.g., in the first direction) relative to the housing 510 and the trigger 554 to allow the catch 555 to travel relative to the drum cam 582 along a groove 583 having a first end defined by the abutment 583b and a second end defined by the abutment 583a. The catch 555 may be allowed to travel in the same direction relative to the drum cam 582 until the catch 555 engages the abutment 583a on the other end of the groove 583, which may indicate that the actuation device 500 has been sufficiently armed. As described, as the cam assembly 580 is rotated (e.g., in the first direction), a portion of the cam assembly 580 (e.g., the sloped surface 586a of the drum cam 582) pushes or otherwise guides the protrusion 544 along the track 588. Thus, as the cam assembly 580 rotates, the drive member 540, via the cam assembly 580 pushing on the protrusion 544, may be moved between the second position and the first position to prime the actuation device 500.

In some embodiments, in a case where the protrusion 544 is guided along the track 588 to move the drive member 540 between the second position and the first position, the protrusion 544 may be guided in a direction (e.g., the first direction) opposite a direction (e.g., the second direction) in which the protrusion 544 travels along the track 588 as the drive member 540 is moved between the first position and the second position. In other embodiments, in a case where the protrusion 544 is guided along the track 588 to move the drive member 540 between the second position and the first position, the protrusion 544 may travel in a same direction (e.g., continued relative movement along the track 588) in which the protrusion 544 is guided along the track 588 as the drive member 540 is moved between the first position and the second position. In such embodiments, for example, the track 588 may be a circular track within the cam assembly 580. In further embodiments, the circular track 588 may be "V"-shaped (e.g., FIGS. 32 and 40) or otherwise have a "V"-shaped cross-section.

In some embodiments, a safety mechanism 550 may be provided for preventing the trigger 554 from being releasable or otherwise activated unless the actuation device 500 is sufficiently armed (e.g., by winding the knob 520 sufficiently). For example, the safety mechanism 550 may include a bar 552 supported within the housing 510 and adjacent the drum cam 582. A first end of the bar 552 located near the drum cap 592 may have an angled surface 552a and a second end, opposite the first end, may include a shelf 552b. The bar 552 may be arranged for movement between a first position and a second position as the drum cam 582 is rotated. In a case where the bar 552 is in the first position, the shelf 552b may obstruct or otherwise prevent the trigger 554 from being pressed to release the catch 555 to allow the drum cam 582 to rotate, thus firing the actuation device 500. In a case where the bar 552 is in the second position, the trigger 554 may be free of the shelf 552b, thus allowing the trigger 552 to be activated to allow the drum cam 582 to rotate to fire the actuation device 500.

A bias member, such as a spring 556 or the like, may be arranged in the actuation device 500, for example (but not limited to) in an aperture 531a in the distal portion 530, to provide a bias force on the bar 552 toward the first position (i.e., a position in which the trigger 554 cannot be pressed or otherwise activated because of obstruction by the shelf 552b of the bar 552).

The bar 552 may be operatively engaged with the knob 520 so that rotation of the knob 520 may cause movement of the bar 552 at least between the first position and the second position. For instance, the knob 520 may include a surface 523, edge, protrusion (or the like) for engaging a protrusion 592c (or the like) of the cap 592 so that rotation of the knob 520 (e.g., in the first direction) to prime the actuation device 500 may cause the cap 592 and the connected drum cam 582 to rotate as previously described. The surface 523 of the knob 520 may continue to move the protrusion 592c to rotate the cap 592 and the connected drum cam 582 to allow the surface 523 of the cap 592 to move along the angled surface 552a of the bar 552. Continued movement of the surface 523 of the cap 592 over the bar 552 may cause the bar 552 to move to the second position to free the trigger 554 from the shelf 552b of the bar 552. Accordingly, the trigger 554 may be free to be pressed or otherwise activated to actuate the actuation device 500.

In other embodiments, the knob 520 may be configured to selectively release the drive member 540 and/or the bias member 564 to allow the drive member 540 to move along the line M at least between the first position and the second position under the force of the bias member 564 to the second position upon being operated after the actuation device 500 is armed. For example, operating the knob 520 a first time may retract the drive member 540 to the first position and/or arm the bias member 564, and further operating the knob 520 a second time may release or otherwise allow the drive member 540 to advance to the second position. Other examples of insertion structures are described in, but are not limited to, U.S. Pat. Pub. No. US 2007/0142776, entitled "Insertion Device for an Insertion Set and Method of Using the Same," which is herein incorporated by reference in its entirety.

In various embodiments, the actuation device 500 may be configured for improved handling of the actuation device 500 by the user-patient. For example, the actuation device 500 may include a handling portion 528, grips, textured surfaces, or the like that may aid in handling of the actuation device 500. In some embodiments, the handling portion 528 may be arranged on the knob 520, the housing 510, and/or any other location on the actuation device 500 on which improved handling may be desired.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. An actuation device, comprising:
a housing having a distal end portion;
a lancing device configured to be held by and moveable relative to the distal end portion of the housing, the lancing device having a collar body carrying a piercing member;
a drive member supported by the housing and moveable in a first direction, the drive member comprising one or more arms and arranged to operatively engage the lancing device when the lancing device is held by the distal end portion of the housing such that the lancing device collar body at least partially surrounds the one or more arms, to move the lancing device in the first direction from a retracted position to an extended position upon movement of the drive member in the first direction, the retracted position of the lancing device relative to the distal end portion of the housing being adjustable;
a drive mechanism supported by the housing to impart a bias force on the drive member to urge the drive member in the first direction;
wherein the piercing member of the lancing device is arranged to extend from the distal end portion of the housing by a first distance when the lancing device is moved to the extended position, the first distance being adjustable by adjusting the retracted position of the lancing device relative to the distal end portion of the housing, and
wherein the lancing device is configured to be electively detached from the housing,
wherein the housing includes a connection mechanism for selectively connecting the distal end portion of the housing to an insertion device having a plunger head supporting a needle and cannula when the lancing device is detached from the housing, and wherein when the housing is connected to the insertion device housing, the one or more arms of the drive member are configured to engage the plunger head.

2. The actuation device of claim 1, wherein the drive member is arranged to selectively engage and move the moveable needle of the insertion device when the distal end of the housing is connected to the insertion device housing.

3. The actuation device of claim 1, further comprising a cover configured to be selectively attached to the connection mechanism on the housing when the lancing device is held by the distal end portion of the housing.

4. The actuation device of claim 3, wherein the connection mechanism comprises a threaded section of the distal end portion of the housing configured for engaging a threaded portion of the cover.

5. The actuation device of claim 4, wherein the threaded section of the distal end portion of the housing is configured for threaded engagement with a threaded portion of the insertion device housing when the lancing device is detached from the housing.

6. The actuation device of claim 3, wherein the cover includes an aperture through which a portion of the piercing member extends, when the lancing device is held by the distal end portion of the housing and is in the extended position.

7. The actuation device of claim 3, wherein the cover includes an aperture through which a length portion of the piercing member extends, when the lancing device is held by the distal end portion of the housing and is in the extended position, wherein the length portion of the piercing member that extends through the aperture is adjustable by adjusting the position of the cover relative to the distal end portion of the housing.

8. The actuation device of claim 7, wherein the connection mechanism comprises a threaded section of the distal end portion of the housing configured for threaded engagement with a threaded portion of the cover and adjusting the position of the cover relative to the distal end portion of the housing by adjusting the threaded engagement.

9. The actuation device of claim 1, wherein the piercing member comprises a needle.

10. An actuation device, comprising:
a housing having a distal end portion;
a lancing device configured to be held by and moveable relative to the distal end portion of the housing, the lancing device having a collar body carrying a piercing member,
the lancing device being configured to be selectively detached from the housing,
a connection mechanism for selectively connecting the distal end portion of the housing to an insertion device having a moveable needle and cannula when the lancing device is detached from the housing;
a drive member supported by the housing and moveable in a first direction, the drive member having one or more arms; and
a drive mechanism supported by the housing to impart a bias force on the drive member to urge the drive member in the first direction;
wherein the drive member is arranged to operatively engage the lancing device when the lancing device is held by the distal end portion of the housing such that the collar body of the lancing member at least partially surrounds the one or more arms of the drive member, to move the lancing device in the first direction from a retracted position to an extended position upon movement of the drive member in the first direction; and
wherein the drive member is arranged to operatively engage and move the moveable needle of the insertion device when the lancing device is detached and the distal end of the housing is connected to the insertion device housing such that the one or more arms of the drive member engage a plunger head of the moveable needle.

11. The actuation device of claim 10, wherein the retracted position of the lancing device relative to the distal end portion of the housing is adjustable, and wherein the piercing member of the lancing device is arranged to extend from the distal end portion of the housing by a first distance when the lancing device is moved to the extended position, the first distance being adjustable by adjusting the retracted position of the lancing device relative to the distal end portion of the housing.

12. The actuation device of claim 10, further comprising a cover configured to be selectively attached to the connection mechanism on the housing when the lancing device is held by the distal end portion of the housing.

13. The actuation device of claim 12, wherein the connection mechanism comprises a threaded section of the distal end portion of the housing configured for engaging a threaded portion of the cover.

14. The actuation device of claim 13, wherein the threaded section of the distal end portion of the housing is configured for threaded engagement with a threaded portion of the insertion device housing when the lancing device is detached from the housing.

15. The actuation device of claim 12, wherein the cover includes an aperture through which a portion of the piercing member extends, when the lancing device is held by the distal end portion of the housing and is in the extended position.

16. The actuation device of claim 12, wherein the cover includes an aperture through which a length portion of the piercing member extends, when the lancing device is held by the distal end portion of the housing and is in the extended position, wherein the length portion of the piercing member that extends through the aperture is adjustable by adjusting the position of the cover relative to the distal end portion of the housing.

17. The actuation device of claim 16, wherein the connection mechanism comprises a threaded section of the distal end portion of the housing configured for threaded engagement with a threaded portion of the cover and adjusting the position of the cover relative to the distal end portion of the housing by adjusting the threaded engagement.

18. The actuation device of claim 10, wherein the piercing member comprises a needle.

19. A method of making an actuation device, comprising:
providing a housing having a distal end portion;
holding a lancing device with the housing, for movement relative to the distal end portion of the housing, the lancing device having a collar body carrying a piercing member;
supporting a drive member by the housing, for movement in a first direction, the drive member comprising one or more arms that are configured to releasably engage a plunger head of a moveable needle of an insertion device;
arranging the drive member to operatively engage the lancing device when the lancing device is held by the distal end portion of the housing such that the lancing device collar body at least partially surrounds the one or more arms, to move the lancing device in the first direction from a retracted position to an extended position upon movement of the drive member in the first direction, wherein the retracted position of the lancing device relative to the distal end portion of the housing is adjustable;
supporting a drive mechanism by the housing to impart a bias force on the drive member to urge the drive member in the first direction;
arranging the piercing member of the lancing device to extend from the distal end portion of the housing by a first distance when the lancing device is moved to the extended position; and
adjusting the first distance by adjusting the retracted position of the lancing device relative to the distal end portion of the housing.

\* \* \* \* \*

UNITED STATES PATENT AND TRADEMARK OFFICE
CERTIFICATE OF CORRECTION

PATENT NO. : 11,638,593 B2  
APPLICATION NO. : 16/861106  
DATED : May 2, 2023  
INVENTOR(S) : Chong et al.

Page 1 of 1

It is certified that error appears in the above-identified patent and that said Letters Patent is hereby corrected as shown below:

In the Claims

In Column 79, in Claim 1, Line 37, delete "electively" and insert -- selectively --, therefor.

Signed and Sealed this
Sixth Day of June, 2023

Katherine Kelly Vidal
*Director of the United States Patent and Trademark Office*